US012653830B2

(12) United States Patent
Cai et al.

(10) Patent No.: US 12,653,830 B2
(45) Date of Patent: Jun. 16, 2026

(54) SUBSTITUTED IMIDAZOQUINOXALINE COMPOUNDS AND USES THEREOF

(71) Applicant: Impact Therapeutics (Shanghai), Inc, Shanghai (CN)

(72) Inventors: Sui Xiong Cai, Shanghai (CN); Ye Edward Tian, Shanghai (CN); Xiaozhu Wang, Nanjing (CN)

(73) Assignee: Impact Therapeutics (Shanghai) Inc, Shanghai (CN)

( * ) Notice: Subject to any disclaimer, the term of this patent is extended or adjusted under 35 U.S.C. 154(b) by 915 days.

(21) Appl. No.: 17/642,442

(22) PCT Filed: Sep. 11, 2020

(86) PCT No.: PCT/CN2020/114823
§ 371 (c)(1),
(2) Date: Mar. 11, 2022

(87) PCT Pub. No.: WO2021/047646
PCT Pub. Date: Mar. 18, 2021

(65) Prior Publication Data

US 2022/0354859 A1 Nov. 10, 2022

(30) Foreign Application Priority Data

Sep. 12, 2019 (CN) ......................... 201910868165.3
Jan. 16, 2020 (CN) ......................... 202010063709.1

(51) Int. Cl.
*A61K 31/5377* (2006.01)
*A61K 31/4745* (2006.01)
*A61K 31/4985* (2006.01)
*A61P 35/00* (2006.01)
*C07D 487/04* (2006.01)

(52) U.S. Cl.
CPC ...... *A61K 31/5377* (2013.01); *A61K 31/4745* (2013.01); *A61K 31/4985* (2013.01); *A61P 35/00* (2018.01); *C07D 487/04* (2013.01)

(58) Field of Classification Search
CPC .......................... A61K 31/5377; C07D 487/04
See application file for complete search history.

(56) References Cited

U.S. PATENT DOCUMENTS 10,874,670 B2 12/2020 Cai et al.
2022/0259211 A1 8/2022 Cai et al.

FOREIGN PATENT DOCUMENTS

WO WO-2009068320 A1 * 6/2009 ................ A61P 1/00
WO WO-2012034526 A1 3/2012
WO WO-2015170081 A1 11/2015
WO WO-2018127195 A1 7/2018
WO WO-2018153365 A1 8/2018

OTHER PUBLICATIONS

Bakkenist, C.J., et al., "DNA damage activates ATM through intermolecular autophosphorylation and dimer dissociation," Nature 421:499-506, Springer, Germany (Jan. 2003).
Choi, M., et al., "ATM Mutation in Cancer: Therapeutic Implications," Mol Cancer Ther 15(8):1781-91, American Association for Cancer Research, United States (Aug. 2016).
Cremona, C. A., and Behrens, A., "ATM signaling and cancer," Oncogene 33(26):3351-3360, Nature Publishing Group, United Kingdom (Jun. 2014).
Cremona, C. A., et al., "Extensive DNA damage-induced sumoylation contributes to replication and repair and acts in addition to the mecl checkpoint," Mol Cell 45(3):422-432, Cell Press, United Kingdom (Feb. 2012).
Degorce, SL., et al., "Discovery of Novel 3-Quinoline Carboxamides as Potent, Selective, and Orally Bioavailable Inhibitors of Ataxia Telangiectasia Mutated (ATM) Kinase," J Med Chem, 59:6281-6292, American Chemical Society, United States (Jul. 2016).
International Search Report and Written Opinion for International Application No. PCT/CN2020/114823, China National Intellectual Property Administration, China, mailed on Dec. 10, 2020, 8 pages.
Kubota, E., et al., "Low ATM protein expression and depletion of p53 correlates with olaparib sensitivity in gastric cancer cell lines," Cell Cycle 13(13):2129-2137, Taylor & Francis, United Kingdom (May 2014).
Montani, M., et al., "ATM-depletion in breast cancer cells confers sensitivity to PARP inhibition," J Exp Clin Cancer Res 32:95, BioMed Central, United Kingdom (Nov. 2013).

(Continued)

*Primary Examiner* — John S Kenyon
*Assistant Examiner* — Sara Elizabeth Bell
(74) *Attorney, Agent, or Firm* — Sterne, Kessler, Goldstein & Fox, P.L.L.C.

(57) ABSTRACT

The disclosure provides substituted imidazo[1,5-a]quinoxaline and related compounds as kinase inhibitors, and their uses. Specifically, the disclosure provides compounds of Formula I, or pharmaceutically acceptable salts thereof or prodrugs thereof, wherein, $A_1$-$A_3$, Cy and $R_1$-$R_2$ are defined herein. The compounds of Formula I are kinase inhibitors. Therefore, the compounds of the disclosure can be used to treat clinical conditions caused by DDR function defects, such as cancers.

(I)

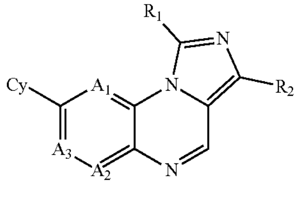

21 Claims, No Drawings

(56) References Cited

OTHER PUBLICATIONS

Toledo-Sherman, L., et al., "Optimization of Potent and Selective Ataxia Telangiectasia-Mutated Inhibitors Suitable for a Proof-of-Concept Study in Huntington's Disease Models," J Med Chem, 62:2988-3008, American Chemical Society, United States (Mar. 2019).

Weber, A. M., and Ryan, A. J., "ATM and ATR as therapeutic targets in cancer," Pharmacol Ther 149:124-138, Elsevier, Netherlands (May 2015).

Weber, A. M., et al., "Phenotypic consequences of somatic mutations in the ataxia-telangiectasia mutated gene in non-small cell lung cancer," Oncotarget 7(38):60807-60822, Impact Journals LLC, United States (Sep. 2016).

Meanwell, N.A., "Synopsis of some recent tactical application of bioisosteres in drug design," Journal of Medicinal Chemistry 54(8):2529-2591, American Chemical Society, United States (Mar. 2011).

* cited by examiner

SUBSTITUTED IMIDAZOQUINOXALINE COMPOUNDS AND USES THEREOF

TECHNICAL FIELD

This disclosure is in the field of medicinal chemistry. This disclosure especially relates to substituted imidazo[1,5-a] quinoxaline and related compounds, and their uses as kinase inhibitors, including ATM protein kinase inhibitors, and anticancer agents.

BACKGROUND

Mammalian cells face a large number of external and internal challenges that cause DNA damage every day, including DNA base mutation. These mutations cause changes in cell functions such as developing malignant tumors in mild case and cell death in severe cases. To protect against DNA damage, mammalian cells have evolved to have a sophisticated DNA damage response (DDR) mechanism. This mechanism detects and repairs DNA damage during short pauses in cell cycle to ensure accuracy in DNA replication and genomic stability, and ultimately cell survival.

DDR is closely associated with the occurrence of cancer. Scientific research has found that defects in DDR mechanism can cause cancer at multiple levels. For instance, mutations of DDR genes have been found to lead to the occurrence of a variety of cancers. Women who have mutations in BRCA1 or BRCA2 genes, important DDR components to repair DNA double strand breaks via homologous recombination mechanism, have much higher risk to develop breast cancer or ovarian cancer than those who do not have such mutations. Studies also found that deletions or loss of function of DDR proteins that play important roles in cell cycle regulation, such as p53, ATM, ATR, BRCA1/2 and so on, may lead to a variety of malignancy.

In recent years, with the development of science our understanding of the DDR mechanism has improved dramatically. Discovery of novel anticancer agents targeting mutations and loss of function of DDR component proteins has aroused great interest. For example, PARP inhibitors can selectively kill cancer cells with BRCA1/2 mutations by inhibiting single strand DNA damage repair pathway. The mechanism of losing functions of two pathways to lead cells death is called synthetic lethality.

The protein kinase ataxia-telangiectasia mutated (ATM) is one of the important components in DDR. It belongs to PI3K related serine/threonine protein kinase family. ATM kinase gene was cloned in 1995 when studying telangiectatic ataxia syndrome. ATM gene is located on human chromosome 11q22-23 with a coding sequence of 9168 bases. The ATM gene has 66 exons and the ATM protein has a molecular weight of about 350 kDa. ATM kinase is activated when DNA damage causes double strand breaks. It phosphorylates proteins that initiate involved in activation of cell cycle checkpoint, leading to cell cycle arrest. Cells will either repair the damaged DNA or undergo apoptosis (Weber and Ryan, 2016).

ATM kinase signaling pathway can be roughly divided into two mechanisms: the typical mechanism that is activated by DNA double strand breaks and the atypical mechanism that is not related to DNA damage. When DNA double strand breaks are detected, ATM kinases are transported to the position of the breaks and are activated. Although the detailed activation mechanism is still unclear, the activation process includes the division of homodimers into active monomers (Bakkenist et al., 2003), self-phosphorylation at Ser1981 and other amino acids, and acetylation. Activated ATM kinases further phosphorylate downstream substrates including cell cycle checkpoint proteins (such as CHK1 and CHK2), DNA repairing proteins (BRCA1 and RAD51), or proteins of apoptosis pathway (p53). Studies have shown that more than 700 proteins are phosphorylated after DNA double strand breaks (Choi, Kipps and Kurzrock, 2016). For the atypical mechanism, ATM is involved in functions such as metabolism, stress response, etc., that are not directly related to DNA damage (Cremona et al., 2013).

The development of new anticancer agents targeting ATM kinase mainly relies on two aspects of consideration. The DDR mechanism greatly reduced the cytotoxicity of radiotherapy or cytotoxic chemotherapeutic drugs, such as topoisomerase inhibitors, DNA methylation drugs, etc., which are targeting rapidly differentiated cancer cells by causing DNA damage. Therefore, agents that inhibit the function of DDR, such as PARP inhibitors and ATM inhibitors, can greatly enhance the efficacy of these drugs and used as combination Gilardini Montani M S et al. (J exp Clin Cancer Res, 2013, 32:95) have shown that reducing ATM expression can enhance the sensitivity of breast cancer cells to PARP inhibitors, which provides a theoretical basis for using ATM inhibitors and PARP inhibitors in combination for the treatment of breast cancer. Furthermore, Kubota e et al. (Cell Cycle, 2014, 13 (13): 2129-2137) found that the expression level of ATM protein in gastric cancer cells was significantly correlated with the sensitivity of the cells to PARP inhibitor Olaparib, and small molecular ATM inhibitor enhanced the sensitivity of p53 inactivated gastric cancer cells to Olaparib. Therefore, the combination of ATM inhibitor and PARP inhibitor may be useful in treating gastric cancer. Accordingly, for cancer cells with DDR function defect, ATM kinase inhibitors may be used as single agent through synthetic lethality mechanism. Anticancer drugs targeting certain mechanism and patient population may have good efficacy and low toxicity.

Degorce S L et al. (J Med Chem, 2016, 59: 6281-6292) reported a series of 3-quinoline formamide as ATM kinase inhibitors that had good efficacy in combination with irinotecan in animal models.

Genetic and pharmacological evidences have shown that reducing the activity of ATM kinase can reduce the toxicity of mutant Huntington (mHTT) protein in cells and animal models of Huntington's disease (HD), suggesting that selective inhibition of ATM may provide a new clinical intervention for the treatment of HD. Leticia T S et al. (J Med Chem, 2019, 62:2988-3008) reported an ATM inhibitor that was able to cross the blood-brain barrier to have good pharmacodynamic (PD) effect that was consistent with the inhibitory effect on ATM kinase in mouse brain, an obvious pharmacokinetic/pharmacodynamic (PK/PD) relationship.

Fused heteroaryl compounds have been disclosed as kinase inhibitors. For example, WO2012034526 disclosed fused heteroaryl compounds as PI3K kinase inhibitors. WO2015170081 discloses imidazoquinolinone as an ATM kinase inhibitor. WO2018127195 and WO2018153365 disclosed substituted fused heteroaryl compounds as kinase inhibitors, especially as ATM kinase inhibitors.

SUMMARY

The disclosure provides novel substituted imidazo[1,5-a] quinoxaline compounds as represented in Formula I, Formula II, Formula IIIa and Formula IIIb as kinase inhibitors, especially as ATM kinase inhibitors.

The disclosure also provides pharmaceutical compositions comprising an effective amount of the compounds of Formula I, Formula II, Formula IIIa or Formula IIIb, for the treatment of cancer.

In a particular embodiment, the pharmaceutical composition may also comprise one or more pharmaceutically acceptable carriers or diluters, for the treatment of cancer.

In a particular embodiment, the pharmaceutical composition may also comprise at least one known anticancer agent or pharmaceutically acceptable salts thereof, for the treatment of cancer.

The disclosure is also directed to methods for the preparation of novel compounds of Formulae I, Formula II, Formula IIIa and Formula IIIb.

DETAILED DESCRIPTION

The disclosure found that substituted imidazo[1,5-a]quinoxaline compounds as represented in Formula I have kinase inhibitory activity and can be used as kinase inhibitors, especially as ATM kinase inhibitors.

It should be understood that the characteristics of the embodiments described herein can be arbitrarily combined to form the technical solution of this disclosure. The definition of each group herein shall apply to any of the embodiments described herein. For example, the definitions of the substituents of alkyl herein shall apply to any of the embodiments described herein unless the substituents of alkyl are clearly defined in the embodiment.

Specifically, the disclosure provides compounds as represented in Formula I or stereoisomers, tautomers, N-oxides, hydrates, isotope-substituted derivatives, solvates, or pharmaceutically acceptable salts thereof, or mixtures thereof, or prodrugs thereof:

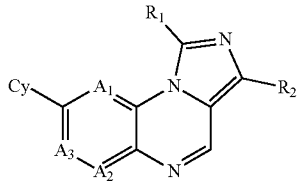

I wherein, $A_1$, $A_2$ and $A_3$ are independently N, $CR_4$, $CR_5$ and $CR_6$;

- Cy is an optionally substituted aryl, an optionally substituted heteroaryl, an optionally substituted heterocyclic group or an optionally substituted cycloalkyl;
- $R_1$ is an optionally substituted alkyl, an optionally substituted alkoxy, an optionally substituted amino, an optionally substituted carbocyclic group, an optionally substituted heterocyclic group, an optionally substituted aryl or an optionally substituted heteroaryl;
- $R_2$ is H, an optionally substituted alkyl or an optionally substituted carbocyclic group;
- $R_4$, $R_5$ and $R_6$ are independently hydrogen, halogen, alkyl, alkoxy, alkenyl, alkynyl, amino, nitro, cyano, acylamino, acyloxy, hydroxy, sulfhydryl, alkylthio, azido or carboxyl; wherein the alkyl, alkoxy, alkenyl, alkynyl, amino, acylamino, acyloxy, hydroxy, sulfhydryl, alkylthio and carboxyl may be optionally substituted.

In compound of Formula I of each embodiment of the disclosure, preferably, $A_1$ is N or $CR_4$, $A_2$ is N or $CR_5$, $A_3$ is N or $CR_6$. More preferably, $A_1$ is $CR_4$, $A_2$ is $CR_5$, and $A_3$ is $CR_6$; preferably, $R_4$, $R_5$ and $R_6$ are independently H, alkyl, alkoxy or halogen; further preferably, $R_4$ and $R_5$ are H, and $R_6$ is H, halogen or alkoxy.

In compound of Formula I of each embodiment of the disclosure, Cy is preferably an optionally substituted 5 or 6-membered heteroaryl containing 1, 2 or 3 nitrogen atoms, or an optionally substituted aryl. The heteroaryl includes, but is not limited to, pyridyl, pyrrolyl, imidazolyl, pyrazolyl, pyrazinyl and pyrimidinyl; in some preferred embodiments, Cy is an optionally substituted pyrazolyl; in some preferred embodiments, Cy is an optionally substituted pyridyl; in some preferred embodiments, Cy is an optionally substituted phenyl. The aryl includes, but is not limited to, phenyl and naphthyl. The number of the substituent on Cy may be 1, 2, 3, 4 or 5, and the substituent includes but is not limited to halogen, alkyl, alkoxy, alkenyl, alkynyl, amino, nitro, cyano, acylamino, acyloxy, hydroxy, sulfhydryl, alkylthio, azido, carboxyl, carbocyclic group, heterocyclic group, aryl or heteroaryl; wherein the alkyl, alkoxy, alkenyl, alkynyl, amino, acylamino, acyloxy, hydroxy, sulfhydryl, alkylthio, carboxyl, carbocyclic group, heterocyclic group, aryl and heteroaryl may be optionally substituted, for example, by 1, 2 or 3 substituents selected from alkyl, aminoalkyl, alkoxy, hydroxy, halogen, amino, heterocyclic group, and heteroaryl. Preferably, the amino is $NR_{11}R_{12}$, wherein, $R_{11}$ and $R_{12}$ are independently selected from hydrogen or $C_{1-6}$ alkyl, or $R_{11}$ and $R_{12}$ together with N form a 4 to 8-membered heterocyclic group, such as azetidinyl, pyrrolidinyl, piperidinyl, piperazinyl or morpholinyl (such as morpholino), which can be optionally substituted by, such as 1-3 substituents selected from the group consisting of halogen, alkyl and alkoxy.

In preferred embodiments, the substituent on Cy is as defined in any of the following embodiments of formulae II, IIIa and IIIb. In some embodiments, the substituent on Cy is halogen, an optionally substituted $C_{1-6}$ alkyl, an optionally substituted $C_{1-6}$ alkoxy, an optionally substituted amino or an optionally substituted heterocyclic group; preferably, the substituent on the alkyl is selected from the group consisting of halogen, hydroxy and amino, preferably halogen; preferably, the substituent on the alkoxy is selected from the group consisting of halogen, hydroxy, heteroaryl (preferably 5 or 6-membered nitrogen-containing heteroaryl, such as pyrazolyl, imidazolyl, pyridyl, pyrimidyl, pyrazinyl, etc), and amino, preferably amino; preferably, the substituent on the heterocyclic group is selected from the group consisting of $C_{1-4}$ alkyl, halogen, hydroxy and amino, and the preferred heterocyclic group is a heterocyclic group containing one N and/or one O, including but not limited to tetrahydrofuranyl, morpholinyl (such as morpholino), piperidinyl and piperazinyl. Preferably, the amino is $NR_{11}R_{12}$, wherein $R_{11}$ and $R_{12}$ are independently selected from hydrogen or $C_{1-6}$ alkyl, or $R_{11}$ and $R_{12}$ together with N form a 4 to 8-membered heterocyclic group, such as azetidinyl, pyrrolidinyl, piperidinyl, piperazinyl or morpholinyl (such as morpholino), which can be optionally substituted by, such as 1-3 substituents selected from the group consisting of halogen, alkyl and alkoxy. In some preferred embodiments, when Cy is a 6-membered ring, preferably, the substituted $C_{1-6}$ alkoxy, the substituted amino or the optionally substituted heterocyclic group is located at the para position.

In compound of Formula I, preferably, $R_1$ is an optionally substituted $C_{1-6}$ alkyl, an optionally substituted heterocyclic group or an optionally substituted heteroaryl. Preferred heterocyclic group is a heterocyclic group containing one O and/or one N, such as tetrahydropyranyl, morpholinyl (such as morpholino), piperidinyl and piperazinyl. Preferred heteroaryl is a heteroaryl containing one to three nitrogen atoms, such as pyridyl. The substituent on the heterocyclic group and the heteroaryl is preferably one or more (such as 1-3) groups selected from the group consisting of hydroxy, $C_{1-4}$ alkyl, amino, halogen, $C_{1-4}$ alkoxy and carboxyl, more preferably $C_{1-4}$ alkyl, halogen and $C_{1-4}$ alkoxy. The substituent on the $C_{1-6}$ alkyl may be one or more (such as 1-3) groups selected from the group consisting of amino, hydroxyl, halogen and $C_{1-4}$ alkoxy.

In compound of Formula I, preferably, $R_2$ is an optionally substituted $C_{1-10}$ alkyl, preferably $C_{1-6}$ alkyl, more preferably $C_{1-4}$ alkyl, including but not limited to methyl, ethyl, propyl and isopropyl. When $R_2$ is an optionally substituted carbocyclic group, preferred $R_2$ is an optionally substituted $C_{3-8}$ cycloalkyl; the substituent on the carbocyclic group is preferably 1 or 2 substituents selected from the group consisting of hydroxy, halogen, amino, $C_{1-4}$ alkyl, $C_{1-4}$ alkoxy and carboxyl.

In compound of Formula I, preferably, $R_4$, $R_5$ and $R_6$ are independently selected from H, alkyl, alkoxy or halogen.

Compounds of Formula I preferably have the structure as represented in the following Formula II.

II

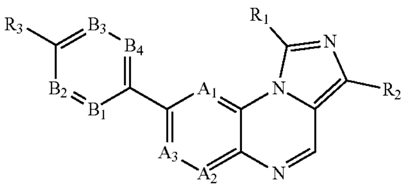

wherein $A_1$, $A_2$ and $A_3$ are independently N, $CR_4$, $CR_5$ and $CR_6$;

- $B_1$, $B_2$, $B_3$ and $B_4$ are independently N, $CR_7$, $CR_8$, $CR_9$ and $CR_{10}$;
- $R_1$ is an optionally substituted alkyl, an optionally substituted alkoxy, an optionally substituted amino, an optionally substituted carbocyclic group, an optionally substituted heterocyclic group, an optionally substituted aryl or an optionally substituted heteroaryl;
- $R_2$ is an optionally substituted alkyl or an optionally substituted carbocyclic group;
- $R_3$ is hydrogen, alkyl, alkoxy, amino, carbocyclic group, heterocyclic group, aryl or heteroaryl; wherein the alkyl, alkoxy, amino, carbocyclic group, heterocyclic group, aryl or heteroaryl may be optionally substituted.
- $R_4$, $R_5$, $R_6$, $R_7$, $R_8$, $R_9$ and $R_{10}$ are independently hydrogen, halogen, alkyl, alkoxy, alkenyl, alkynyl, amino, nitro, cyano, acylamino, acyloxy, hydroxy, sulfhydryl, alkylthio, azido or carboxyl; wherein the alkyl, alkoxy, alkenyl, alkynyl, amino, acylamino, acyloxy, hydroxy, sulfhydryl, alkylthio and carboxyl may be independently optionally substituted.

In compound of Formula II, preferably, $A_1$ is N or $CR_4$, $A_2$ is N or $CR_5$, $A_3$ is N or $CR_6$.

In compound of Formula II, preferably, $B_1$ is N or $CR_7$, $B_2$ is N or $CR_8$, $B_3$ is N or $CR_9$; and $B_4$ is N or $CR_{10}$.

In compound of Formula II, preferably, $A_1$, $A_2$ and $A_3$ are independently $CR_4$, $CR_5$ and $CR_6$. In some embodiments, one of $A_1$, $A_2$ and $A_3$ is N, the others are two groups selected from the group consisting of $CR_4$, $CR_5$ and $CR_6$. In some embodiments, $A_1$ is N, $A_2$ and $A_3$ are $CR_5$ and $CR_6$, respectively; or $A_2$ is N, $A_1$ and $A_3$ are $CR_4$ and $CR_6$, respectively; or $A_3$ is N, $A_1$ and $A_2$ are $CR_4$ and $CR_5$, respectively. Preferred $R_4$, $R_5$ and $R_6$ are independently hydrogen, halogen, $C_{1-4}$ alkyl, $C_{1-4}$ alkoxy or halogenated $C_{1-4}$ alkyl, more preferably independently hydrogen, halogen or $C_{1-4}$ alkoxy. In preferred embodiments, $R_4$ and $R_5$ are independently hydrogen or $C_{1-4}$ alkyl, more preferably hydrogen; $R_6$ is hydrogen, halogen or $C_{1-4}$ alkoxy. In some preferred embodiments, $A_1$, $A_2$ and $A_3$ are $CR_4$, $CR_5$ and $CR_6$, respectively, and $R_4$, $R_5$ and $R_6$ are hydrogen; in some other preferred embodiments, $R_4$ and $R_5$ are hydrogen, $R_6$ is halogen or $C_{1-4}$ alkoxy.

In compound of Formula II, preferably, one of $B_1$, $B_2$, $B_3$ and $B_4$ is N, for example, the ring containing $B_1$, $B_2$, $B_3$ and $B_4$ is pyridine ring; preferably, $B_2$ is N, the others are three groups selected from $CR_7$, $CR_8$, $CR_9$ and $CR_{10}$, more preferably $B_1$, $B_3$ and $B_4$ are $CR_7$, $CR_9$ and $CR_{10}$, respectively; preferably, in these embodiments, $R_7$, $R_8$, $R_9$ and $R_{10}$ are independently hydrogen, halogen, $C_{1-4}$ alkyl, $C_{1-4}$ alkoxy and halogenated $C_{1-4}$ alkyl, more preferably $R_7$, $R_8$, $R_9$ and $R_{10}$ are hydrogen. In some embodiments, $B_1$, $B_2$, $B_3$ and $B_4$ are $CR_7$, $CR_8$, $CR_9$ and $CR_{10}$, respectively, which means that the ring containing $B_1$, $B_2$, $B_3$ and $B_4$ is phenyl ring that may be optionally substituted. Preferably, $R_7$, $R_8$, $R_9$ and $R_{10}$ are independently hydrogen, halogen, $C_{1-4}$ alkyl, $C_{1-4}$ alkoxy and halogenated $C_{1-4}$ alkyl. More preferably, at least one of $R_7$, $R_8$, $R_9$ and $R_{10}$ is not hydrogen; preferably, $R_8$ is not hydrogen, and is preferably selected from halogen and halogenated $C_{1-4}$ alkyl. In some embodiments, $B_1$, $B_2$, $B_3$ and $B_4$ are $CR_7$, $CR_8$, $CR_9$ and $CR_{10}$, respectively; $R_8$ is not hydrogen, for example, is halogen, $C_{1-4}$ alkoxy or halogenated $C_{1-4}$ alkyl; $R_7$, $R_9$ and $R_{10}$ are hydrogen.

$R_1$ of compound of Formula II is preferably selected from the group consisting of an optionally substituted $C_{1-6}$ alkyl, an optionally substituted heteroaryl and an optionally substituted heterocyclic group. Preferred alkyl is $C_{1-3}$ alkyl, such as methyl, ethyl, and isopropyl. Preferred heteroaryl is a heteroaryl containing one to three nitrogen atoms, such as pyridyl. Preferred heterocyclic group is a heterocyclic group containing one O and/or one N, such as tetrahydrofuranyl, morpholinyl (such as morpholino), piperidinyl and piperazinyl. In preferred embodiments, the optionally substituted heterocyclic group is tetrahydro-2H-furan-4-yl, 1-morpholinyl, piperidin-1-yl or piperazin-1-yl. The substituent on the heteroaryl or the heterocyclic group is preferably one or more (such as 1-3) groups selected from a group consisting of hydroxy, $C_{1-4}$ alkyl, amino, halogen, $C_{1-4}$ alkoxy and carboxyl, more preferably $C_{1-4}$ alkyl, halogen and $C_{1-4}$ alkoxy. Preferably, the substituent(s) are located at the meta position and/or para position when the heteroaryl or the heterocyclic group is a 6-membered ring. The substituent on the $C_{1-6}$ alkyl may be one or more (such as 1-3) groups selected from the group consisting of amino, hydroxyl, halogen and $C_{1-4}$ alkoxy.

In some preferred embodiments, $R_1$ is unsubstituted isopropyl; in some preferred embodiments, $R_1$ is unsubstituted tetrahydrofuranyl; in some preferred embodiments, $R_1$ is morpholinyl that is optionally substituted by 1 or 2 $C_{1-4}$ alkyls, preferably the substituent(s) are located at the meta position; in some preferred embodiments, $R_1$ is piperidinyl or piperazinyl that is optionally substituted by 1-3 $C_{1-4}$ alkyls, preferably the substituent(s) are located at the para position and/or meta position. In some embodiments, $R_1$ of compound of Formula II is preferably an optionally substituted heteroaryl. Exemplary heteroaryl includes but is not limited to heteroaryl containing 1-3 nitrogen atoms, such as pyridyl, pyrrolyl, imidazolyl, pyrazolyl, pyrazinyl and pyrimidinyl, etc; exemplary substituents include but are not limited to halogen, $C_{1-4}$ alkyl and $C_{1-4}$ alkoxy. Exemplary $R_1$ is selected from:

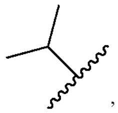,
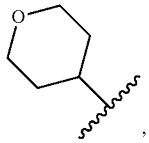,
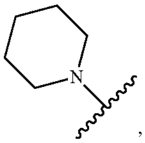,
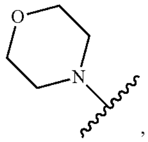,
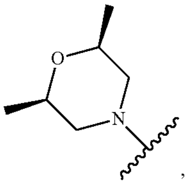,
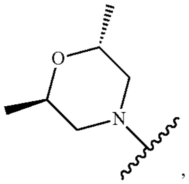,
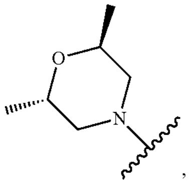,
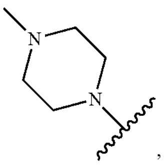,
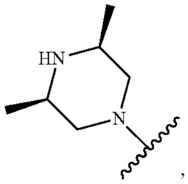,
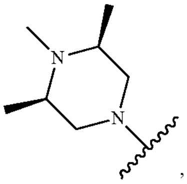, and
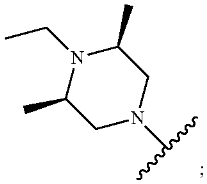;

$R_2$ of compound of Formula II is preferably $C_{1-10}$ alkyl, more preferably $C_{1-6}$ alkyl, more preferably $C_{1-4}$ alkyl, including but not limited to methyl, ethyl, propyl and isopropyl. When $R_2$ of compound of Formula II is an optionally substituted carbocyclic group, preferred $R_2$ is an optionally substituted $C_{3-8}$ cycloalkyl; the substituent on the carbocyclic group is preferably 1 or 2 substituents selected from the group consisting of hydroxy, halogen, amino, $C_{1-4}$ alkyl, $C_{1-4}$ alkoxy and carboxyl.

When $R_3$ of compound of Formula II is substituted, the number of the substituent is preferably 1, 2 or 3; preferred substituent is selected from $C_{1-4}$ alkyl, $C_{1-4}$ alkoxy, halogen, hydroxy, amino, and heteroaryl. Preferred $R_3$ is an optionally substituted $C_{1-6}$ alkyl, an optionally substituted $C_{1-6}$ alkoxy, an optionally substituted amino or an optionally substituted heterocyclic group, more preferably a substituted $C_{1-6}$ alkoxy, a substituted amino or a substituted heterocyclic group. More preferred $R_3$ is a substituted $C_{1-6}$ alkoxy, $-NR_{11'}-C_{1-6}$ alkyl-$NR_{11'}R_{12'}$ or a substituted heterocyclic group, wherein $R_{11'}$, and $R_{12'}$ are independently selected from the group consisting of H and $C_{1-4}$ alkyl or they together with N form 4 to 8-membered heterocyclic group, such as azetidinyl, pyrrolidinyl, piperidinyl, piperazinyl or morpholinyl (morpholino), which can be optionally substituted by, such as 1-3 substituents selected from the group consisting of halogen, alkyl and alkoxy. Preferably, the substituent on the alkoxy is selected from the group consisting of halogen, hydroxy, heteroaryl (preferably 5 or 6-membered nitrogen-containing heteroaryl, such as pyrazolyl, imidazolyl, pyridyl, pyrimidinyl, pyrazinyl, etc) and amino, preferably amino. Preferably, the substituent on the heterocyclic group is preferably selected from $C_{1-4}$ alkyl, halogen, hydroxy and amino, preferably the heterocyclic group is a heterocyclic group containing one N and/or one O, including but not limited to tetrahydrofuranyl, morpholinyl, piperidinyl and piperazinyl. Preferably, the amino is $NR_{11}R_{12}$, wherein, $R_{11}$ and $R_{12}$ are independently selected from hydrogen or $C_{1-6}$ alkyl, or $R_{11}$ and $R_{12}$ together with N form 4 to 8-membered heterocyclic group, such as azetidinyl, pyrrolidinyl, piperidinyl, piperazinyl or morpholinyl (morpholino), which can be optionally substituted by, such as 1-3 substituents selected from the group consisting of halogen, alkyl and alkoxy. Exemplary $R_3$ is selected from:

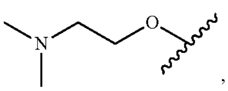,
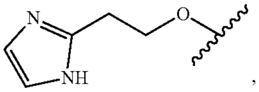,
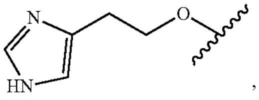,
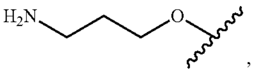,
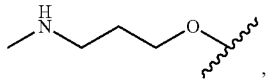,
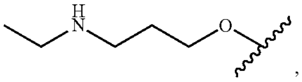,
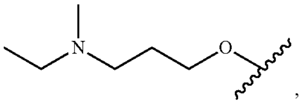,
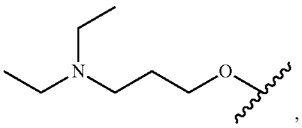,
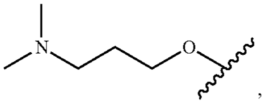,
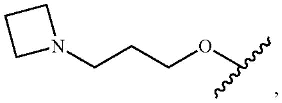,
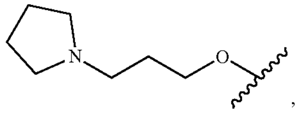,
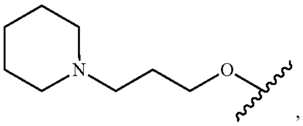,
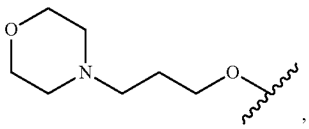,
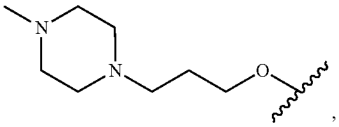,
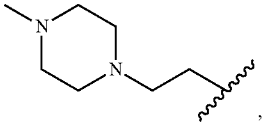,
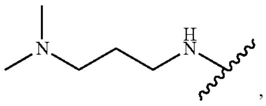,
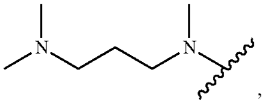,
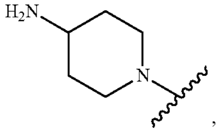, -continued

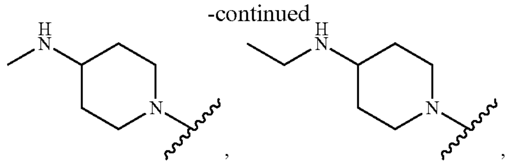

, ,

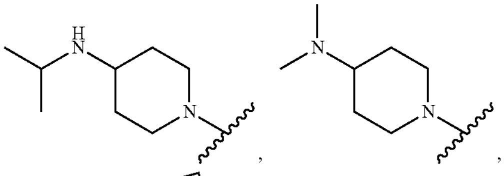

, , and

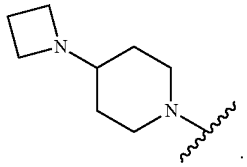

.

In the specially preferred compounds of Formula II, $R_2$ is $C_{1-4}$ alkyl, and the other groups are as described in any of the above embodiments.

One group of the preferred compounds of the disclosure is represented as compounds of Formulae IIIa and IIIb or stereoisomers, tautomers, N-oxides, hydrates, isotope-substituted derivatives, solvates thereof or pharmaceutically acceptable salts thereof, or mixtures thereof or prodrugs thereof:

IIIa

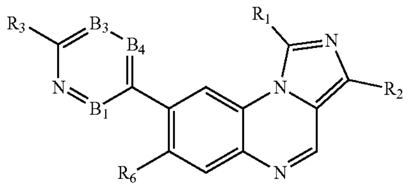

IIIb

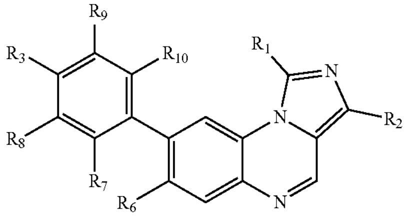

wherein $B_1$, $B_3$, $B_4$, $R_1$, $R_2$, $R_3$, $R_7$, $R_8$, $R_9$ and $R_{10}$ are as defined in Formula I or II; $R_6$ is hydrogen, halogen, alkyl or alkoxy.

In one or more embodiments of compounds of Formulae IIIa and IIIb, the $B_1$, $B_3$, $B_4$, $R_1$, $R_2$, $R_3$, $R_7$, $R_8$, $R_9$ and $R_{10}$ are as described in any one of the foregoing embodiments of Formula I or II, respectively.

In one or more of the foregoing embodiments of compounds of Formulae IIIa and IIIb, $R_2$ is $C_{1-3}$ alkyl, preferably methyl.

In one or more of the foregoing embodiments of compound of Formula IIIa, $B_1$, $B_3$ and $B_4$ are $CR_7$, $CR_9$ and $CR_{10}$, respectively; $R_7$, $R_9$ and $R_{10}$ are independently hydrogen, halogen, $C_{1-4}$ alkyl or halogenated $C_{1-4}$ alkyl. Preferably, $R_7$, $R_9$ and $R_{10}$ are all hydrogen.

In one or more embodiments of compound of Formula IIIb, $R_8$ is hydrogen, halogen, $C_{1-4}$ alkoxy, $C_{1-4}$ alkyl or halogenated $C_{1-4}$ alkyl; preferably, $R_8$ is halogen, $C_{1-4}$ alkoxy and halogenated $C_{1-4}$ alkyl. Preferably, $R_7$, $R_9$ and $R_{10}$ are independently hydrogen, halogen, $C_{1-4}$ alkyl or halogenated $C_{1-4}$ alkyl, preferably hydrogen.

In one or more of the foregoing embodiments of compounds of Formulae IIIa and IIIb, $R_1$ is an optionally substituted $C_{1-6}$ alkyl, an optionally substituted heteroaryl or an optionally substituted heterocyclic group. Preferred alkyl is $C_{1-3}$ alkyl, such as isopropyl. Preferred heteroaryl is a heteroaryl containing one to three nitrogen atoms, such as pyridyl. Preferred heterocyclic group is a heterocyclic group containing one O and/or one N, such as tetrahydrofuranyl, morpholinyl (such as morpholino), piperidinyl and piperazinyl. In preferred embodiments, the optionally substituted heterocyclic group is tetrahydro-2H-furan-4-yl, 1-morpholinyl, piperidin-1-yl or piperazin-1-yl. The substituent on the heteroaryl and the heterocyclic group is preferably one or more (such as 1-3) groups selected from hydroxy, $C_{1-4}$ alkyl, amino, halogen, $C_{1-4}$ alkoxy and carboxyl, more preferably $C_{1-4}$ alkyl, halogen and $C_{1-4}$ alkoxy. Preferably, the substituent(s) are located at the meta position and/or para position when the heteroaryl or the heterocyclic group is a 6-membered ring. The substituent on the $C_{1-6}$ alkyl may be one or more (such as 1-3) groups selected from the group consisting of amino, hydroxyl, halogen and $C_{1-4}$ alkoxy. In some preferred embodiments, $R_1$ is unsubstituted isopropyl; in some preferred embodiments, $R_1$ is unsubstituted tetrahydrofuranyl; in some preferred embodiments, $R_1$ is morpholinyl that is optionally substituted by 1 or 2 $C_{1-4}$ alkyls, preferably the substituent(s) are located at the meta position; in some preferred embodiments, $R_1$ is piperidinyl or piperazinyl that is optionally substituted by 1-3 $C_{1-4}$ alkyls, preferably the substituent(s) are located at the para position and/or meta position. Exemplary $R_1$ is selected from:

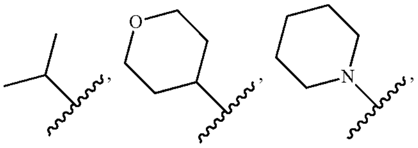

, , ,

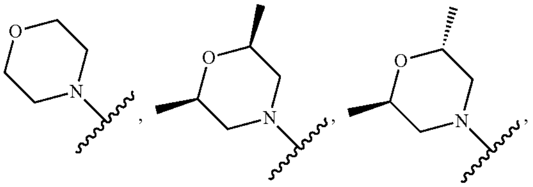

, , ,

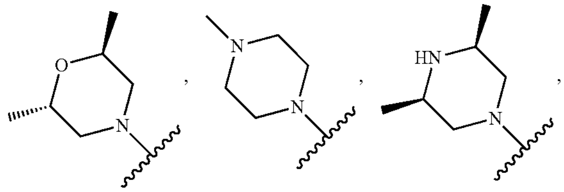

, , ,

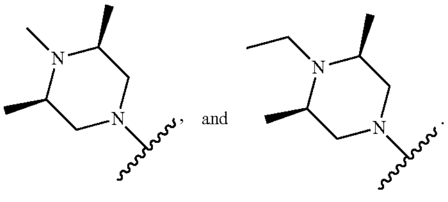

, and .

In one or more of the foregoing embodiments of compound of Formula IIIa, the ring containing $B_1$, $B_3$ and $B_4$ is optionally substituted pyridine ring. It should be understood that, in this disclosure, in addition to $R_3$, the substituents on the ring containing $B_1$, $B_3$ and $B_4$ may also include $R_7$, $R_9$ and $R_{10}$. Preferred $R_7$, $R_9$ and $R_{10}$ are independently selected from halogen, $C_{1-4}$ alkyl and halogenated $C_{1-4}$ alkyl.

In one or more of the foregoing embodiments of compounds of Formulae IIIa and IIIb, when $R_3$ is substituted, the number of the substituent is preferably 1-3; preferred substituent is selected from $C_{1-4}$ alkyl, $C_{1-4}$ alkoxy, halogen, hydroxy, amino and heteroaryl. Preferred $R_3$ is an optionally substituted $C_{1-6}$ alkyl, an optionally substituted $C_{1-6}$ alkoxy, an optionally substituted amino, or an optionally substituted heterocyclic group. More preferred $R_3$ is a substituted $C_{1-6}$ alkoxy, —$NR_{11'}$—$C_{1-6}$ alkyl-$NR_{11'}R_{12'}$ or a substituted heterocyclic group, wherein $R_{11'}$ and $R_{12'}$ are independently selected from the group consisting of H and $C_{1-4}$ alkyl or they together with N form 4 to 8-membered heterocyclic group, such as azetidinyl, pyrrolidinyl, piperidinyl, piperazinyl or morpholinyl (morpholino), which can be optionally substituted by, such as 1-3 substituents selected from the group consisting of halogen, alkyl and alkoxy. Preferably, the substituent on the alkoxy is selected from halogen, hydroxy, heteroaryl (preferably 5 or 6-membered nitrogen-containing heteroaryl, such as pyrazolyl, imidazolyl, pyridyl, pyrimidinyl, pyrazinyl, etc) and amino, preferably amino; preferably, the substituent on the heterocyclic group is preferably selected from $C_{1-4}$ alkyl, halogen, hydroxy and amino, preferably the heterocyclic group is heterocyclic group containing one N and/or one O, including but not limited to tetrahydrofuranyl, morpholinyl, piperidinyl and piperazinyl. Preferably, the amino is $NR_{11}R_{12}$, wherein, $R_{11}$ and $R_{12}$ are independently selected from hydrogen or $C_{1-6}$ alkyl, or $R_{11}$ and $R_{12}$ together with N form a 4 to 8-membered heterocyclic group, such as azetidinyl, pyrrolidinyl, piperidinyl, piperazinyl or morpholinyl (morpholino), which can be optionally substituted by, such as 1-3 substituents selected from the group consisting of halogen, alkyl and alkoxy. Exemplary $R_3$ is selected from:

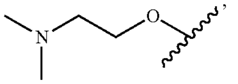 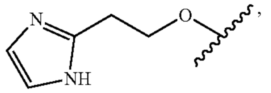

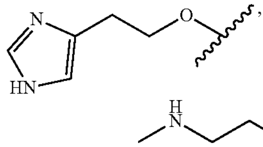 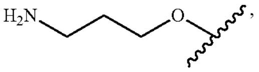

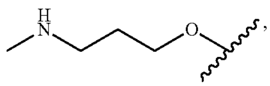

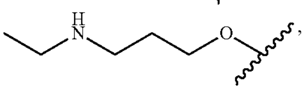

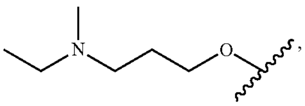

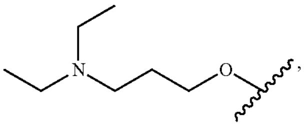 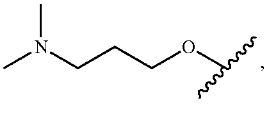

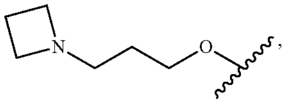

-continued

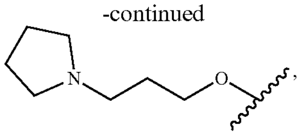

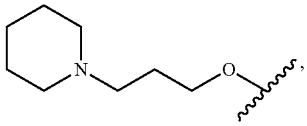

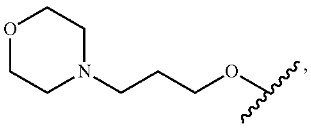

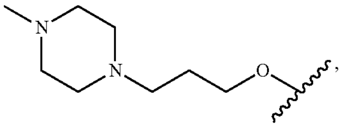

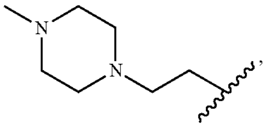 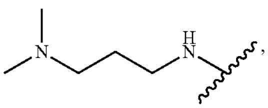

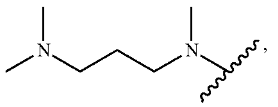 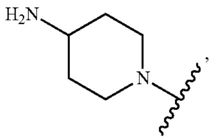

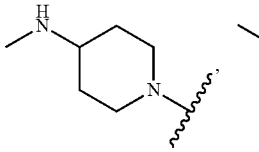 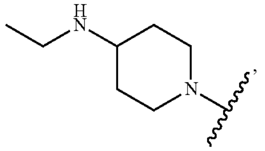

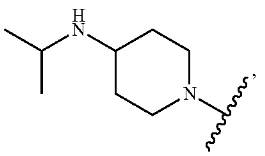 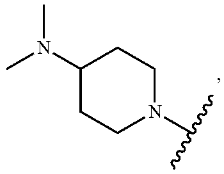 , and

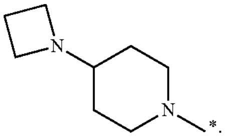

In one or more of the foregoing embodiments of compounds of Formulae IIIa and IIIb, $R_6$ is hydrogen, halogen and $C_{1-4}$ alkoxy. Preferably, $R_6$ is hydrogen.

In one or more of the foregoing embodiments of Formulae I, II, IIIa and IIIb, the optionally substituted alkyl, alkoxy, amino, carbocyclic group, heterocyclic group, aryl or heteroaryl for $R_1$ may be substituted by one or more substituents selected from the substituents for the alkyl, alkoxy, amino, carbocyclic group, heterocyclic group, aryl or heteroaryl described herein.

In one or more of the foregoing embodiments of Formulae I, II, IIIa and IIIb, the optionally substituted alkyl, alkoxy, amino, carbocyclic group, heterocyclic group, aryl or heteroaryl for $R_3$ may be substituted by one or more substituents selected from the substituents for the alkoxy, amino, carbocyclic group, heterocyclic group, aryl or heteroaryl described herein.

In one or more of the foregoing embodiments of Formulae II, IIIa and IIIb, the substituent(s) of the optionally substituted alkyl, alkoxy, alkenyl, alkynyl, amino, acylamino, acyloxy, hydroxy, sulfydryl, alkylthio or carboxyl for $R_4$, $R_5$, $R_6$, $R_7$, $R_8$, $R_9$ and $R_{10}$ is selected from one or more substituents for the alkyl, alkoxy, alkenyl, alkynyl, amino, acylamino, acyloxy, hydroxy, sulfydryl, alkylthio or carboxyl described herein.

In one or more of the foregoing embodiments of Formula IIIb, the substituent(s) of the optionally substituted alkyl, alkoxy, alkenyl, alkynyl, amino, acylamino, acyloxy, hydroxy, sulfydryl, alkylthio or carboxyl for $R_7$, $R_8$, $R_9$ and $R_{10}$ is selected from one or more substituents for the alkyl, alkoxy, alkenyl, alkynyl, amino, acylamino, acyloxy, hydroxy, sulfydryl, alkylthio or carboxyl described herein.

In one or more preferred embodiments of Formulae II, IIIa and IIIb: $A_1$, $A_2$ and $A_3$ are $CR_4$, $CR_5$ and $CR_6$, respectively, wherein, $R_4$, $R_5$ and $R_6$ are independently hydrogen, halogen, $C_{1-4}$ alkyl, $C_{1-4}$ alkoxy or halogenated $C_{1-4}$ alkyl, preferably independently hydrogen, halogen and $C_{1-4}$ alkyl, more preferably $R_4$ and $R_5$ are H, $R_6$ is H, halogen or alkoxy; the ring containing $B_1$, $B_2$, $B_3$ and $B_4$ (Formula II) or the ring containing $B_1$, $B_3$ and $B_4$ (Formula IIIa) is optionally substituted pyridine ring or optionally substituted phenyl ring, wherein, $R_7$, $R_8$, $R_9$ and $R_{10}$ are independently selected from hydrogen, $C_{1-6}$ alkyl, halogen and halogenated $C_{1-6}$ alkyl, preferably independently halogen and halogenated $C_{1-4}$ alkyl, more preferably $R_7$, $R_9$ and $R_{10}$ are H, $R_8$ is halogen or halogenated $C_{1-4}$ alkyl; $R_1$ is an optionally substituted $C_{1-6}$ alkyl, heteroaryl or heterocyclic group that is optionally substituted by 1-4 $C_{1-6}$ alkyls, preferably selected from $C_{1-4}$ alkyl, tetrahydropyranyl that is optionally substituted by 1-4 $C_{1-6}$ alkyls, piperidinyl that is optionally substituted by 1-4 $C_{1-6}$ alkyls, morpholinyl that is optionally substituted by 1-4 $C_{1-6}$ alkyls and piperazinyl that is optionally substituted by 1-4 $C_{1-6}$ alkyls; $R_2$ is $C_{1-6}$ alkyl, preferably $C_{1-4}$ alkyl, more preferably methyl; $R_3$ is selected from $C_{1-6}$ alkyl that is optionally substituted by —$NR_{11}R_{12}$, $C_{1-6}$ alkoxy that is optionally substituted by —$NR_{11}R_{12}$, and heterocyclic group that is optionally substituted by —$NR_{11}R_{12}$, wherein, $R_{11}$ and $R_{12}$ are independently selected from hydrogen or $C_{1-6}$ alkyl; or $R_{11}$ and $R_{12}$ together with N form 4 to 8-membered heterocyclic group that can be optionally substituted, such as azetidinyl, pyrrolidinyl, piperidinyl, and morpholinyl (such as morpholino), piperazinyl. Preferably, $R_6$ is hydrogen, halogen or $C_{1-4}$ alkoxy.

In one or more of embodiments of Formula IIIa:

$B_1$, $B_3$, and $B_4$ are CH;

$R_1$ is a heterocyclic group optionally substituted by 1-2 substituents selected from the group consisting of $C_{1-6}$ alkyl, preferably $R_1$ is morpholinyl (such as morpholino) optionally substituted by 1-2 $C_{1-6}$ alkyls;

$R_2$ is $C_{1-4}$ alkyl, preferably methyl;

$R_3$ is a $C_{1-6}$ alkoxy optionally substituted by —$NR_{11}R_{12}$, or a heterocyclic group optionally substituted by —$NR_{11}R_{12}$, wherein $R_{11}$ and $R_{12}$ are independently selected from hydrogen or $C_{1-6}$ alkyl or $R_{11}$ and $R_{12}$ together with the N atom form a 4 to 8-membered heterocyclic group (such as azetidinyl, pyrrolidinyl, piperidinyl, and morpholinyl (such as morpholino), piperazinyl) optionally substituted by 1-2 alkyls; preferably the heterocyclic group optionally substituted by —$NR_{11}R_{12}$ is a piperidinyl or a piperazinyl with their ring nitrogen atom linking to the rest of the compound, which preferably is substituted by the —$NR_{11}R_{12}$ group; and $R_6$ is hydrogen, halogen or $C_{1-4}$ alkoxy, preferably hydrogen.

In one or more of embodiments of Formula IIIb:

$R_1$ is a heterocyclic group optionally substituted by 1-2 substituents selected from the group consisting of $C_{1-6}$ alkyl, preferably $R_1$ is morpholinyl (such as morpholino) optionally substituted by 1-2 $C_{1-6}$ alkyls;

$R_2$ is $C_{1-4}$ alkyl, preferably methyl;

$R_3$ is a $C_{1-6}$ alkoxy optionally substituted by —$NR_{11}R_{12}$, or a heterocyclic group optionally substituted by —$NR_{11}R_{12}$, wherein $R_{11}$ and $R_{12}$ are independently selected from hydrogen or $C_{1-6}$ alkyl or $R_{11}$ and $R_{12}$ together with the N atom form a 4 to 8-membered heterocyclic group (such as azetidinyl, pyrrolidinyl, piperidinyl, and morpholinyl (such as morpholino), piperazinyl) optionally substituted by 1-2 alkyls; preferably the heterocyclic group optionally substituted by —$NR_{11}R_{12}$ is a piperidinyl or a piperazinyl with their ring nitrogen atom linking to the rest of the compound, which preferably is substituted by the —$NR_{11}R_{12}$ group;

$R_6$ is hydrogen, halogen or $C_{1-4}$ alkoxy, preferably hydrogen; and $R_7$, $R_9$ and $R_{10}$ are H.

In one or more of embodiments of Formula IIIb:

$R_1$ is a $C_{1-6}$ alkyl, a heteroaryl optionally substituted by 1-3 substituents selected from the group consisting of halogen, $C_{1-4}$ alkyl and $C_{1-4}$ alkoxy, or a heterocyclic group optionally substituted by 1-2 substituents selected from the group consisting of $C_{1-6}$ alkyl, preferably $R_1$ is $C_{1-4}$ alkyl, tetrahydropyranyl optionally substituted by 1-2 $C_{1-6}$ alkyls, piperidinyl optionally substituted by 1-2 $C_{1-6}$ alkyls, morpholinyl optionally substituted by 1-2 $C_{1-6}$ alkyls, pyridyl optionally substituted by 1-2 substituents selected from the group consisting of halogen and $C_{1-4}$ alkoxy, or piperazinyl optionally substituted by 1-3 $C_{1-6}$ alkyls;

$R_2$ is $C_{1-6}$ alkyl, preferably $C_{1-4}$ alkyl, more preferably methyl;

$R_3$ is $C_{1-6}$ alkoxy optionally substituted by —$NR_{11}R_{12}$, —$NR_{11'}$—$C_{1-6}$ alkyl-$NR_{11'}R_{12'}$ or heterocyclic group optionally substituted by —$NR_{11}R_{12}$, wherein $R_{11'}$ and $R_{12'}$ are independently selected from the group consisting of H and $C_{1-4}$ alkyl, $R_{11}$ and $R_{12}$ are independently selected from hydrogen or $C_{1-6}$ alkyl or $R_{11}$ and $R_{12}$ together with N form 4 to 8-membered heterocyclic group (such as azetidinyl, pyrrolidinyl, piperidinyl, and morpholinyl (such as morpholino), piperazinyl) optionally substituted by 1-2 alkyls; preferably the heterocyclic group optionally substituted by —$NR_{11}R_{12}$ is a piperidinyl or a piperazinyl with their ring nitrogen atom linking to the rest of the compound, which preferably is substituted by the —$NR_{11}R_{12}$ group;

$R_6$ is hydrogen, halogen or $C_{1-4}$ alkoxy;

$R_7$, $R_9$ and $R_{10}$ are H; and $R_8$ is H, halogen, $C_{1-4}$ alkyl substituted by 1-4 halogen, or $C_{1-4}$ alkoxy.

In one or more of the foregoing embodiments, the preferred compound examples of Formula I, Formula II, Formula IIIa and Formula IIIb include but are not limited to:

N,N-dimethyl-3-(4-(1-(tetrahydro-2H-pyran-4-yl)imidazo[1,5-a]quinoxalin-8-yl)phenoxy)propan-1-amine (Example 1);

N,N-dimethyl-3-((5-(3-methyl-1-(tetrahydro-2H-pyran-4-yl)imidazo[1,5-a]quinoxalin-8-yl)pyridin-2-yl)oxy)propan-1-amine (Example 2);

N,N-dimethyl-3-(4-(3-methyl-1-(tetrahydro-2H-pyran-4-yl)imidazo[1,5-a]quinoxalin-8-yl)phenoxy)propan-1-amine (Example 3);

N,N-dimethyl-3-(2-fluoro-4-(3-methyl-1-(tetrahydro-2H-pyran-4-yl)imidazo[1,5-a]quinoxalin-8-yl)phenoxy)propan-1-amine (Example 4);

N,N-dimethyl-3-(4-(3-methyl-1-(tetrahydro-2H-pyran-4-yl)imidazo[1,5-a]quinoxalin-8-yl)-2-(trifluoromethyl)phenoxy)propan-1-amine (Example 5);

N,N-dimethyl-1-(2-fluoro-4-(3-methyl-1-(tetrahydro-2H-pyran-4-yl)imidazo[1,5-a]quinoxalin-8-yl)phenyl)piperidin-4-amine (Example 6);

N,N-dimethyl-1-(2-chloro-4-(3-methyl-1-(tetrahydro-2H-pyran-4-yl)imidazo[1,5-a]quinoxalin-8-yl)phenyl)piperidin-4-amine (Example 7);

N,N-dimethyl-1-(4-(3-methyl-1-(tetrahydro-2H-pyran-4-yl)imidazo[1,5-a]quinoxalin-8-yl)-2-(trifluoromethyl)phenyl)piperidin-1-amine (Example 8);

1-(4-(3-methyl-1-(tetrahydro-2H-pyran-4-yl)imidazo[1,5-a]quinoxalin-8-yl)-2-(trifluoromethyl)phenyl)piperidin-4-amine (Example 9);

N-methyl-1-(4-(3-methyl-1-(tetrahydro-2H-pyran-4-yl)imidazo[1,5-a]quinoxalin-8-yl)-2-(trifluoromethyl)phenyl)piperidin-4-amine (Example 10);

N-ethyl-1-(4-(3-methyl-1-(tetrahydro-2H-pyran-4-yl)imidazo[1,5-a]quinoxalin-8-yl)-2-(trifluoromethyl)phenyl)piperidin-4-amine (Example 11);

3-methyl-8-(6-(3-(piperidin-1yl)propoxy)pyridin-3yl)-1-(tetrahydro-2H-pyran-4-yl)imidazo[1,5-a]quinoxaline (Example 12);

8-(1,3-dimethyl-1H-pyrazol-4-yl)-3-methyl-1-(tetrahydro-2H-pyran-4-yl)imidazo[1,5-a]quinoxaline (Example 13);

N,N-dimethyl-3-((5-(3-methyl-1-morpholinylimidazo[1,5-a]quinoxalin-8-yl)pyridin-2-yl)oxy)propan-1-amine (Example 14);

N,N-dimethyl-3-((5-(1-((2S,6R)-2,6-dimethylmorpholino)-3-methylimidazo[1,5-a]quinoxalin-8-yl)pyridin-2-yl)oxy)propan-1-amine (Example 15);

N,N-dimethyl-3-((5-(3-methyl-1-(piperidin-1-yl)imidazo[1,5-a]quinoxalin-8-yl)pyridin-2-yl)oxy)propan-1-amine (Example 16);

N,N-dimethyl-3-((5-(3-methyl-1-(4-methylpiperazin-1-yl)imidazo[1,5-a]quinoxalin-8-yl)pyridin-2-yl)oxy)propan-1-amine (Example 17);

N,N-dimethyl-3-((5-(3-methyl-1-((3S,5R)-3,4,5-trimethylpiperazin-1-yl)imidazo[1,5-a]quinoxalin-8-yl)pyridin-2-yl)oxy)propan-1-amine (Example 18);

N,N-dimethyl-3-((5-(1-isopropyl-3-methylimidazo[1,5-a]quinoxalin-8-yl)pyridin-2-yl)oxy)propan-1-amine (Example 19);

N,N-dimethyl-3-(2-fluoro-4-(1-isopropyl-3-methylimidazo[1,5-a]quinoxalin-8-yl)phenoxy)propan-1-amine (Example 20);

N,N-dimethyl-3-(4-(1-isopropyl-3-methylimidazo[1,5-a]quinoxalin-8-yl)-2-(trifluoromethyl)phenoxy)propan-1-amine (Example 21);

1-isopropyl-3-methyl-8-(6-(3-(piperidin-1-yl)propoxy)pyridin-3yl)imidazo[1,5-a]quinoxaline (Example 22);

7-fluoro-1-isopropyl-3-methyl-8-(6-(3-(piperidin-1yl)propoxy)pyridin-3yl)imidazo[1,5-a]quinoxaline (Example 23);

N,N-dimethyl-1-(2-fluoro-4-(1-isopropyl-3-methylimidazo[1,5-a]quinoxalin-8-yl)phenyl)piperidin-4-amine (Example 24);

N,N-dimethyl-1-(2-chloro-4-(1-isopropyl-3-methylimidazo[1,5-a]quinoxalin-8-yl)phenyl)piperidin-4-amine (Example 25);

N,N-dimethyl-1-(4-(1-isopropyl-3-methylimidazo[1,5-a]quinoxalin-8-yl)-2-(trifluoromethyl)phenyl)piperidin-4-amine (Example 26);

1-(4-(1-isopropyl-3-methylimidazo[1,5-a]quinoxalin-8-yl)-2-(trifluoromethyl)phenyl)piperidin-4-amine (Example 27);

N-methyl-1-(4-(1-isopropyl-3-methylimidazo[1,5-a]quinoxalin-8-yl)-2-(trifluoromethyl)phenyl)piperidin-4-amine (Example 28);

N-ethyl-1-(4-(1-isopropyl-3-methylimidazo[1,5-a]quinoxalin-8-yl)-2-(trifluoromethyl)phenyl)piperidin-4-amine (Example 29);

8-(1,3-dimethyl-4H-1$\lambda^4$-pyrazol-4-yl)-1-(3-fluoro-5-methoxypyridin-4-yl)-7-methoxy-3-methylimidazo[1,5-a]quinoxaline (Example 30);

(2S,6R)-4-(8-(6-(3-(azetidin-1-yl)propoxy)pyridin-3-yl)-3-methylimidazo[1,5-a]quinoxalin-1-yl)-2,6-dimethylmorpholine (Example 31);

(2S,6R)-2,6-dimethyl-4-(3-methyl-8-(6-(3-(pyrrolidin-1-yl)propoxy)pyridin-3-yl)imidazo[1,5-a]quinoxalin-1-yl)morpholine (Example 32);

(2S,6R)-2,6-dimethyl-4-(3-methyl-8-(6-(3-(piperidin-1-yl)propoxy)pyridin-3-yl)imidazo[1,5-a]quinoxalin-1-yl)morpholine (Example 33);

(2S,6R)-4-(8-(6-(2-(1H-imidazol-2-yl)ethoxy)pyridin-3-yl)-3-methylimidazo[1,5-a]quinoxalin-1-yl)-2,6-dimethylmorpholine (Example 34);

(2S,6R)-4-(8-(6-(2-(1H-imidazol-4-yl)ethoxy)pyridin-3-yl)-3-methylimidazo[1,5-a]quinoxalin-1-yl)-2,6-dimethylmorpholine (Example 35);

2-((5-(1-((2S,6R)-2,6-dimethylmorpholino)-3-methylimidazo[1,5-a]quinoxalin-8-yl)pyridin-2-yl)oxy)-N,N-dimethylethan-1-amine (Example 36);

3-((4-(1-((2S,6R)-2,6-dimethylmorpholino)-3-methylimidazo[1,5-a]quinoxalin-8-yl)-2-(trifluoromethyl)phenoxy)-N,N-dimethylpropan-1-amine (Example 37);

1-(5-(1-((2S,6R)-2,6-dimethylmorpholino)-3-methylimidazo[1,5-a]quinoxalin-8-yl)pyridin-2-yl)-N,N-dimethylpiperidin-4-amine (Example 38);

1-(4-(1-((2S,6R)-2,6-dimethylmorpholino)-3-methylimidazo[1,5-a]quinoxalin-8-yl)-2-fluorophenyl)-N,N-dimethylpiperidin-4-amine (Example 39);

1-(2-chloro-4-(1-((2S,6R)-2,6-dimethylmorpholino)-3-methylimidazo[1,5-a]quinoxalin-8-yl)phenyl)-N,N-dimethylpiperidin-4-amine (Example 40);

3-((5-(1-((2S,6R)-2,6-dimethylmorpholino)-3-ethylimidazo[1,5-a]quinoxalin-8-yl)pyridin-2-yl)oxy)-N,N-dimethylpropan-1-amine (Example 41);

3-((5-(1-((2S,6R)-2,6-dimethylmorpholino)-3-isopropylimidazo[1,5-a]quinoxalin-8-yl)pyridin-2-yl)oxy)-N,N-dimethylpropan-1-amine (Example 42);

3-((5-(1-((2S,6R)-2,6-dimethylmorpholino)imidazo[1,5-a]quinoxalin-8-yl)pyridin-2-yl)oxy)-N,N-dimethylpropan-1-amine (Example 43);

N,N-dimethyl-3-((5-(1-((3S,5R)-3,4,5-trimethylpiperazin-1-yl)imidazo[1,5-a]quinoxalin-8-yl)pyridin-2-yl)oxy)propan-1-amine (Example 44);

1-(5-(1-((2S,6R)-2,6-dimethylmorpholino)imidazo[1,5-a]quinoxalin-8-yl)pyridin-2-yl)-N,N-dimethylpiperidin-4-amine (Example 45);

$N^1$-(5-(1-((2S,6R)-2,6-dimethylmorpholino)-3-methylimidazo[1,5-a]quinoxalin-8-yl)pyridin-2-yl)-$N^3$,$N^3$-dimethylpropane-1,3-diamine (Example 46);

$N^1$-(5-(1-((2S,6R)-2,6-dimethylmorpholino)-3-methylimidazo[1,5-a]quinoxalin-8-yl)pyridin-2-yl)-$N^1$,$N^3$,$N^3$-trimethylpropane-1,3-diamine (Example 47);

1-(5-(1-((2S,6R)-2,6-dimethylmorpholino)-3-methylimidazo[1,5-a]quinoxalin-8-yl)pyridin-2-yl)piperidin-4-amine (Example 48);

1-(5-(1-((2S,6R)-2,6-dimethylmorpholino)-3-methylimidazo[1,5-a]quinoxalin-8-yl)pyridin-2-yl)-N-methylpiperidin-4-amine (Example 49);

1-(5-(1-((2S,6R)-2,6-dimethylmorpholino)-3-methylimidazo[1,5-a]quinoxalin-8-yl)pyridin-2-yl)-N-ethylpiperidin-4-amine (Example 50);

1-(5-(1-((2S,6R)-2,6-dimethylmorpholino)-3-methylimidazo[1,5-a]quinoxalin-8-yl)pyridin-2-yl)-N-isopropylpiperidin-4-amine (Example 51);

(2S,6R)-4-(8-(6-(4-(azetidin-1-yl)piperidin-1-yl)pyridin-3-yl)-3-methylimidazo[1,5-a]quinoxalin-1-yl)-2,6-dimethylmorpholine (Example 52);

3-((5-(1-((2S,6R)-2,6-dimethylmorpholino)-3-methylimidazo[1,5-a]quinoxalin-8-yl)pyridin-2-yl)oxy)propan-1-amine (Example 53);

3-((5-(1-((2S,6R)-2,6-dimethylmorpholino)-3-methylimidazo[1,5-a]quinoxalin-8-yl)pyridin-2-yl)oxy)-N-methylpropan-1-amine (Example 54);

3-((5-(1-((2S,6R)-2,6-dimethylmorpholino)-3-methylimidazo[1,5-a]quinoxalin-8-yl)pyridin-2-yl)oxy)-N-ethylpropan-1-amine (Example 55);

3-((5-(1-((2S,6R)-2,6-dimethylmorpholino)-3-methylimidazo[1,5-a]quinoxalin-8-yl)pyridin-2-yl)oxy)-N-ethyl-N-methylpropan-1-amine (Example 56);

3-((5-(1-((2S,6R)-2,6-dimethylmorpholino)-3-methylimidazo[1,5-a]quinoxalin-8-yl)pyridin-2-yl)oxy)-N,N-diethylpropan-1-amine (Example 57);

(2S,6R)-2,6-dimethyl-4-(3-methyl-8-(6-(3-morpholinopropoxy)pyridin-3-yl)imidazo[1,5-a]quinoxalin-1-yl)morpholine (Example 58);

(2S,6R)-2,6-dimethyl-4-(3-methyl-8-(6-(3-(4-methylpiperazin-1-yl)propoxy)pyridin-3-yl)imidazo[1,5-a]quinoxalin-1-yl)morpholine (Example 59);

(2S,6R)-2,6-dimethyl-4-(3-methyl-8-(6-(2-(4-methylpiperazin-1-yl)ethyl)pyridin-3-yl)imidazo[1,5-a]quinoxalin-1-yl)morpholine (Example 60);

3-(4-(1-((2S,6R)-2,6-dimethylmorpholino)-3-methylimidazo[1,5-a]quinoxalin-8-yl)-2-fluorophenoxy)-N,N-dimethylpropan-1-amine (Example 61);

3-(2-chloro-4-(1-((2S,6R)-2,6-dimethylmorpholino)-3-methylimidazo[1,5-a]quinoxalin-8-yl)phenoxy)-N,N-dimethylpropan-1-amine (Example 62);

1-(5-(1-((2R,6R)-2,6-dimethylmorpholino)-3-methylimidazo[1,5-a]quinoxalin-8-yl)pyridin-2-yl)-N,N-dimethylpiperidin-4-amine and 1-(5-(1-((2S,6S)-2,6-dimethylmorpholino)-3-methylimidazo[1,5-a]quinoxalin-8-yl)pyridin-2-yl)-N,N-dimethylpiperidin-4-amine (Example 63);

3-((5-(1-((2R,6R)-2,6-dimethylmorpholino)-3-methylimidazo[1,5-a]quinoxalin-8-yl)pyridin-2-yl)oxy)-N,N-dimethylpropan-1-amine and 3-((5-(1-((2S,6S)-2,6-dimethylmorpholino)-3-methylimidazo[1,5-a]quinoxalin-8-yl)pyridin-2-yl)oxy)-N,N-dimethylpropan-1-amine (Example 64);

or stereoisomers, tautomers, N-oxides, hydrates, isotope-substituted derivatives, solvates, or pharmaceutically acceptable salts thereof, or mixtures thereof or prodrugs thereof.

The term "hydrogen (H)" as employed herein includes its isotopes D and T.

The term "alkyl" as used herein refers to alkyl itself or a straight or branched chain radical of up to ten carbons. Useful alkyl groups include straight-chain or branched $C_{1-10}$ alkyl groups, preferably $C_{1-6}$ alkyl groups, such as $C_{1-4}$ alkyl groups. Typical $C_{1-10}$ alkyl groups include methyl, ethyl, propyl, isopropyl, butyl, sec butyl, tert-butyl, 3-pentyl, hexyl and octyl groups. Alkyl may be optionally substituted by one or more substituents as defined herein.

The term "alkenyl" as used herein refers to a straight or branched chain radical of usually 2-10 carbon atoms, having at least one double bond in the chain. Typical alkenyl groups include ethenyl, 1-propenyl, 2-propenyl, 2-methyl-1-propenyl, 1-butenyl and 2-butenyl.

The term "alkynyl" as used herein refers to a straight or branched chain radical of usually 2-10 carbon atoms, having at least one triple bond in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the above mentioned $C_{1-10}$ alkyl groups, such as $C_{1-6}$ alkoxy groups or $C_{1-4}$ alkoxy groups. The alkyl in the alkoxy may be optionally substituted. Substituents of alkoxy include, but are not limited to, halogen, morpholinyl, amino (including alkylamino and dialkylamino) and carboxyl (including ester groups thereof).

Useful alkylthio groups include sulfur substituted by the one of the above mentioned $C_{1-10}$alkyl groups, and the alkyl in the alkylthio may be optionally substituted. Also included are the sulfoxides and sulfones of such alkylthio groups.

Useful amino groups include —$NR_{11}R_{12}$, wherein $R_{11}$ and $R_{12}$ are independently hydrogen, optionally substituted $C_{1-10}$alkyl (such as $C_{1-6}$ alkyl or $C_{1-4}$ alkyl), optionally substituted cycloalkyl, aryl, optionally substituted heteroaryl or optionally substituted amino. Alternatively, $R_{11}$ and $R_{12}$ together with the N form an optionally substituted 4 to 8-membered heterocyclic group, such as piperidine, or $R_{11}$ and $R_{12}$ together with the N and other N or O form an optionally substituted 4 to 8-membered heterocyclic group, such as azetidinyl, pyrrolidinyl, piperazinyl or morpholinyl. The alkyl and heterocyclic group may be optionally substituted.

Useful halo or halogen groups include fluoro, chloro, bromo and iodo.

The term "aryl" as used herein refers to the aryl itself or as part of other groups, and is a monocyclic, bicyclic or tricyclic aromatic group containing 6 to 14 carbon atoms.

Useful aryl groups include $C_{6-14}$ aryl groups, preferably $C_{6-10}$ aryl groups. Typical $C_{6-14}$ aryl groups include phenyl, naphthyl, phenanthryl, anthracyl, indenyl, azulyl, biphenyl, biphenylene and fluorenyl.

The term "heteroaryl" as used herein refers to a group containing 5 to 14 ring atoms, with 6, 10 or 14 π electrons shared in the rings, and the contained ring atoms are carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl, including but not limited to 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinozalinyl, cinnolinyl, pteridinyl, carbazolyl, O-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-a]pyrimidinyl, pyrrolopyridyl such as pyrrolo[2,3-b]pyridyl, benzoisoxazolyl such as 1,2-benzoisoxazol-3-yl, benzimidazolyl, 2-hydroxyindolyl, thiadiazolyl and 2-oxobenzimidazolyl. Where the heteroaryl contains a nitrogen atom in a ring, such nitrogen atom may be in the form of an N-oxide, e.g., a pyridyl N-oxide, pyrazinyl N-oxide and pyrimidinyl N-oxide.

The term "carbocycle (carbocyclic group)" as used herein include cycloalkyl and partially saturated carbocyclic groups. Useful cycloalkyl is $C_{3-8}$ cycloalkyl. Typical cycloalkyl groups include cyclopropyl, cyclobutyl, cyclopentyl, cyclohexyl and cycloheptyl.

Useful partially saturated carbocyclic groups include cycloalkenyl groups, such as cyclopentenyl, cycloheptenyl and cyclooctenyl.

The term "heterocycle (heterocyclic group)" as used herein refers to a saturated or partially saturated 3-8 membered monocyclic, or 7-10 membered bicyclic ring system, which consists of carbon atoms and one to four heteroatoms selected from O, N, and S as ring atoms, wherein the nitrogen and sulfur heteroatoms can be optionally oxidized and the nitrogen can be optionally quaternized, and the term also includes any bicyclic ring system in which any of the above-defined heterocyclic rings is fused to a phenyl ring. The heterocycle can be substituted on carbon atom or nitrogen atom if the resulting compound is stable.

Useful saturated or partially saturated heterocyclic group include tetrahydrofuranyl, tetrahydropyranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl, which may be optionally substituted.

In this disclosure, unless otherwise described, when substituted, generally, the aryl, heteroaryl, carbocyclic group and heterocyclic group may be substituted by one or more (such as 1, 2, 3, or 4) substituents selected from the group consisting of: halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ chain alkenyl, $C_{2-6}$ alkynyl, $C_{6-10}$ aryl($C_{2-6}$)chain alkenyl, $C_{6-10}$ aryl ($C_{2-6}$)alkynyl, saturated and unsaturated heterocyclic group or heteroaryl, methylenedioxy, halogenated $C_{1-6}$ alkyl, $C_{6-10}$ aryl($C_{1-6}$)alkyl, $C_{1-6}$ hydroxyalkyl, ureido, thiol, azido, carbonyl, di($C_{1-10}$alkyl)amino, alkylsulfonyl, aminosulfonyl, dialkylaminosulfonyl, and alkylsulfiniyl, and the like, wherein the substituent itself may also be optionally substituted by corresponding substituent(s) as described herein.

In this disclosure, unless otherwise described, when substituted, generally, the alkyl, alkoxy, alkylthio, alkenyl, alkynyl and cycloalkyl may be substituted by one or more (such as 1, 2, 3, or 4) substituents selected from the group consisting of: halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ chain alkenyl, $C_{2-6}$ alkynyl, $C_{6-10}$ aryl($C_{2-6}$)chain alkenyl, $C_{6-10}$ aryl ($C_{2-6}$)alkynyl, saturated and unsaturated heterocyclic group or heteroaryl, methylenedioxy, $C_{1-6}$ halogenated alkyl, $C_{6-10}$ aryl($C_{1-6}$)alkyl, $C_{1-6}$ hydroxyalkyl, ureido, thiol, azido, carbonyl, di($C_{1-10}$alkyl)amino, alkylsulfonyl, aminosulfonyl, dialkylaminosulfonyl, and alkylsulfiniyl, and the like, wherein the substituent itself may also be optionally substituted by corresponding substituent(s) as described herein.

In preferred embodiments, unless otherwise described, when substituted, generally, the alkyl, alkoxy, alkylthio, alkenyl, alkynyl, cycloalkyl, carbonyl, carbocyclic group, aryl, heteroaryl and heterocyclic group may be substituted by one or more (such as 1, 2, 3, or 4) substituents selected from the group consisting of: halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ chain alkenyl, $C_{2-6}$ alkynyl, $C_{6-10}$ aryl($C_{2-6}$)chain alkenyl, $C_{6-10}$ aryl($C_{2-6}$)alkynyl, saturated and unsaturated heterocyclic group or heteroaryl.

It should be understood that, when the substituent is aryl or a substituent containing aryl, heteroaryl or a substituent containing heteroaryl, heterocyclic group or a substituent containing heterocyclic group, the number of the substituent is usually 1.

The term "arylalkyl" includes $C_{1-10}$ alkyl substituted by any one of the above $C_{6-14}$ aryl.

Preferred arylmethyl is benzyl, phenylethyl or naphthylmethyl.

The term "arylalkenyl" includes $C_{2-10}$ alkenyl substituted by any one of the above $C_{6-14}$ aryl.

The term "arylalkynyl" includes $C_{2-10}$ alkynyl substituted by any one of the above $C_{6-14}$ aryl.

The term "aryloxy" includes oxygen substituted by any one of the above $C_{6-14}$ aryl, and the aryl thereof can be optionally substituted. Useful aryloxy groups include phenoxy and 4-methylphenoxy.

The term "arylalkoxy" includes $C_{1-10}$ alkoxy substituted by any one of the above aryl, and the aryl thereof can be optionally substituted. Useful arylalkoxy groups include benzyloxy and phenylethoxy.

Useful halogenated alkyl groups include $C_{1-10}$ alkyl substituted by one or more halogens selected from fluorine, chlorine, bromine and iodine atoms, preferably $C_{1-6}$ alkyl substituted by one or more halogens selected from fluorine, chlorine, bromine and iodine atoms, such as fluoromethyl, difluoromethyl, trifluoromethyl, pentafluoroethyl, 1,1-difluoroethyl, chloromethyl, chlorofluoromethyl and trichloromethyl.

Useful acylamino (acylamido) groups are any $C_{1-6}$ acyl (alkanoyl) attached to an amino nitrogen, e.g., acetamino, propionamido, butanoylamido, pentanoylamido and hexanoylamido, as well as aryl-substituted $C_{1-6}$ acylamino groups, e.g., benzoylamido. Useful acyl groups include $C_{1-6}$ acyl groups, such as acetyl. The acyl itself may be optionally substituted, for example, by one or more (e.g., less than 6) substituents selected from aryl and halogen, wherein the aryl may be optionally substituted. For example, examples of substituted acylamino groups include chloroacetamide and pentafluorobenzoylamino.

Useful acyloxy groups are any $C_{1-6}$ acyl (alkanoyl) attached to an oxygen (—O—), e.g., formyloxy, acetoxy, propionyloxy, butanoyloxy, pentanoyloxy and hexanoyloxy. Similarly, the acyl in the acyloxy itself may be optionally substituted, for example, by one or more (e.g., less than 6) substituents selected from aryl and halogen.

Some of the compounds of the present disclosure may exist as stereoisomers including optical isomers. The disclosure includes all stereoisomers and the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts formed with bases, such as sodium hydroxy, tris(hydroxymethyl)aminomethane (TRIS, tromethamine) and N-methyl-glucamine.

Examples of prodrugs of the compounds of the disclosure include the simple esters of carboxylic acid-containing compounds (e.g., those obtained by condensation with a $C_{1-4}$ alcohol according to methods known in the art); esters of hydroxyl-containing compounds (e.g., those obtained by condensation with a $C_{1-4}$ carboxylic acid, $C_{3-6}$ diacid or anhydride thereof such as succinic anhydride and fumaric anhydride, according to methods known in the art); imines of amino-containing compounds (e.g., those obtained by condensation with a $C_{1-4}$ aldehyde or ketone according to methods known in the art); carbamate of amino-containing compounds, such as those described by Leu, et al. (*J. Med. Chem.* 1999, 42:3623-3628) and Greenwald, et al. (*J. Med. Chem.* 1999, 42:3657-3667); and acetals and ketals of alcohol-containing compounds (e.g., those obtained by condensation with chloromethyl methyl ether or chloromethyl ethyl ether according to methods known in the art).

The compounds of this disclosure may be prepared using methods known to those skilled in the art, or the novel methods of this disclosure. Specifically, the compounds of this disclosure with Formula I, Formula II, Formula IIIa or Formula IIIb can be prepared as illustrated by the exemplary reaction in Scheme 1. 7-Bromo-2-chloroquinoxaline, tributyl(1-ethoxyethylene)tin and bis(triphenylphosphine) palladium(II) chloride were reacted in toluene under heating to produce 1-(7-bromoquinoxalin-2-yl)-1-ethanone. Sodium cyanoborohydride, 1-(7-bromoquinoxalin-2-yl)-1-ethanone and ammonium acetate were reacted in methanol at room temperature to produce 1-(7-bromoquinoxalin-2-yl)ethan-1-amine. 1-(7-Bromoquinoxalin-2-yl)ethan-1-amine and tetrahydropyran-4-carboxylic acid were reacted in pyridine in the presence of 1-(3-dimethylaminopropyl)-3-ethylcarbodiimide hydrochloride and 1-hydroxybenzotriazole at room temperature to produce N-(1-(7-bromoquinoxalin-2-yl)ethyl) tetrahydro-2H-pyran-4-formamide. Trifluoromethanesulfonic anhydride, N-(1-(7-bromoquinoxalin-2-yl)ethyl)tetrahydro-2H-pyran-4-formamide and pyridine in dichloromethane were reacted at room temperature to produce 8-bromo-3-methyl-1-(tetrahydro-2H-pyran-4-yl)imidazo[1,5-a]quinoxaline. 8-Bromo-3-methyl-1-(tetrahydro-2H-pyran-4-yl)imidazo[1,5-a]quinoxaline and N,N-dimethyl-3-((5-(4,4,5,5-tetramethyl-1,3,2-dioxaborolan-2-yl)pyridin-2-yl)oxy)propan-1-amine were reacted under heating in a mixed solvent of 1,4-dioxane and water with the catalysis of [1,1'-bis(diphenylphosphine)ferrocene] palladium dichloride dichloromethane complex and cesium carbonate to produce the target compound N,N-dimethyl-3-((5-(3-methyl-1-(tetrahydro-2H-pyran-4-yl)imidazo[1,5-a] quinoxalin-8-yl)pyridin-2-yl)oxy)propan-1-amine.

Scheme 1

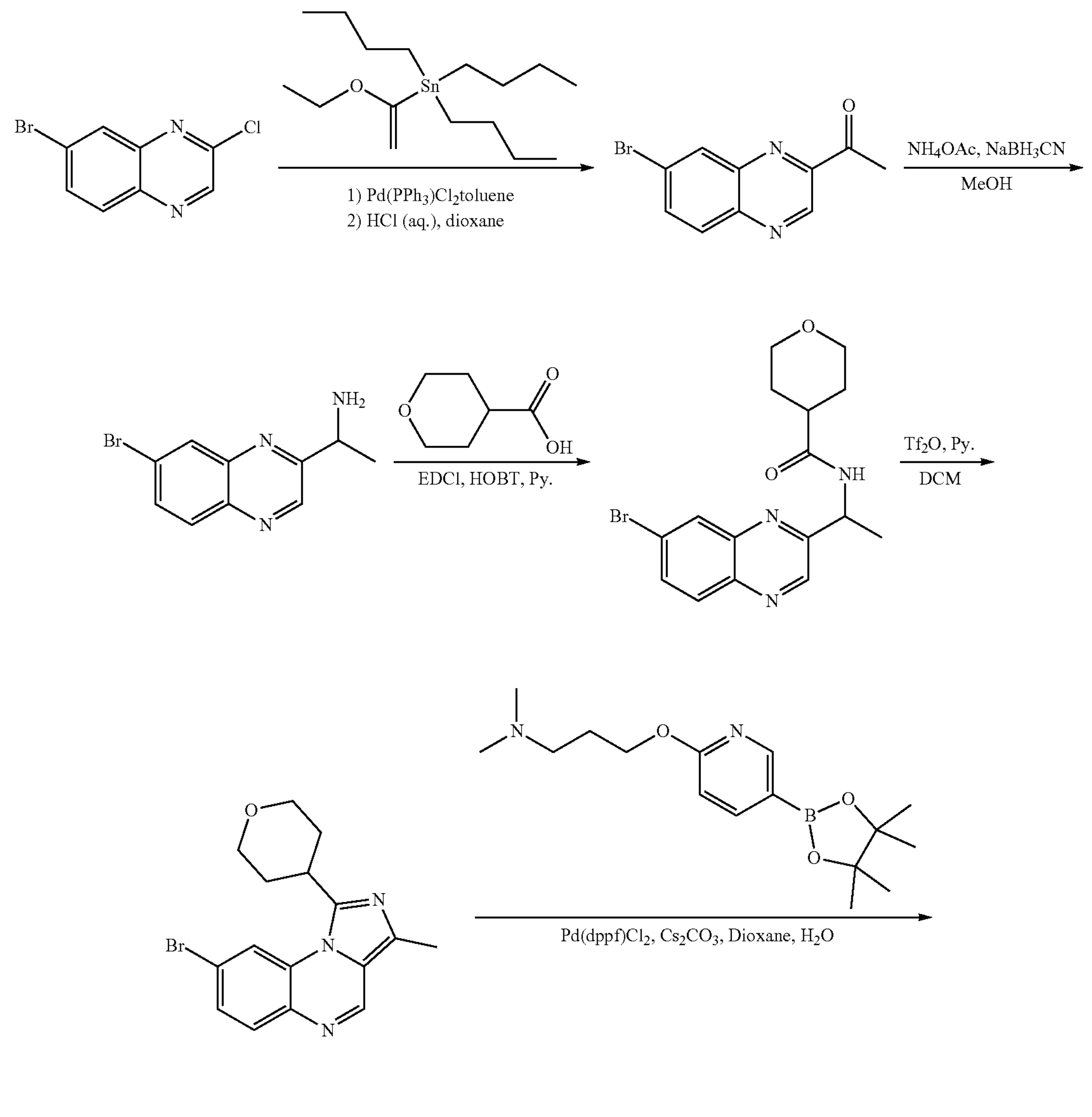

-continued

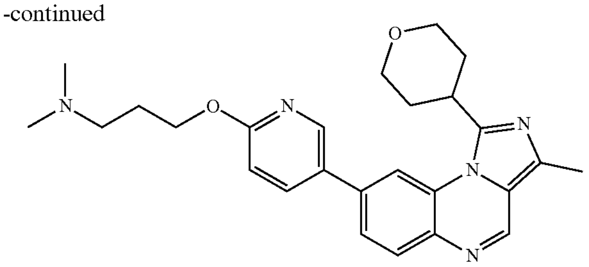

Other related compounds can be prepared similarly. For example, replacement of N,N-dimethyl-3-((5-(4,4,5,5-tetramethyl-1,3,2-dioxaborolan-2-yl)pyridin-2-yl)oxy)propan-1-amine with N,N-dimethyl-3-(4-(4,4,5,5-tetramethyl-1,3,2-dioxaborolan-2-yl)-2-(trifluoromethyl)phenoxy)propan-1-amine produced the target compound N,N-dimethyl-3-(4-(3-methyl-1-(tetrahydro-2H-pyran-4-yl)imidazo[1,5-a]quinoxalin-8-yl)-2-(trifluoromethyl)phenoxy)propan-1-amine. Replacement of N,N-dimethyl-3-((5-(4,4,5,5-tetramethyl-1,3,2-dioxaborolan-2-yl)pyridin-2-yl)oxy)propan-1-amine with 1-(2-fluoro-4-(4,4,5,5-tetramethyl-1,3,2-dioxaborolan-2-yl)phenyl)-N,N-dimethylpiperidin-4-amine produced the target compound N,N-dimethyl-1-(2-fluoro-4-(3-methyl-1-(tetrahydro-2H-pyran-4-yl)imidazo[1,5-a]quinoxalin-8-yl)phenyl)piperidin-4-amine. Replacement of N,N-dimethyl-3-((5-(4,4,5,5-tetramethyl-1,3,2-dioxaborolan-2-yl)pyridin-2-yl)oxy)propan-1-amine with (1,3-dimethyl-1H-pyrazol-4-yl)boronic acid produced the target compound 8-(1,3-dimethyl-1H-pyrazol-4-yl)-3-methyl-1-(tetrahydro-2H-pyran-4-yl)imidazo[1,5-a]quinoxaline. Replacement of tetrahydropyran-4-carboxylic acid with isobutyryl chloride produced the target compound 1-isopropyl-3-methyl-8-(6-(3-(piperidin-1-yl)propoxy)pyridin-3-yl)imidazo[1,5-a]quinoxaline. Replacement of 7-bromo-2-chloroquinoxaline with 7-bromo-2-chloro-6-fluoroquinoxaline produced the target compound 7-fluoro-1-isopropyl-3-methyl-8-(6-(3-(piperidin-1-yl)propoxy)pyridin-3-yl)imidazo[1,5-a]quinoxaline.

The compounds of this disclosure can be prepared as illustrated by the exemplary reaction in Scheme 2. 1-(7-Bromoquinoxalin-2-yl)ethan-1-amine, morpholine-4-carbonyl chloride and diisopropylethylamine (DIEA) were reacted in DCM at room temperature to produce N-(1-(7-bromoquinoxalin-2-yl)ethyl)morpholine-4-formamide. N-(1-(7-Bromoquinoxalin-2-yl)ethyl)morpholine-4-formamide and $POCl_3$ were reacted under heating to produce 4-(8-bromo-3-methylimidazo[1,5-a]quinoxalin-1-yl)morpholine. 4-(8-Bromo-3-methylimidazo[1,5-a]quinoxalin-1-yl)morpholine and N,N-dimethyl-3-((5-(4,4,5,5-tetramethyl-1,3,2-dioxaborolan-2-yl)pyridin-2-yl)oxy)propan-1-amine were reacted under heating in a mixed solvent of 1,4-dioxane and water with the catalysis of [1,1'-bis(diphenylphosphine)ferrocene]palladium dichloride dichloromethane complex and cesium carbonate to produce the target compound N,N-dimethyl-3-((5-(3-methyl-1-morpholinylimidazo[1,5-a]quinoxalin-8-yl)pyridin-2-yl)oxy)propan-1-amine.

Scheme 2

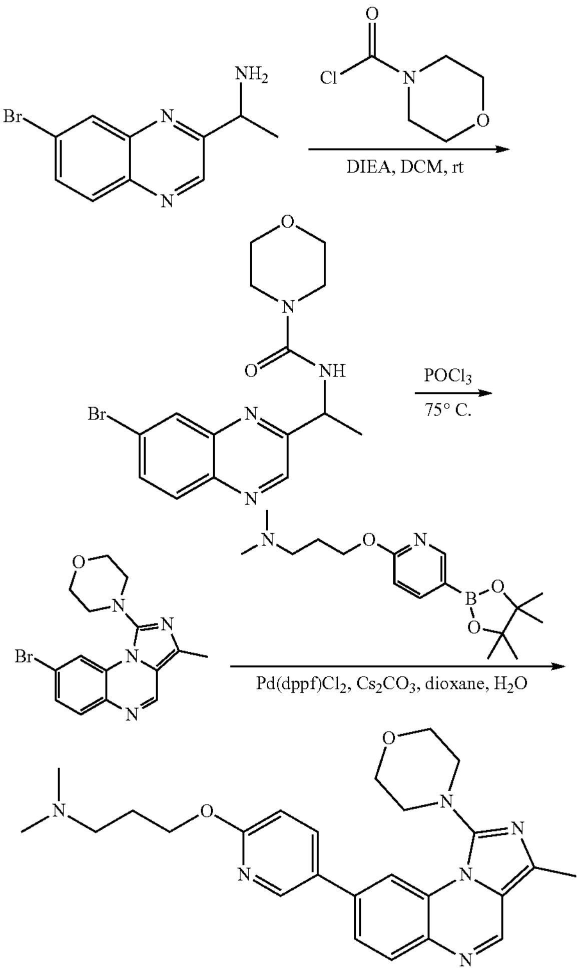

Other related compounds can be prepared similarly. For example, replacement of morpholine-4-carbonyl chloride with (2R,6S)-2,6-dimethylmorpholine-4-carbonyl chloride produced the target compound N,N-dimethyl-3-((5-(1-((2S,6R)-2,6-dimethylmorpholinyl)-3-methylimidazo[1,5-a]quinoxalin-8-yl)pyridin-2-yl)oxy)propan-1-amine. Replacement of morpholine-4-carbonyl chloride with (3R,5S)-3,4,5-trimethylpiperazine-1-carbonyl chloride produced the target compound N,N-dimethyl-3-((5-(3-methyl-1-((3S,5R)-3,4,5-trimethylpiperazin-1-yl)imidazo[1,5-a]quinoxalin-8-yl)pyridin-2-yl)oxy)propan-1-amine. Replacement of N,N-dimethyl-3-((5-(4,4,5,5-tetramethyl-1,3,2-dioxaborolan-2-yl)pyridin-2-yl)oxy)propan-1-amine with 2-(3-(piperidin-1-yl)propoxy)-5-(4,4,5,5-tetramethyl-1,3,2-dioxaborolan-2-yl)pyridin-2-yl)pyridine produced the target compound (2S,6R)-2,6-dimethyl-4-(3-methyl-8-(6-(3-(piperidin-1-yl)propoxy)pyridin-3-yl)imidazo[1,5-a]quinoxalin-1-yl)morpholine. Replacement of N,N-dimethyl-3-((5-(4,4,5,5-tetramethyl-1,3,2-dioxaborolan-2-yl)pyridin-2-yl)oxy)propan-1-amine with 1-(2-fluoro-4-(4,4,5,5-tetramethyl-1,3,2-dioxaborolan-2-yl)phenyl)-N,N-dimethylpiperidin-4-amine produced the target compound 1-(4-(1-((2S,6R)-2,6-dimethylmorpholinyl)-3-methylimidazo[1,5-a]quinoxalin-8-yl)-2-fluorophenyl)-N,N-dimethylpiperidin-4-amine.

The compounds of this disclosure can be prepared as illustrated by the exemplary reaction in Scheme 3.

propane-1,3-diamine with N-methyl-1-(6-(4,4,5,5-tetramethyl-1,3,2-dioxaborolan-2-yl)pyridin-3-yl)piperidin-4-amine produced the target compound 1-(5-(1-((2S,6R)-2,6-dimethylmorpholino)-3-methylimidazo[1,5-a]quinoxalin-8-yl)pyridin-2-yl)-N-methylpiperidin-4-amine. Replacement of $N^1,N^1$-dimethyl-$N^3$-(5-(4,4,5,5-tetramethyl-1,3,2-dioxaborolan-2-yl)pyridin-2-yl)propane-1,3-diamine with 1-methyl-4-(3-((5-(4,4,5,5-tetramethyl-1,3,2-dioxaborolan-2-yl)pyridin-2-yl)oxy)propyl)piperazine produced the target compound (2S,6R)-2,6-dimethyl-4-(3-methyl-8-(6-(3-(4-methylpiperazin-1-yl)propoxy)pyridin-3-yl)imidazo[1,5-a]quinoxalin-1-yl)morpholine. Replacement Scheme 3

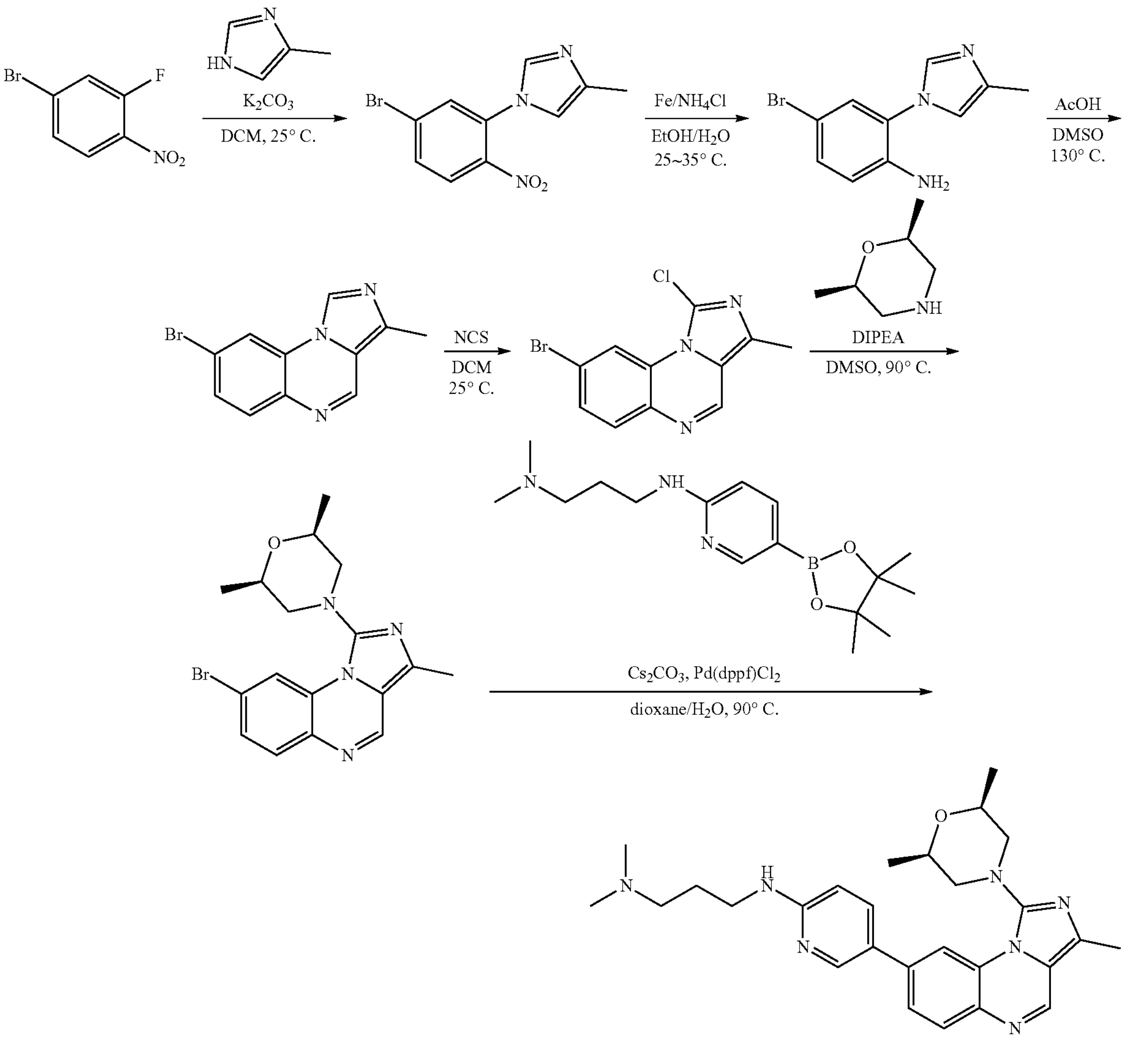

Other related compounds can be prepared similarly. For example, replacement of $N^1,N^1$-dimethyl-$N^3$-(5-(4,4,5,5-tetramethyl-1,3,2-dioxaborolan-2-yl)pyridin-2-yl)propane-1,3-diamine with 1-(6-(4,4,5,5-tetramethyl-1,3,2-dioxaborolan-2-yl)pyridin-3-yl)piperidin-4-amine produced the target compound 1-(5-(1-((2S,6R)-2,6-dimethylmorpholino)-3-methylimidazo[1,5-a]quinoxalin-8-yl)pyridin-2-yl)piperidin-4-amine. Replacement of $N^1,N^1$-dimethyl-$N^3$-(5-(4,4,5,5-tetramethyl-1,3,2-dioxaborolan-2-yl)pyridin-2-yl)

of (2S,6R)-2,6-dimethylmorpholine with (2R,6R)-2,6-dimethylmorpholine produced the target compounds 3-((5-(1-((2R,6R)-2,6-dimethylmorpholino)-3-methylimidazo[1,5-a]quinoxalin-8-yl)pyridin-2-yl)oxy)-N,N-dimethylpropan-1-amine and 3-((5-(1-((2S,6S)-2,6-dimethylmorpholino)-3-methylimidazo[1,5-a]quinoxalin-8-yl)pyridin-2-yl)oxy)-N,N-dimethylpropan-1-amine.

One important aspect of the present disclosure is the finding that the compounds of Formula I, Formula II, Formula IIIa and Formula IIIb are kinase inhibitors, especially ATM kinase inhibitors. Therefore, these compounds can be used to treat or prevent a variety of clinical conditions caused by DDR function defects or to treat or prevent diseases that benefit from inhibition of kinase activity. These diseases are also called DDR-mediated diseases or kinase-mediated diseases. Therefore, the disclosure provides uses of compounds of Formula I, Formula II, Formula IIIa and Formula IIIb in the preparation of medicaments for the treatment or prevention of clinical conditions caused by DDR function defects or of diseases that benefit from inhibition of kinase activity. Additionally, the applicant further discovers that the compounds of Formula I with $R_2$ being an optionally substituted alkyl, especially an optionally substituted $C_{1-4}$ alkyl, particularly methyl, especially those defined by Formula II, Formula IIIa and Formula IIIb, are highly active ATM kinase inhibitors. Therefore, in the preferred embodiments, the present disclosures particularly relate to use of these compounds with $R_2$ being a $C_{1-4}$ alkyl group to treat or prevent a variety of clinical conditions caused by DDR function defects or to treat or prevent diseases that benefit from inhibition of kinase activity, in the preparation of medicaments for the treatment or prevention of clinical conditions caused by DDR function defects or of diseases that benefit from inhibition of kinase activity, and pharmaceutical composition containing these compounds.

The present disclosure also includes methods for the treatment or prevention of DDR-mediated diseases or kinase-mediated diseases, comprising administering to an object in need an effective amount of the compound of Formula I, Formula II, Formula IIIa or Formula IIIb or a stereoisomer, a tautomer, a N-oxide, a hydrate, an isotope-substituted derivative, a solvate, or a pharmaceutically acceptable salt thereof, or a mixture thereof or prodrug thereof, or a pharmaceutical composition comprising an effective amount of the compound of Formula I, Formula II, Formula IIIa or Formula IIIb or a stereoisomer, a tautomer, a N-oxide, a hydrate, an isotope-substituted derivative, a solvate, or a pharmaceutically acceptable salt thereof, or a mixture thereof or a prodrug thereof.

In the disclosure, the clinical conditions caused by DDR function defects or diseases that benefit from inhibition of kinase activity, or DDR-mediated or kinase-mediated diseases include but are not limited to cancers, including but not limited to liver cancer, melanoma, Hodgkin's disease, non-Hodgkin's lymphoma, acute lymphocytic leukemia, chronic lymphocytic leukemia, multiple myeloma, neuroblastoma, breast cancer, ovarian cancer, lung cancer, Wilms tumor, cervical cancer, testicular cancer, soft tissue sarcoma, primary macroglobulinemia, bladder cancer, chronic myeloid leukemia, primary brain cancer, malignant melanoma, small cell lung cancer, gastric cancer, colon cancer, malignant pancreatic islet tumor, malignant carcinoid cancer, choriocarcinoma, mycosis fungoides, head and neck cancer, osteogenic sarcoma, pancreatic cancer, acute myeloid leukemia, hairy cell leukemia, rhabdomyosarcoma, Kaposi's sarcoma, urogenital tumors, thyroid cancer, esophageal cancer, malignant hypercalcemia, cervical hyperplasia, renal cell carcinoma, endometrial cancer, polycythemia vera, idiopathic thrombocythemia, adrenocortical carcinoma, skin cancer, prostate cancer and Huntington's disease. In the disclosure, the kinase includes ATM (ataxia-telangiectasia mutant gene) kinase; therefore, in some embodiments, the cancer described in the disclosure is an ATM kinase-mediated cancer, preferably a cancer benefit from inhibition of ATM kinase activity.

In practicing the therapeutic methods of the disclosure, effective amounts of pharmaceutical preparations are administered to a patient exhibiting one or more of these symptoms. The pharmaceutic preparation comprises therapeutically effective concentrations of the compound of Formula I, Formula II, Formula IIIa or Formula IIIb for oral, intravenous, local or topical application, for the treatment of cancer and other diseases. The amounts are effective to ameliorate or eliminate one or more symptoms. An effective amount of a compound for treating a particular disease is an amount that is sufficient to ameliorate or in some manner relieve symptoms associated with a disease. Such amount may be administered as a single dosage or may be administered according to an effective regimen. The amount may cure the disease but, typically, is administered in order to ameliorate symptoms of a disease. Typically, repeated administration is required to achieve the desired amelioration of symptom.

In another embodiment, there is provided a pharmaceutical composition comprising the compound of Formula I, Formula II, Formula IIIa or Formula IIIb or a stereoisomer, a tautomer, a N-oxide, a hydrate, an isotope-substituted derivative, a solvate, or a pharmaceutically acceptable salt thereof, or a mixture there of or a prodrug thereof as a kinase inhibitor, and a pharmaceutically acceptable carrier.

Another embodiment of the present disclosure is directed to a pharmaceutical composition effective to treat cancer, comprising the compound of Formula I, Formula II, Formula IIIa or Formula IIIb or a stereoisomer, a tautomer, a N-oxide, a hydrate, an isotope-substituted derivative, a solvate, or a pharmaceutically acceptable salt thereof, or a mixture there of or a prodrug thereof as a kinase inhibitor, in combination with at least one known anticancer agent or a pharmaceutically acceptable salt thereof. In particular, the compound herein can be combined with other anticancer agents related to the mechanism of DNA damage and repair, including PARP inhibitors Olaparib, Niraprib, Rucaparib, Talazoparib and Senaparib; HDAC inhibitors Volinota, Romididesin, Papiseta and Bailesta; and so on. And the compound herein can be combined with other anticancer agents related to cell division checkpoints, including Chk1/2 inhibitors, CDK4/6 inhibitors such as Palbociclib, ATR inhibitors, and so on. Other known anticancer agents which may be used for anticancer combination therapy include, but are not limited to alkylating agents, such as busulfan, melphalan, chlorambucil, cyclophosphamide, ifosfamide, temozolomide, bendamustine, cis-platin, mitomycin C, bleomycin and carboplatin; topoisomerase I inhibitors, such as camptothecin, irinotecan and topotecan; topoisomerase II inhibitors, such as doxorubicin, epirubicin, aclacinomycin, mitoxantrone, elliptinium and etoposide; RNA/DNA antimetabolites, such as 5-azacytidine, gemcitabine, 5-fluorouracil, capecitabine, and methotrexate; DNA antimetabolites, such as 5-fluoro-2'-deoxy-uridine, fludarabine, nelarabine, ara-C, pralatrexate, pemetrexed, hydroxyurea and thioguanine; antimitotic agent, such as colchicine, vinblastine, vincristine, vinorelbine, paclitaxel, ixabepilone, cabazitaxel and docetaxel; antibodies, such as mAb, panitumumab, necitumumab, nivolumab, pembrolizumab, ramucirumab, bevacizumab, pertuzumab, trastuzumab, cetuximab, obinutuzumab, ofatumumab, rituximab, alemtuzumab, ibritumomab, tositumomab, brentuximab, daratumumab, elotuzumab, T-DM1, ofatumumab, dinutuximab, blinatumomab, ipilimumab, avastin, herceptin and mabthera; kinase inhibitors, such as imatinib, gefitinib, erlotinib, osimertinib, afatinib, ceritinib, alectinib, crizotinib, erlotinib, lapatinib, sorafenib, regorafenib, vemurafenib, dabrafenib, aflibercept, sunitinib, nilotinib, dasatinib, bosutinib, ponatinib, ibrutinib, cabozantinib, lenvatinib, vandetanib, trametinib, cobimetinib, axitinib, temsirolimus, Idelalisib, pazopanib, Torisel and everolimus. Other known anticancer agents which may be used for anticancer combination therapy include tamoxifen, letrozole, fulvestrant, mitoguazone, octreotide, retinoic acid, arsenic, zoledronic acid, bortezomib, carfilzomib, Ixazomib, vismodegib, sonidegib, denosumab, thalidomide, lenalidomide, Venetoclax, Aldesleukin (recombinant human interleukin-2) and Sipueucel-T (prostate cancer treatment vaccine).

In practicing the methods of the present disclosure, the compound(s) of the disclosure may be administered together with at least one known anticancer agent in a unitary pharmaceutical composition. Alternatively, the compound(s) of the disclosure may be administered separately from at least one known anticancer agent. In one embodiment, the compound(s) of the disclosure and at least one known anticancer agent are administered substantially simultaneously, i.e. all compound(s) or agent(s) are administered at the same time or one after another, provided that the compound(s) or agent(s) reach therapeutic concentrations in the blood at the same time. In another embodiment, the compound(s) of the disclosure and at least one known anticancer agent are administered according to individual dosage regimens, provided that the compound(s) reach therapeutic concentrations in the blood.

Another embodiment of the present invention is a bioconjugate comprising the compound of the disclosure that can effectively inhibit tumors and act as a kinase inhibitor. The bioconjugate that can inhibit tumors comprises or consists of the compound of the disclosure and at least one known therapeutically useful antibody, such as trastuzumab or rituximab, or growth factor, such as EGF or FGF, or cytokine, such as IL-2 or IL-4, or any molecule that can bind to cell surface. The antibodies and other molecules could deliver the compound(s) described herein to the targets, making it an effective anticancer agent. The bioconjugates could also enhance the anticancer effects of the therapeutically useful antibodies, such as trastuzumab or rituximab.

Another embodiment of the present disclosure is directed to a pharmaceutical composition effective to inhibit tumor, comprising the compound of Formula I, Formula II, Formula IIIa or Formula IIIb, or a stereoisomer, a tautomer, a N-oxide, a hydrate, an isotope-substituted derivative, a solvate, or a pharmaceutically acceptable salt thereof, or a mixture thereof or a prodrug thereof as a kinase inhibitor, in combination with radiation therapy. In this embodiment, the compound(s) of the disclosure may be administered at the same time or at a different time as the radiation therapy.

Yet another embodiment of the present disclosure is directed to a pharmaceutical composition effective for post-surgical treatment of cancer, comprising the compound of Formula I, Formula II, Formula IIIa or Formula IIIb, or a stereoisomer, a tautomer, a N-oxide, a hydrate, an isotope-substituted derivative, a solvate, or a pharmaceutically acceptable salt thereof, or a mixture thereof or a prodrug thereof as a kinase inhibitor. The disclosure also relates to a method of surgically removing tumor and then treating the cancer of the mammal with the pharmaceutical composition of the disclosure.

Pharmaceutical compositions of the disclosure include all pharmaceutical preparations which contain the compounds of the present disclosure in an amount that is effective to achieve its intended purpose. While individual needs are different, the skill of the art could determination determine optimal amounts of each component in the pharmaceutical preparations. Typically, the compounds or the pharmaceutically acceptable salts thereof may be administered to mammals orally at a dose of about 0.0025 to 50 mg per kg body weight per day. Preferably, from approximately 0.01 mg/kg to approximately 10 mg/kg body weight is orally administered. If a known anticancer agent is also administered, it is administered in an amount that is effective to achieve its intended purpose. The optimal amounts of such known anticancer agents are well known to those skilled in the art.

The unit oral dose may comprise from approximately 0.01 to approximately 50 mg, preferably approximately 0.1 to approximately 10 mg of the compound of the disclosure. The unit dose may be administered one or more times, with one or more tablets daily, each containing from approximately 0.1 to approximately 50 mg, conveniently approximately 0.25 to 10 mg of the compound of the disclosure or solvates thereof.

In a topical formulation, the compound(s) of the disclosure may be present at a concentration of approximately 0.01 to 100 mg per gram of carrier.

The compound(s) of the disclosure may be administered as a raw chemical. The compounds of the disclosure may also be administered as part of a suitable pharmaceutical preparation containing pharmaceutically acceptable carriers (comprising excipients and auxiliaries). Such pharmaceutically acceptable carriers facilitate the manufacture of pharmaceutically acceptable preparations from the compound(s). Preferably, the pharmaceutical preparations, particularly oral preparations and those used for the preferred administration routes, such as tablets, dragees, and capsules, as well as solutions suitable for injection or oral administration, contain from approximately 0.01% to 99%, preferably from approximately 0.25% to 75% of active compound(s), together with excipient(s).

Also included within the scope of the present disclosure are the non-toxic pharmaceutically acceptable salts of the compound(s) of the present disclosure. Acid addition salts are formed by mixing a solution of the compound(s) of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane, N-methylglucamine and the like.

The pharmaceutical preparations of the disclosure may be administered to any mammal, so long as they may experience the therapeutic effects of the compound(s) of the disclosure. Foremost among such mammals are humans and veterinary animals, although the disclosure is not intended to be so limited.

The pharmaceutical preparations of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively or additionally, administration may be by oral route. The dosage administered will be dependent upon the age, health, and weight of the subject, the combined therapy, frequency of treatment, and the desired therapeutic efficacy.

The pharmaceutical preparations of the present disclosure can be manufactured in a known manner, e.g., by conventional mixing, granulating, dragee-making, dissolving, or lyophilizing. Pharmaceutical preparations for oral use may be obtained by combining the active compounds with solid excipient(s), optionally grinding the resulting mixture, adding suitable auxiliaries if desired or necessary, processing the mixture of granules, thereby obtaining tablets or dragee cores.

Suitable excipients are, in particular, fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, including maize starch, wheat starch, rice starch, potato starch, gelatin, tragacanth, methylcellulose, hydroxypropylmethylcellulose, sodium carboxymethylcellulose, and/or polyvinyl pyrrolidone. If desired, disintegrating agents may be added, such as the above-mentioned starches and carboxymethyl-starch, cross-linked polyvinyl pyrrolidone, agar, or alginic acid or a salt thereof, such as sodium alginate. Auxiliaries are, in particular, flow-regulating agents and lubricants, e.g., silica, talc, stearic acid or salts thereof, such as magnesium stearate or calcium stearate, and/or polyethylene glycol. If desired, dragee cores can be provided with suitable coatings against gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings against gastric juices, solutions of suitable cellulose preparations, such as acetylcellulose phthalate or hydroxypropylmethylcellulose phthalate, are used. Dyes or pigments may be added to the tablets or dragee coatings, e.g., a combination for identification or to characterize a dose of active compound(s).

Other pharmaceutical preparations, which may be used orally, include push-fit capsules made of gelatin, as well as soft sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate; and stabilizers. In soft capsules, the active compound(s) are preferably dissolved or suspended in suitable liquids, such as fatty oils or liquid paraffin. In addition, in which stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, suspension stabilizers may also be contained.

In accordance with one aspect of the present disclosure, compounds of the disclosure are provided in topical and parenteral formulations and are used for the treatment of skin cancer.

The topical formulations of this disclosure can be formulated as oils, creams, lotions, ointments and the like by suitable carriers. Suitable carriers include vegetable or mineral oils, white petrolatum (white soft paraffin), branched chain fats or oils, animal fats and high molecular weight alcohol (greater than $C_{12}$). Preferred carriers are those in which the active ingredient(s) are soluble. Emulsifiers, stabilizers, humectants and antioxidants may also be included, as well as agents imparting color or fragrance, if desired. Additionally, transdermal penetration enhancers may be included in these topical formulations. Examples of such enhancers can be found in U.S. Pat. Nos. 3,989,816 and 4,444,762.

Creams are preferably formulated from a mixture of mineral oil, self-emulsifying beeswax and water, which is mixed with the active ingredient(s), dissolved in a small amount of an oil, such as almond oil. A typical example of such a cream is one which includes approximately 40 parts water, approximately 20 parts beeswax, approximately 40 parts mineral oil and approximately 1 part almond oil.

Ointments may be formulated by mixing a solution of the active ingredient(s) in a vegetable oil, such as almond oil, with warm soft paraffin and allowing the mixture to cool. A typical example of such ointments is one which includes approximately 30% by weight of almond oil and approximately 70% by weight of white soft paraffin.

The following examples are illustrative, but not limiting, of the methods and preparations of the present disclosure. Other suitable modifications and adaptations of various conditions and parameters normally encountered in clinical therapy and which are obvious to those skilled in the art are within the spirit and scope of the disclosure.

Example

General Remarks

All reagents were of commercial quality. Solvents were dried and purified by standard methods. Mass spectrum analyses were recorded on a Platform II (Agilent 6110) single quadrupole mass spectrometer equipped with an electrospray interface. $^{1}$H NMR spectra was recorded at 400 MHz, on a Brucker Ascend 400 apparatus. Chemical shifts were recorded in ppm from low-field relative to internal TMS (0.00 ppm), and J coupling constants were reported in hertz (Hz).

Example 1

N,N-dimethyl-3-(4-(1-(tetrahydro-2H-pyran-4-yl)imidazo[1,5-a]quinoxalin-8-yl)phenoxy)propan-1-amine

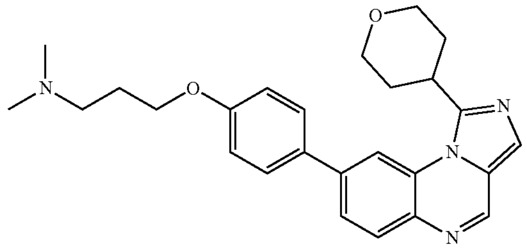 [SMILES: CN(C)CCCOc1ccc(-c2ccc3ncc4cnc(C5CCOCC5)n4c3c2)cc1]

a) Preparation of 2-hydroxy-7-bromoquinoxaline: 2-hydroxyquinoxaline (10 g, 68.5 mmol) was dissolved in acetic acid (500 mL), and liquid bromine (3.62 mL, 70.6 mmol) was slowly added dropwise at 10° C. After the addition, the reaction solution was reacted under stirring at room temperature for 3 hours, then the reaction mixture was cooled to 0° C., water (500 mL) was added, and stirring was continued for 30 minutes. The reaction mixture was filtered, the filter cake was washed with water (500 mL), and the solid was dried to obtain the target product (13.5 g, 88% yield, yellow solid). LC-MS (ESI): m/z $(M+H)^+/(M+2+H)^+$ 225.1/227.1.

b) Preparation of 2-chloro-7-bromoquinoxaline: 2-hydroxy-7-bromoquinoxaline (6 g, 26.7 mmol) was dissolved in phosphorus oxychloride (60 mL). Under the protection of nitrogen, the reaction solution was reacted under stirring at 100° C. for 2 hours. The reaction mixture was cooled to room temperature, the solvent was removed under reduced pressure to obtain a crude product, and then the crude product was extracted and separated with ethyl acetate (100 mL). The organic phase was washed with saturated sodium bicarbonate aqueous solution and saturated brine, dried with anhydrous sodium sulfate, filtered, and concentrated under reduced pressure to obtain the target product (6.23 g, 96% yield, light yellow solid). LC-MS (ESI): m/z $(M+H)^+/(M+2+H)^+$243.0/245.1.

c) Preparation of 7-bromo-2-methylquinoxaline: 2-chloro-7-bromoquinoxaline (4.7 g, 19.3 mmol) was dissolved in anhydrous tetrahydrofuran (50 mL), ferric acetylacetonate was added, and the reaction solution was cooled to 0° C. Methylmagnesium chloride (7 mL, 3 mol/L tetrahydrofuran solution) was slowly added into the reaction solution with a constant pressure dropping funnel. After dropping, the reaction was continued stirring at 0° C. for 5 hours. Then the reaction solution was slowly poured into saturated ammonium chloride aqueous solution to quench the reaction. After most tetrahydrofuran was removed under reduced pressure, the mixture was extracted and separated with ethyl acetate (40 mL×2). The organic phase was washed with saturated brine, dried with anhydrous sodium sulfate, filtered, and concentrated under reduced pressure to obtain a crude product. The crude product was isolated and purified by column chromatography (silica gel, ethyl acetate: petroleum ether=0-40% as eluent) to obtain the target product (3.27 g, 76% yield, white solid). LC-MS (ESI): m/z $(M+H)^+/(M+2+H)^+$ 223.1/225.1.

d) Preparation of 7-bromo-2-iodomethylquinoxaline: 7-bromo-2-methylquinoxaline (3.27 g, 14.66 mmol) was dissolved in acetonitrile, copper sulfate pentahydrate solid and iodine were added successively, and the reaction solution was reacted under stirring at 70° C. for 3 hours under the protection of nitrogen. After the reaction liquid was cooled to room temperature, the solvent was removed under reduced pressure, and then the mixture was extracted and separated with ethyl acetate (100 mL). The organic phase was washed with saturated sodium sulfite aqueous solution and saturated brine, dried with anhydrous sodium sulfate, filtered and concentrated under reduced pressure to obtain a crude product. The crude product was isolated and purified by column chromatography (silica gel, ethyl acetate: petroleum ether=0-30% as eluent) to obtain the target product (2.6 g, 50% yield, light yellow solid). LC-MS (ESI): m/z $(M+H)^+/(M+2+H)^+$ 348.9/350.9.

e) Preparation of 7-bromo-2-azidomethylquinoxaline: 7-bromo-2-iodomethylquinoxaline (956 mg, 2.74 mmol) was dissolved in anhydrous N,N-dimethylformamide (10 mL), sodium azide (196 mg, 3.01 mmol) was added thereto, and the reaction solution was reacted under stirring at room temperature for 11 hours. Then the reaction solution was added with 50 mL water, and extracted and separated with ethyl acetate (30 mL). The organic phase was washed with saturated brine for 3 times, dried with anhydrous sodium sulfate, filtered, and concentrated under reduced pressure to obtain a crude product. The crude product was isolated and purified by column chromatography (silica gel, ethyl acetate: petroleum ether=0-30% as eluent) to obtain the target product (820 mg, crude product, yellow solid). LC-MS (ESI): m/z $(M+H)^+/(M+2+H)^+$ 264.1/266.1.

f) Preparation of (7-bromoquinoxalin-2-yl)methylamine: 7-bromo-2-azidomethylquinoxaline (651 mg, 2.47 mmol) was dissolved in a mixed solution of tetrahydrofuran (8 mL) and water (4 mL), and triphenylphosphine (777 mg, 2.96 mmol) was added. Under the protection of nitrogen, the reaction solution was reacted under stirring at room temperature for 12 hours. The pH value of the reaction solution was adjusted to 1-3 with 1 mol/L hydrochloric acid aqueous solution. The mixture was extracted and separated with ethyl acetate (20 mL). The aqueous phase was collected, and then the pH of the aqueous phase was adjusted to 8 with saturated sodium bicarbonate solution. The mixture was extracted and separated with dichloromethane (20 mL×2). The organic phase was collected, dried with anhydrous sodium sulfate and filtered, and the solvent was removed under reduced pressure to obtain a crude product. The crude product was directly used in the next reaction (400 mg, crude product, brown solid). LC-MS (ESI): m/z $(M+H)^+/(M+2+H)^+$ 238.1/240.1.

g) Preparation of N-((7-bromoquinoxalin-2-yl)methyl) tetrahydro-2H-pyran-4-formamide: (7-bromoquinoxalin-2-yl)methylamine (400 mg, crude product, 1.68 mmol) was dissolved in N,N-dimethylformamide (8 mL), and N,N-diisopropylethylamine (0.88 ml, 5.04 mmol) and tetrahydropyran-4-carboxylic acid (262 mg, 2.02 mmol) were added successively. Under the protection of nitrogen, the reaction solution was reacted under stirring at 80° C. for 2 hours. After the reaction solution was cooled to room temperature, 40 mL of water was added, and the mixture was extracted and separated with ethyl acetate (30 mL×2). The organic phase was washed twice with saturated brine, dried with anhydrous sodium sulfate, and filtered, and the solvent was removed under reduced pressure to obtain a crude product. The crude product was isolated and purified by column chromatography (silica gel, methanol: dichloromethane=0-20%) to obtain the target product (275 mg, 46% yield, yellow solid). LC-MS (ESI): m/z $(M+H)^+/(M+2+H)^+$ 350.1/352.1.

h) Preparation of 8-bromo-1-(tetrahydro-2H-pyran-4-yl) imidazo[1,5-a]quinoxaline: N-((7-bromoquinoxalin-2-yl) methyl)tetrahydro-2H-pyran-4-formamide (210 mg, 0.60 mmol) was dissolved in a mixed solution of N,N-dimethylformamide (1 mL) and ethyl acetate (6 mL) and cooled to 0° C. Phosphorus oxychloride (410 mg, 3.6 mmol) was slowly added dropwise thereto. After dropping, the reaction mixture was heated to room temperature and stirred for 2 hours. Then, the reaction solution was slowly added dropwise to saturated sodium bicarbonate aqueous solution, and the pH value was kept above 8. The solution was extracted and separated with ethyl acetate (20 mL×2). The organic phase was washed twice with saturated brine, and dried with anhydrous sodium sulfate, and the solvent was removed by filtration to obtain a crude product. The crude product was isolated and purified by column chromatography (silica gel, methanol: dichloromethane=0-15%) to obtain the target product (68 mg, crude product, yellow solid). LC-MS (ESI): m/z $(M+H)^+/(M+2+H)^+$ 332.1/334.1.

i) Preparation of N,N-dimethyl-3-(4-(1-(tetrahydro-2H-pyran-4-yl)imidazo[1,5-a]quinoxalin-8-yl)phenoxy)propan-1-amine: 8-bromo-1-(tetrahydro-2H-pyran-4-yl)imidazo[1,5-a]quinoxaline (68 mg, crude product, 0.20 mmol) was dissolved in a mixed solution of dioxane and water (1.6 mL/0.4 mL), N,N-dimethyl-3-(4-(4,4,5,5-tetramethyl-1,3,2- dioxaborolan-2-yl)phenoxy)propan-1-amine (125 mg, 0.41 mmol), 1,1'-bis(diphenylphosphino)ferrocenedichloropalladium(II) (15 mg, 0.02 mmol) and cesium carbonate (200 mg, 0.61 mmol) were added thereto successively, and the reaction mixture was reacted under stirring at 100° C. for 1 hour under the protection of nitrogen. When the reaction solution was cooled to room temperature, the solvent was removed under reduced pressure to obtain a crude product. The crude product was isolated and purified by column chromatography (silica gel, methanol: dichloromethane=0-15%) and then further isolated and purified by preparative liquid chromatography (C18 column, 0-100% acetonitrile/water as mobile phase) to obtain the target compound (6 mg, 7% yield, yellow solid). LC-MS (ESI): $(M+H)^+$ 431.30. $^1$H NMR (400 MHz, DMSO-$d_6$): δ 8.96 (s, 1H), 8.30-8.27 (m, 1H), 7.99-7.95 (m, 1H), 7.88-7.84 (m, 2H), 7.77-7.71 (m, 2H), 7.15-7.10 (m, 2H), 4.11-4.01 (m, 5H), 3.68-3.62 (m, 2H), 2.39 (t, J=7.1 Hz, 2H), 2.17 (s, 6H), 2.13-2.08 (m, 2H), 2.04-1.96 (m, 2H), 1.92-1.85 (m, 2H).

Example 2

N,N-dimethyl-3-((5-(3-methyl-1-(tetrahydro-2H-pyran-4-yl)imidazo[1,5-a]quinoxalin-8-yl)pyridin-2-yl)oxy)propan-1-amine a) Preparation of 1-(7-bromoquinoxalin-2-yl)-1-ethanone: a toluene solution of 7-bromo-2-chloroquinoxaline (5 g, 20.53 mmol) and tributyl(1-ethoxyethylene)tin (9.27 g, 25.67 mmol, 8.66 ml) was vacuum pumped for 30 minutes. The reaction mixture was degassed and filled with nitrogen for 3 times. Bis(triphenylphosphine)palladium(II) chloride ($Pd(PPh_3)_2Cl_2$, 1.44 g, 2.05 mmol) was added. The reaction mixture was stirred in nitrogen atmosphere and heated at 80° C. for 12 hours. Stirring was continued at 80° C. for an additional 12 hours. The reaction mixture was evaporated to dryness, 1,4-dioxane (51 mL) was added thereto and suspended, 2 mol/L hydrochloric acid aqueous solution (51 mL) was added, and the resulting reaction mixture was stirred for 45 minutes. The residue was diluted with ethyl acetate (100 mL), the organic phases were combined, washed with brine (50 mL), dried over anhydrous sodium sulfate, filtered, and evaporated to dryness. The resulting crude product was purified by silica gel chromatography (petroleum ether:ethyl acetate=100/1 to 100/1.5) to obtain the target product (2.3 g, 4.61% yield, white solid). LC-MS (ESI): $(M+H)^+/(M+2+H)^+$ 250.8/252.7. $^1$H NMR (400 MHz, DMSO-$d_6$): δ 9.40 (s, 1H), 8.51-8.50 (m, 1H), 8.15-8.14 (m, 2H), 2.76 (s, 3H).

b) Preparation of 1-(7-bromoquinoxalin-2-yl)ethan-1-amine: Sodium cyanoborohydride ($NaBH_3CN$, 402.96 mg, 6.41 mmol) was added to a solution of 1-(7-bromoquinoxalin-2-yl)-1-ethanone (2.3 g, 9.16 mmol) and ammonium acetate ($NH_4OAc$, 7.06 g, 91.60 mmol) in methanol (50 mL). The reaction mixture was stirred at 25° C. for 12 hours. After removing methanol, 20 mL of water was added to the residue, then sodium hydroxide aqueous solution (w %=5%) was added, the pH of the resulting solution was adjusted to 13, and the mixture was extracted with dichloromethane (50 mL×2). The organic phases were combined, washed with brine (50 mL), dried over anhydrous sodium sulfate, filtered, and concentrated under reduced pressure to obtain a residue, which was purified by silica gel chromatography (petroleum ether:ethyl acetate=2/1, 1/1) to obtain the target product (0.7 g, 30.31% yield, brown oil). LC-MS (ESI): $(M-16+H)^+$ 235.0 (16: $NH_2$). $^1$H NMR (400 MHz, DMSO-$d_6$): δ 9.18 (s, 1H), 8.27 (d, J=2.4 Hz, 1H), 8.02 (d, J=8.8 Hz, 1H), 7.95 (dd, J=2.4, 8.8 Hz, 1H), 4.28-4.23 (m, 1H), 2.33-2.32 (m, 2H), 1.41 (d, J=6.8 Hz, 3H).

c) Preparation of N-(1-(7-bromoquinoxalin-2-yl)ethyl) tetrahydro-2H-pyran-4-formamide: A pyridine solution (4 mL) of 1-(7-bromoquinoxalin-2-yl)ethan-1-amine (0.4 g, 1.59 mmol) was added with 1-(3-dimethylaminopropyl)-3-ethylcarbodiimide hydrochloride (EDCI, 735.32 mg, 3.84 mmol) and 1-hydroxybenzotriazole (HOBT, 94.24 mg, 697.41 μmol), and then added with tetrahydropyran-4-carboxylic acid (226.91 mg, 1.74 mmol). The resulting mixture was stirred at 25° C. for 6 hours. In another reactor, a pyridine solution (3 mL) of 1-(7-bromoquinoxalin-2-yl) ethan-1-amine (0.3 g, 1.19 mmol), tetrahydropyran-4-carboxylic acid (170.18 mg, 1.31 mmol), EDCI (551.49 mg, 2.88 mmol) and HOBT (70.68 mg, 523.06 μmol) were added to the above solution, and the resulting mixture was stirred at 25° C. for 6 hours. The two reaction mixtures were diluted with water (45 mL) and extracted with ethyl acetate (15 mL×3). The organic layers were mixed, washed with brine (30 mL), dried over anhydrous sodium sulfate, filtered, and concentrated under reduced pressure to obtain a crude product. The crude product was crushed with methyl tert-butyl ether (5 mL) at 25° C. for 30 minutes to obtain the target compound (0.7 g, crude product, gray solid). LC-MS (ESI): $(M+H)^+/(M+2+H)^+$ 364.1/366.1. $^1$H NMR (400 MHz, DMSO-$d_6$): δ 8.95 (s, 1H), 8.54 (d, J=6.8 Hz, 1H), 8.28 (d, J=2 Hz, 1H), 8.04 (d, J=8.8 Hz, 1H), 7.97 (dd, J=2.1, 8.8 Hz, 1H), 5.17-5.13 (m, 1H), 3.86-3.84 (m, 2H), 3.31-3.27 (m, 2H), 1.63-1.56 (m, 3H), 1.51 (d, J=6.8 Hz, 3H).

d) Preparation of 8-bromo-3-methyl-1-(tetrahydro-2H-pyran-4-yl)imidazo[1,5-a]quinoxaline: Trifluoromethanesulfonic anhydride ($Tf_2O$, 684 mg, 2.42 mmol, 0.4 mL) was added to a dichloromethane (4 mL) solution of N-(1-(7-bromoquinoxalin-2-yl)ethyl)tetrahydro-2H-pyran-4-formamide (0.4 g, 1.10 mmol), the resulting mixture was stirred at 25° C. for 1 hour, then pyridine (588 mg, 7.43 mmol, 0.6 mL) was added, and the resulting mixture was stirred at 25° C. for 6 hours. The mixture was added with water (10 mL) at 0° C. and extracted with ethyl acetate (10 mL×3). The organic phases were combined, washed with brine (15 mL), dried with anhydrous sodium sulfate, filtered, and concentrated under reduced pressure to obtain a residue. The crude product was purified by silica gel chromatography (petroleum ether/EtOH=20/1) to obtain the target product (0.3 g, crude product, white solid). LC-MS (ESI): $(M+H)^+/(M+2+H)^+$ 346.1/348.1.

e) Preparation of N,N-dimethyl-3-((5-(3-methyl-1-(tetrahydro-2H-pyran-4-yl)imidazo[1,5-a]quinoxalin-8-yl)pyridin-2-yl)oxy)propan-1-amine: A 1,4-dioxane and water solution of 8-bromo-3-methyl-1-(tetrahydro-2H-pyran-4-yl) imidazo[1,5-a]quinoxaline (0.07 g, 202.18 μmol), N,N-dimethyl-3-((5-(4,4,5,5-tetramethyl-1,3,2-dioxaborolan-2-yl) pyridin-2-yl)oxy)propan-1-amine (87.29 mg, 285.08 μmol), [1,1'-bis(diphenylphosphino)ferrocene]dichloropalladium dichloromethane complex ($Pd(dppf)Cl_2$, 14.79 mg, 20.22 μmol) and cesium carbonate ($Cs_2CO_3$, 131.75 mg, 404.37 μmol) are vacuum pumped, the atmosphere was replaced with nitrogen for 3 times, and then the mixture was stirred at 90° C. in nitrogen atmosphere for 16 hours. The resulting reaction mixture was diluted with a mixed solvent of dichloromethane (10 mL) and methanol (1 mL), and filtered to remove insoluble substance to obtain a crude product, which was purified by preparative high performance liquid chromatography column (column: Waters Xbridge 150*25 mm*5 um; mobile phase (water (0.0500 ammonium hydroxide v/v)–ACN), B %: 280%-58%, 10 min) to obtain the target compound (21 mg, 16.40% yield, 98.600 purity, gray solid).

The following compounds of Examples 3-13 were prepared using methods similar to that described in Example 2.

| Example | Compound structure | MW | LC-MS (ESI) | $^1$H NMR, 400 MHz |
|---|---|---|---|---|
| 2 | 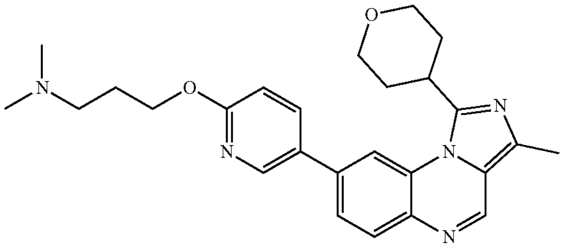 | 445.57 | (M + H)$^+$ 446.3 | DMSO-$d_6$: δ 8.96 (s, 1H), 8.61 (d, J = 2.4 Hz, 1H), 8.23 (d, J = 1.6 Hz, 1H), 8.15 (dd, J = 2.8, 8.8 Hz, 1H), 7.94 (d, J = 8.4 Hz, 1H), 7.85 (dd, J = 1.6, 8 Hz, 1H), 7.00 (d, J = 8.8 Hz, 1H), 4.36 (t, J = 13.2 Hz, 2H), 4.03-3.99 (m, 3H), 3.66-3.60 (m, 2H), 2.67 (s, 3H), 2.36-2.33 (m, 2H), 2.15 (s, 6H), 2.09-2.01 (m, 2H), 2.00-1.94 (m, 2H), 1.92-1.87 (m, 2H) |
| 3 | 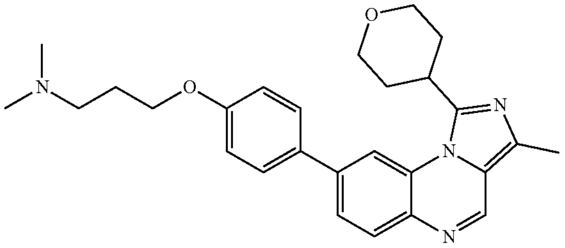 | 444.58 | (M + H)$^+$ 445.4 | $CDCl_3$: δ 8.75 (s, 1H), 8.15 (d, J = 2.0 Hz, 1H), 7.95 (d, J = 10.0 Hz, 1H), 7.70 (dd, J = 2.0 Hz, J = 10.0 Hz, 1H), 7.58 (d, J = 6.8 Hz, 2H), 7.05 (d, J = 6.4 Hz, 2H), 4.23-4.20 (m, 2H), 4.13 (t, J = 6.2 Hz, 2H), 3.81-3.73 (m, 1H), 3.72-3.66 (m, 2H), 2.69-2.67 (m, 2H), 2.63 (s, 3H), 2.42 (s, 6H), 2.27-2.17 (m, 2H), 2.16-2.10 (m, 4H) |
| 4 | 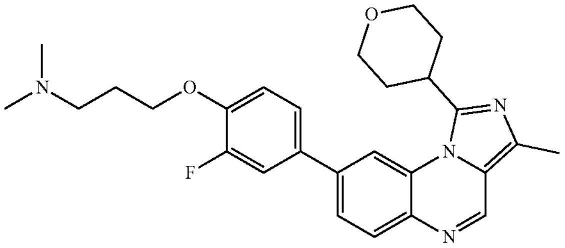 | 462.57 | (M + H)$^+$ 463.0 | $CDCl_3$: δ 8.76 (s, 1H), 8.13 (s, 1H), 8.13-8.00 (m, 1H), 7.68-7.67 (m, 1H), 7.66-7.62 (m, 1H), 7.36-7.30 (m, 2H), 7.16-7.14 (m, 2H), 4.24-4.18 (m, 4H), 3.76-3.66 (m, 3H), 2.63 (s, 3H), 2.57-2.51 (m, 2H), 2.27 (s, 6H), 2.26-2.20 (m, 4H), 2.09-2.05 (m, 2H) |
| 5 | 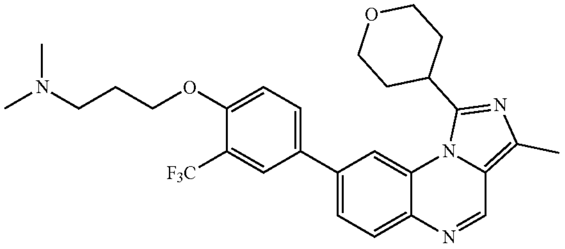 | 512.58 | (M + H)$^+$ 513.5 | $CDCl_3$: δ 8.74 (s, 1H), 8.15 (s, 1H), 8.02-8.00 (m, 1H), 7.84 (s, 1H), 7.77 (d, J = 9.2 Hz, 1H), 7.69 (d, J = 6.4 Hz, 1H),7.18 (d, J = 8.8 Hz, 1H), 4.23-4.20 (m, 4H), 3.72-3.65 (m, 3H), 2.64 (s, 3H), 2.53-2.51 (m, 2H), 2.29 (s, 8H), 2.20-2.16 (m, 2H), 2.04 (dd, J = 6.0, 13.2 Hz, 2H) |
| 6 | 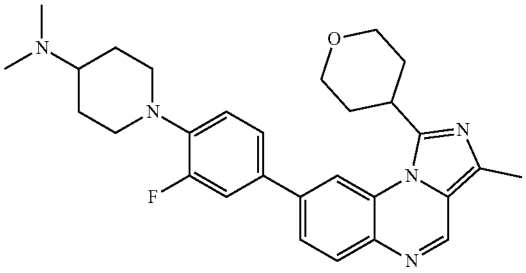 | 487.62 | (M + H)$^+$ 488.0 | $CDCl_3$: δ 8.75 (s, 1H), 8.15 (s, 1H), 7.98 (d, J = 8.4 Hz, 1H), 7.68 (dd, J = 2.0, 8.4 Hz, 1H), 7.36-7.30 (m, 2H), 4.22 (d, J = 12 Hz, 1H), 3.73-3.62 (m, 5H), 2.82-2.77 (m, 2H), 2.63 (s, 1H), 2.37 (s, 6H), 2.30-2.26 (m, 2H), 2.20-2.17 (m, 2H), 1.98 (d, J = 13.2 Hz, 2H), 1.79-1.75 (m, 2H) |

-continued

| Example | Compound structure | MW | LC-MS (ESI) | $^1$H NMR, 400 MHz |
|---|---|---|---|---|
| 7 | 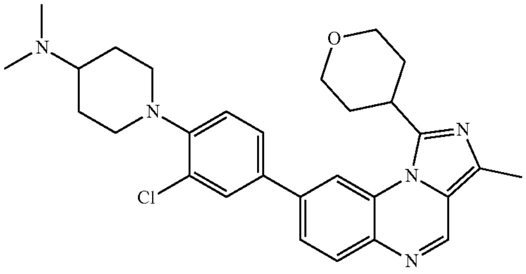 | 504.08 | $(M + H)^+$ 504.5 | DMSO-$d_6$: δ 8.96 (s, 1H), 8.23 (s, 1H), 7.94-7.92 (m, 1H), 7.87-7.82 (m, 2H), 7.74-7.71 (m, 1H), 7.33-7.28 (m, 1H) 4.06-4.03 (m, 3H), 3.69-3.33 (m, 2H), 3.40-3.31 (m, 2H), 2.75-2.72 (m, 2H), 2.55 (s, 3H), 2.12 (s, 6H), 2.08-2.02 (m, 2H), 1.97-1.92 (m, 2H), 1.90-1.88 (m, 2H), 1.62-1.58 (m, 2H) |
| 8 | 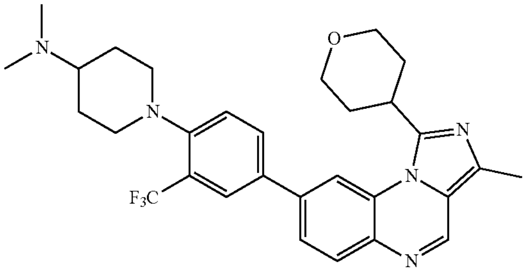 | 537.63 | $(M + H)^+$ 538.0 | $CDCl_3$: δ 8.78 (s, 1H), 8.18 (s, 1H), 8.02 (d, J = 8 Hz, 1H), 7.89 (s, 1H), 7.89-7.80 (m, 1H), 7.78-7.73 (m, 1H) 7.47 (d, J = 8.8 Hz, 1H), 4.42 (d, J = 13.2 Hz, 2H), 3.76-3.66 (m, 3H), 3.28-3.25 (m, 2H), 2.86-2.81 (m, 2H), 2.61 (s, 3H), 2.40 (s, 6H), 2.35-2.28 (m, 3H), 2.31-2.24 (m, 2H), 1.95 (s, 2H), 1.78 (d, J = 12 Hz, 2H) |
| 9 | 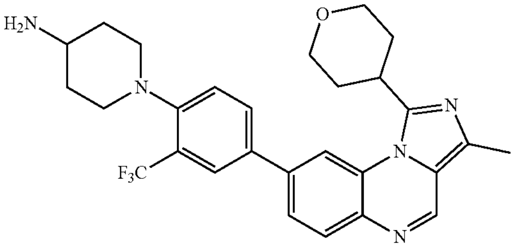 [SMILES: Cc1nc(C2CCOCC2)n2c1cnc1ccc(-c3ccc(N4CCC(N)CC4)c(C(F)(F)F)c3)cc12] | 509.58 | $(M + H)^+$ 510.5 | $CDCl_3$: δ 8.78 (s, 1H), 8.18 (s, 1H), 8.03 (d, J = 4 Hz, 1H), 7.89 (s, 1H),7.79 (d, J = 2 Hz, 1H), 7.73 (d, J = 4 Hz, 1H), 7.48 (m, J = 4 Hz, 1H), 4.24-4.21 (m, 2H), 3.71-3.65 (m, 3H), 3.21-3.18 (m, 2H), 2.88-2.82 (m, 3H), 2.64 (s, 3H), 2.31-2.27 (m, 2H), 2.20-2.17 (m, 2H), 1.98-1.95 (m, 2H), 1.65-1.56 (m, 2H), 1.31-1.27 (m, 2H) |
| 10 | 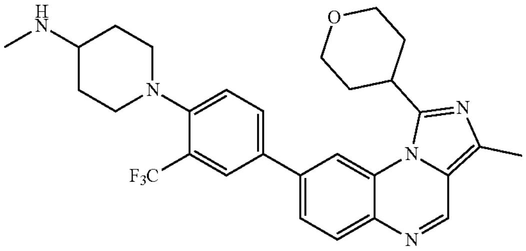 | 523.6 | $(M + H)^+$ 524.4 | $CDCl_3$: δ 9.69 (s, 1H), 8.86 (s, 1H), 8.17 (s, 1H), 8.17-8.10 (m, 1H), 7.88 (s, 1H), 7.82-7.80 (m, 1H), 7.74-7.56 (m, 1H), 4.22 (d, J = 6 Hz, 2H), 3.72-3.63 (m, 3H), 3.39-3.36 (m, 2H), 3.24 (brs, 1H), 2.94-2.89 (m, 2H), 2.79 (s, 3H), 2.67 (s, 3H), 2.38-2.23 (m, 4H), 2.29-2.16 (m, 4H) |
| 11 | 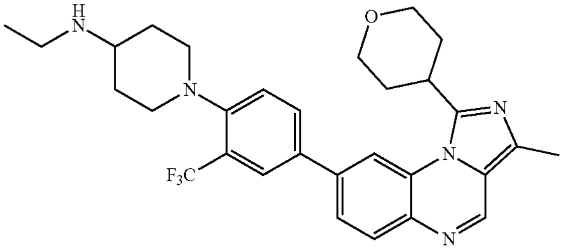 [SMILES: CCNC1CCN(c2ccc(-c3ccc4ncc5c(C)nc(C6CCOCC6)n5c4c3)cc2C(F)(F)F)CC1] | 537.63 | 538.5 | $CDCl_3$: δ 8.78 (s, 1H), 8.18 (s, 1H), 8.10 (d, J = 28 Hz, 1H) 8.01-7.89 (m, 1H), 7.88-7.77 (m, 1H), 7.72 (d, J = 4 Hz, 1H), 7.48-7.46 (m, 1H), 4.24-4.20 (m, 2H), 3.71-3.65 (m, 3H), 3.24-3.21 (d, J = 6 Hz, 2H), 2.88-2.79 (m, 4H), 2.77-2.75 (m, 1H), 2.64 (s, 3H), 2.28-2.27 (m, 2H), 2.20-2.21 (m, 2H), 2.10-2.02 (m, 2H), 1.67-1.51 (m, 2H), 1.21-1.18 (m, 3H) |
| 12 | 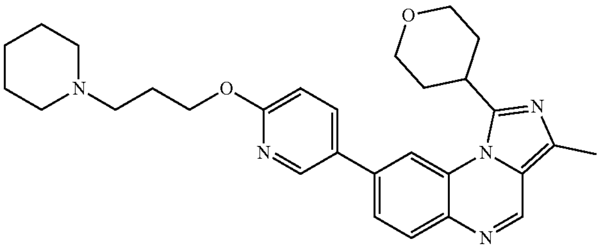 [SMILES: Cc1nc(C2CCOCC2)n2c1cnc1ccc(-c3ccc(OCCCN4CCCCC4)nc3)cc12] | 485.63 | 486.5 | $CDCl_3$: δ 8.77 (s, 1H), 8.44 (d, J = 2.4 Hz, 1H), 8.12 (d, J = 2 Hz, 1H), 8.01 (d, J = 8 Hz, 1H), 7.85-7.66 (m, 1H), 7.65 (d, J = 6.4 Hz, 1H), 6.89 (d, J = 8.8 Hz, 1H), 4.44-4.41 (m, 2H), 4.22-4.19 (m, 2H), 3.76-3.66 (m, 3H), 2.63 (s, 3H), 2.54-2.50 (m, 2H), 2.44 (s, 3H), 2.29-2.26 (m, 3H). 2.19-2.06 (m, 2H), 2.04-2.02 (m, 2H), 1.63-1.58 (m, 4H), 1.49-1.42 (m, 2H) |

-continued

| Example | Compound structure | MW | LC-MS (ESI) | $^1$H NMR, 400 MHz |
|---|---|---|---|---|
| 13 | 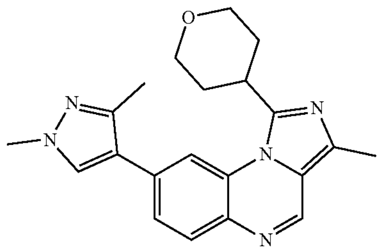 | 361.45 | 362.1 | $CDCl_3$: δ 8.74 (s, 1H), 7.98-7.95 (m, 2H), 7.53-7.50 (m, 2H), 4.20-4.18 (m, 2H), 3.95 (s, 3H), 3.73-3.62 (m, 3H), 2.63 (s, 3H), 2.50 (s, 3H), 2.33-2.23 (m, 2H), 2.14-2.11 (m, 2H) |

Example 14

N,N-dimethyl-3-((5-(3-methyl-1-morpholinylimidazo[1,5-a]quinoxalin-8-yl)pyridin-2-yl)oxy)propan-1-amine a) Preparation of N-(1-(7-bromoquinoxalin-2-yl)ethyl)morpholine-4-formamide: A dichloromethane (8 mL) solution of 1-(7-bromoquinoxalin-2-yl)ethan-1-amine (0.3 g, 2.01 mmol) was added with morpholine-4-formyl chloride (455.08 mg, 1.81 mmol) and DIEA (259.22 mg, 2.01 mmol). The mixture was stirred at 25° C. for 2 hours. The reaction mixture was diluted with water (50 mL) and extracted with dichloromethane (100 mL×2). The organic phases were combined, washed with brine (50 mL×2), dried over anhydrous sodium sulfate, filtered, and concentrated under reduced pressure to obtain the crude product (0.56 g, yellow oil, 76.4500 yield). LC-MS (ESI): $(M+H)^+$ 365.1.

b) Preparation of 4-(8-bromo-3-methylimidazo[1,5-a]quinoxalin-1-yl)morpholine: A mixture of N-(1-(7-bromoquinoxalin-2-yl)ethyl)morpholine-4-formamide (0.5 g, 1.37 mmol) and $POCl_3$ (8.25 g, 53.80 mmol) was heated to 75° C. and stirred at this temperature for 3 hours. At 0° C., 150 mL of water was added to quench the reaction, and then the pH of the mixture was adjusted to 7 with saturated sodium carbonate aqueous solution, and the mixture was extracted with EA (100 mL×2). The organic phases were collected and combined, dried over anhydrous sodium sulfate, and filtered, and the filtrate was concentrated under reduced pressure to obtain the target crude product (0.32 g, brown solid, 67.32% yield). LC-MS (ESI): $(M+H)^+$ 347.1.

c) Preparation of N,N-dimethyl-3-((5-(3-methyl-1-morpholinylimidazo[1,5-a]quinoxalin-8-yl)pyridin-2-yl)oxy)propan-1-amine: A solution of 4-(8-bromo-3-methylimidazo[1,5-a]quinoxalin-1-yl)morpholine (20.25 g, 720.03 μmol), N,N-dimethyl-3-((5-(4,4,5,5-tetramethyl-1,3,2-dioxaborolan-2-yl)pyridin-2-yl)oxy)propan-1-amine (440.95 mg, 1.44 mmol) in dioxane (15 mL) and water (1.5 mL) was added with $Cs_2CO_3$ (441.05 mg, 1.35 mmol) and [1,1'-bis(diphenylphosphine)ferrocene]palladium dichloride dichloromethane complex ($Pd(dppf)Cl_2$, 10.54 mg, 14.40 μmol). The mixture was heated to 90° C. and stirred for 2 hours. The reaction mixture was diluted with water (50 mL) and extracted with EA (50 mL×2). The organic phases were combined, washed with brine (25 mL×2), dried with anhydrous sodium sulfate, and filtered, and the filtrate was concentrated under reduced pressure to obtain a crude product, which was purified by preparative high performance liquid chromatography to obtain the target compound (23.29 mg, yellow oil, yield 5.53%).

The following compounds of Examples 15-45 were prepared using methods similar to that described in Example 2 or 14.

| Example | Compound structure | MW | LC-MS (ESI) | $^1$H NMR, 400 MHz |
|---|---|---|---|---|
| 14 | 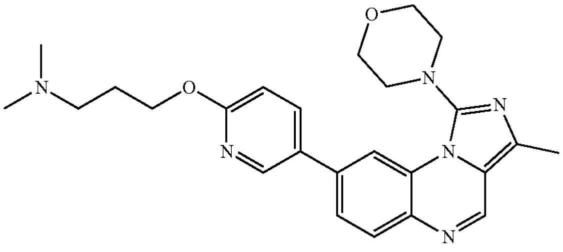 | 446.56 | 447.3 | $CDOD_3$: δ 7.41 (s, 1H), 7.34 (d, J = 2.00 Hz, 1H), 7.01 (d, J = 2.00 Hz, 1H), 6.57 (dd, J = 2.40, 8.40 Hz, 1H), 6.33 (d, J = 8.40 Hz, 1H), 6.25 (dd, J = 2.40, 8.40 Hz, 1H), 5.48 (d, J = 8.80 Hz, 1H), 2.97 (t, J = 6.00 Hz, 2H), 2.48-2.44 (m, 2H), 2.35-2.32 (m, 2H), 1.86-1.80 (m, 6H), 1.42 (s, 6H), 1.09 (s, 3H), 0.77-0.72 (m, 2H) |

-continued

| Example | Compound structure | MW | LC-MS (ESI) | $^1$H NMR, 400 MHz |
|---|---|---|---|---|
| 15 | 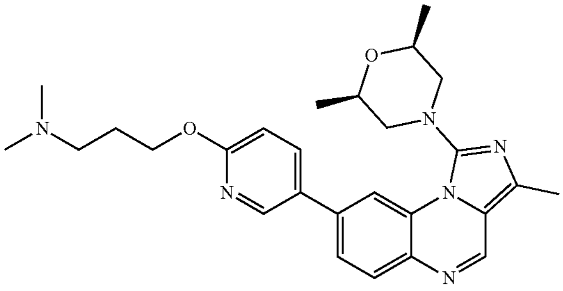 | 474.61 | 475.2 | $CDOD_3$: δ 9.09 (s, 1H), 8.68 (s, 1H), 8.43-8.38 (m, 1H), 8.10 (d, J = 7.6 Hz, 1H), 7.85 (dd, J = 2.3, 8.6 Hz, 1H), 7.71-7.63 (m, 1H), 6.91 (d, J = 8.6 Hz, 1H), 4.51 (t, J = 5.8 Hz, 2H), 4.00-3.96 (m, 2H), 3.46-3.24 (m, 4H), 2.94-2.88 (m, 8H), 2.68 (s, 3H), 2.48-2.25 (m, 2H), 1.28 (d, J = 4.6 Hz, 6H) |
| 16 | 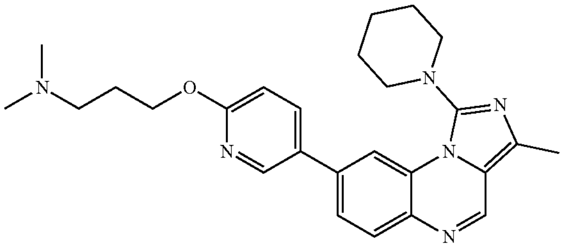 | 444.58 | $(M + H)^+$ 445.3 | $CDCl_3$: δ 8.83 (d, J = 2.0 Hz, H), 8.66 (s, 1H), 8.48-8.47 (m, H), 7.92-7.88 (m, 2H), 7.58 (dd, J = 2, 8.4 Hz, 1H), 6.89 (d, J = 8.4 Hz, H), 4.46 (t, J = 6.0 Hz, 2H), 3.47-3.44 (m, 2H), 3.02-2.93 (m, 2H), 2.91-2.89 (m, 2H), 2.58 (s, 6H), 2.57 (s, 3H), 2.21-2.20 (m, 2H), 1.90-1.80 (m, 4H), 1.80-1.45 (m, 2H). |
| 17 | 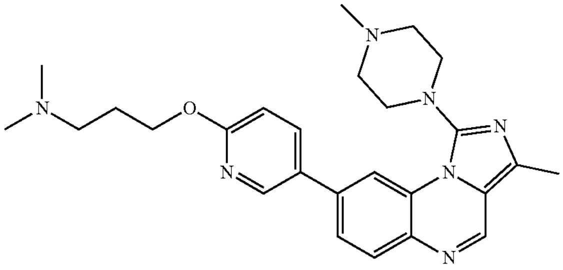 | 459.6 | 460.4 | $CDCl_3$: δ 8.83 (d, J = 2.0 Hz, 1H), 8.66 (s, 1H), 8.50 (d, J = 2.32 Hz, 1H), 7.86-7.98 (m, 2H), 7.59 (dd, J = 8.31, 1.96 Hz, 1H), 6.89 (d, J = 9.56 Hz, 1H), 4.44 (d, J = 6.42 Hz, 2H), 3.34-3.45 (m, 2H), 3.25-3.32 (m, 2H), 2.95 (d, J = 12.10 Hz, 2H), 2.50-2.60 (m, 5H), 2.36-2.42 (m, 5H), 2.28-2.35 (m, 6H), 1.98-2.09 (m, 2H) |
| 18 | 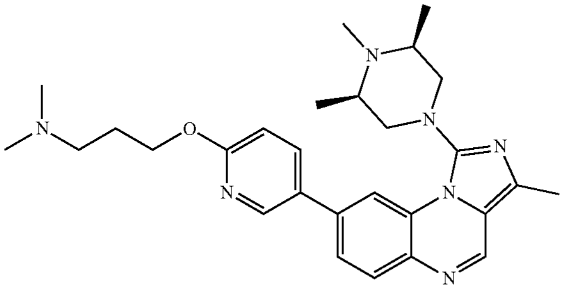 | 487.65 | 488.4 | $CDCl_3$: δ 8.86 (d, J = 1.5 Hz, 1H), 8.64-8.70 (m, 1H), 8.48 (d, J = 2.1 Hz, 1H), 7.85-7.93 (m, 2H), 7.59 (d, J = 8.9 Hz, 1H), 6.84-6.91 (m, 1H), 4.44 (t, J = 6.4 Hz, 2H), 3.32 (d, J = 11.5 Hz, 2H), 2.96 (t, J = 11.2 Hz, 2H), 2.58 (s, 3H), 2.45-2.56 (m, 4H), 2.37 (s, 3H), 2.24-2.34 (m, 6H), 1.97-2.09 (m, 2H), 1.17 (d, J = 6.2 Hz, 6H) |
| 19 | 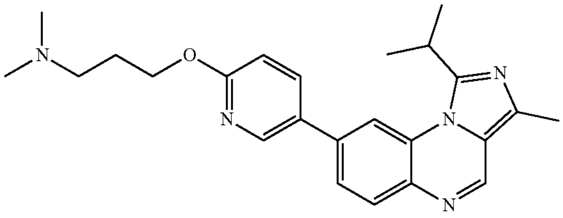 | 403.53 | 404.3 | $CDCl_3$: δ 8.75 (s, 1H), 8.47 (d, J = 2.8 Hz, 1H), 8.22 (d, J = 1.6 Hz, 1H), 7.80 (d, J = 8.4 H, 1H), 7.89-7.86 (m, 1H), 7.64 (d, J = 8 Hz, 1H), 6.90 (d, J = 8.8 Hz, 1H), 4.43 (t, J = 6.4 Hz, 2H), 3.87-3.82 (m, 1H), 2.63 (s, 3H), 2.50 (t, J = 6.8 Hz, 2H), 2.30 (s, 6H), 2.02 (t, J = 7.6 Hz, 2H), 1.61 (d, J = 6.8 Hz, 3H), 1.57 (s, 3H) |
| 20 | 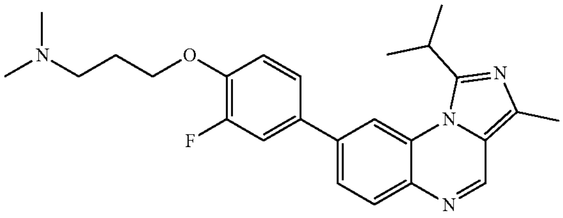 | 420.53 | 421.4 | $CDCl_3$: δ 8.74 (s, 1H), 8.20 (d, J = 8.4 Hz, 1H), 7.97 (d, J = 8.4 Hz, 1H), 7.64 (d, J = 8.4H, 1H), 7.41-7.36 (m, 2H), 7.13 (t, J = 8.4 Hz, 1H), 4.19 (t, J = 6.4 Hz, 2H), 3.88-3.81 (m, 1H), 2.63 (s, 3H), 2.55 (t, J = 22 Hz, 2H), 2.31 (s, 6H), 2.10-2.03 (m, 2H), 1.63 (s, 6H) |

-continued

| Example | Compound structure | MW | LC-MS (ESI) | $^1$H NMR, 400 MHz |
|---|---|---|---|---|
| 21 | 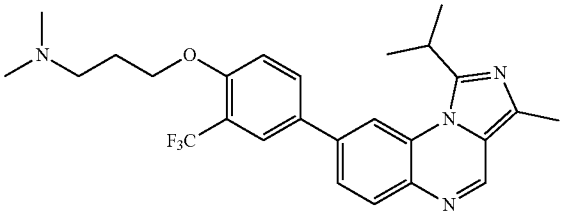 | 470.54 | 471.5 | $CDCl_3$: δ 8.75 (s, 1H), 8.21 (s, 1H), 7.99 (d, J = 8.4 Hz, 1H), 7.86 (d, J = 2.0 Hz, 1H), 7.76 (d, J = 2.0 Hz, 1H), 7.66 (dd, J = 8.4, 1.6 Hz, 1H), 7.17 (d, J = 8.8 Hz, 1H), 4.21 (t, J = 6.0 Hz, 2H), 3.87-3.80 (m, 1H), 2.64 (s, 3H), 2.56 (t, J = 7.0 Hz, 2H), 2.31 (s, 6H), 2.09-2.03 (m, 2H), 1.62 (d, J = 6.8 Hz, 6H) |
| 22 | 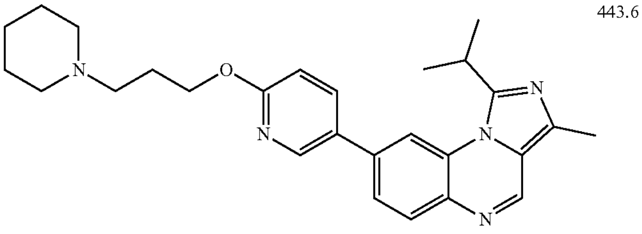 | 443.6 | 444.5 | $CDCl_3$: 8 8.75 (s, 1H), 8.47 (d, J = 2.4 Hz, 1H), 8.22 (d, J = 1.6 Hz, 1H), 7.99 (d, J = 4.0 Hz, 1H), 7.87 (d, J = 2.4, 8.4 Hz, 1H), 7.63 (d, J = 1.6, 8.0 Hz, 1H), 6.88 (d, J = 4.4 Hz, 1H), 4.42 (t, J = 6.4 Hz, 2H), 3.87-3.81 (m, 1H), 2.63 (s, 3H), 2.55-2.45 (m, 6H), 2.07-2.03 (m, 2H), 1.62-1.58 (m, 4H), 1.62 (s, 3H), 1.60 (s, 3H), 1.47-1.46 (m, 2H) |
| 23 | 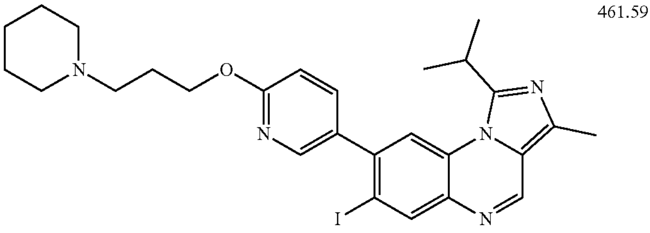 | 461.59 | — | — |
| 24 | 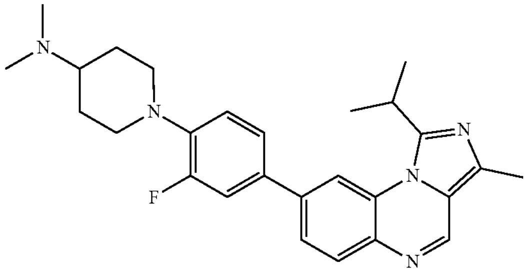 | 445.59 | 446.5 | $CDCl_3$: δ 8.75 (s, 1H), 8.21 (d, J = 2.4 Hz, 1H), 7.95 (d, J = 3.2 Hz, 1H), 7.65 (d, J = 2.0, 8.4 Hz, 1H), 7.39-7.33 (m, 2H), 7.09 (t, J = 9.2 Hz, 1H), 3.88-3.82 (m, 1H), 2.62 (d, J = 8.4 Hz, 2H), 2.82-2.75 (m, 2H), 2.63 (s, 3H), 2.37 (s, 6H), 2.37-2.35 (m, 1H), 1.97 (d, J = 8.8 Hz, 2H), 1.79-1.76 (m, 2H), 1.63 (s, 3H), 1.61 (s, 3H) |
| 25 | 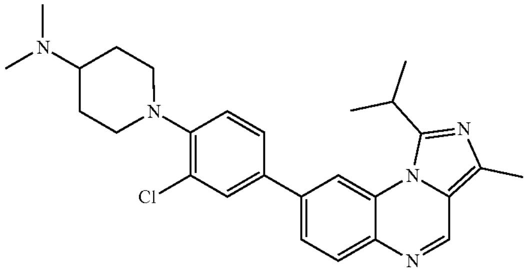 | 462.04 | 462.2 | DMSO-$d_6$: δ 8.74 (s, 1H), 8.21 (d, J = 2.4. Hz, 1H), 7.97 (d, J = 8.4 Hz, 1H), 7.67-7.64 (m, 2H), 7.51 (dd, J = 8.4, 2.0 Hz, 1H), 7.18 (d, J = 8.4 Hz, 1H), 3.84 (m, 1H), 3.56 (br d, J = 12.0 Hz, 2H), 2.77-2.75 (m, 2H), 2.63 (s, 3H), 2.38 (s, 6H), 1.99-1.96 (m, 2H), 1.84-1.79 (m, 2H), 1.63 (s, 3H), 1.61 (s, 3H) |
| 26 | 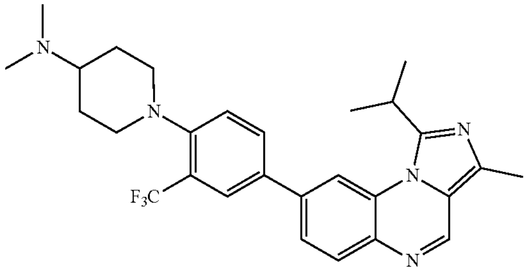 | 495.59 | 496.2 | $CDCl_3$: δ 8.96 (s, 1H), 8.30 (s, 1H), 8.07-8.05 (m, 1H), 7.98-7.94 (m, 2H), 7.88-7.86 (m, 1H), 7.67 (d, J = 8.0 Hz, 1H), 4.05-3.98 (m, 1H), 3.09 (d, J = 12.0 Hz, 2H), 2.82 (t, J = 11 Hz, 3H), 2.54 (s, 3H), 2.24 (s, 6H), 1.88-1.85 (m, 2H), 1.59-1.53 (m, 2H), 1.47 (d, J = 6.4 Hz, 6H). |

-continued
| Example | Compound structure | MW | LC-MS (ESI) | $^1$H NMR, 400 MHz |
| --- | --- | --- | --- | --- |
| 27 | 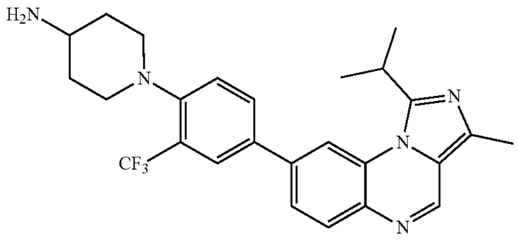 [SMILES: Cc1nc(C(C)C)n2c1cnc1ccc(-c3ccc(N4CCC(N)CC4)c(C(F)(F)F)c3)cc12] | 467.54 | — | — |
| 28 | 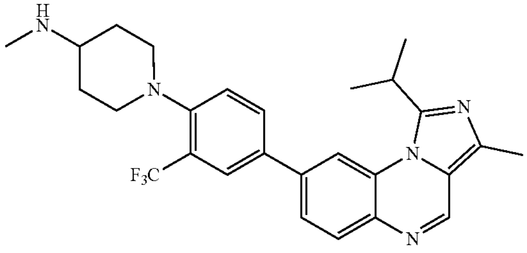 | 481.57 | — | — |
| 29 | 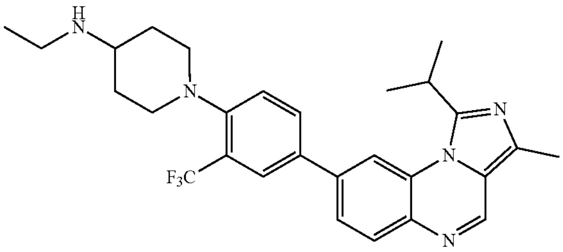 [SMILES: CCNC1CCN(c2ccc(-c3ccc4ncc5c(C)nc(C(C)C)n5c4c3)cc2C(F)(F)F)CC1] | 495.59 | — | — |
| 30 | 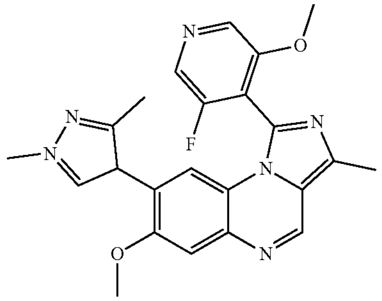 | 433.47 | — | — |
| 31 | 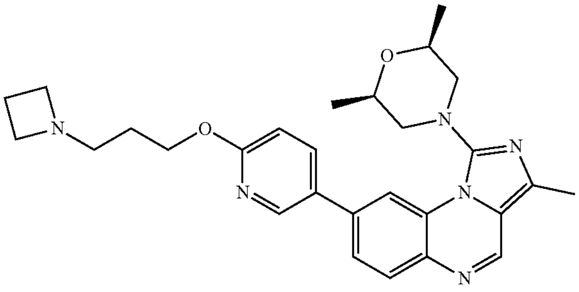 [SMILES: Cc1nc(N2C[C@@H](C)O[C@@H](C)C2)n2c1cnc1ccc(-c3ccc(OCCCN4CCC4)nc3)cc12] | 486.62 | 487.3 | $CDCl_3$: δ 8.84 (d, J = 1.6 Hz, 1H), 8.68 (s, 1H), 8.44 (d, J = 2.0 Hz, 1H), 7.91 (d, J = 8.4 Hz, 1H), 7.84 (dd, J = 2.4, 8.4 Hz, 1H), 7.59 (dd, J = 2.0, 8.4 Hz, 1H), 6.87 (d, J = 8.0 Hz, 1H), 4.42 (t, J = 6.4 Hz, 2H), 4.03-3.96 (m, 2H), 3.36-3.29 (m, 6H), 2.85 (t, J = 11.4 Hz, 2H), 2.91-2.60 (m, 2H), 2.58 (s, 3H), 2.19-2.18 (m, 2H), 1.97-1.94 (m, 2H), 1.27 (d, J = 6.4 Hz, 6H) |

-continued

| Example | Compound structure | MW | LC-MS (ESI) | $^1$H NMR, 400 MHz |
|---|---|---|---|---|
| 32 | 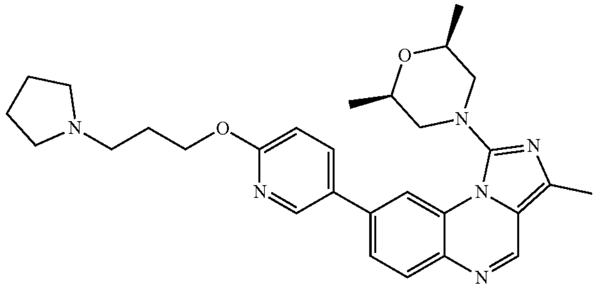 [SMILES: Cc1nc(N2C[C@@H](C)O[C@@H](C)C2)n2c1cnc1ccc(-c3ccc(OCCCN4CCCC4)nc3)cc12] | 500.65 | 501.2 | MeOD; δ 8.97 (s, 1H), 8.79 (s, 1H), 8.48 (d, J = 2.4 Hz, 1H), 8.04 (dd, J = 8.6, 2.6 Hz, 1H), 7.88 (d, J = 8.4 Hz, 1H), 7.74 (d, J = 8.4 Hz, 1H), 6.97 (d, J = 8.4 Hz, 1H), 4.43 (t, J = 6.4 Hz, 2H), 4.02-3.97 (m, 2H), 3.31 (t, J = 1.6 Hz, 2H), 2.78-2.72 (m, 4H), 2.68 (d, J = 2.0 Hz, 4H), 2.57 (s, 3H), 2.12-2.06 (m, 2H), 1.90-1.80 (m, 4H), 1.22 (d, J = 6.0 Hz, 6H) |
| 33 | 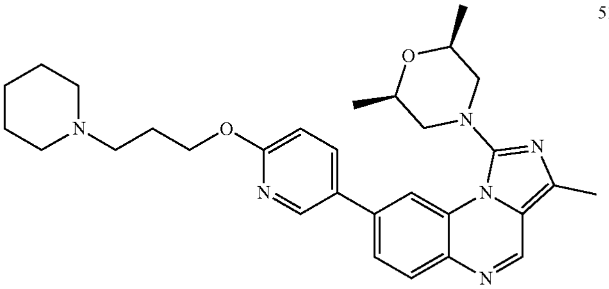 | 514.66 | 515.2 | $CDCl_3$: δ 8.84 (d, J = 1.6 Hz, 1H), 8.68 (s, 1H), 8.45 (d, J = 2.0 Hz, 1H), 7.91 (d, J = 8.0 Hz, 1H), 7.84 (dd, J = 8.2, 2.6 Hz, 1H), 7.60 (d, J = 7.6 Hz, 1H), 6.88 (d, J = 8.8 Hz, 1H), 4.42 (t, J = 6.4 Hz, 2H), 4.00-3.96 (m, 2H), 3.30 (d, J = 12 Hz, 2H), 2.85 (t, J = 11.2 Hz, 2H), 2.58 (s, 3H), 2.55-2.44 (m, 6H), 2.11-2.09 (m, 2H), 1.64-1.62 (m, 3H), 1.48-1.26 (m, 3H), 1.27 (d, J = 6.4 Hz, 6H) |
| 34 | 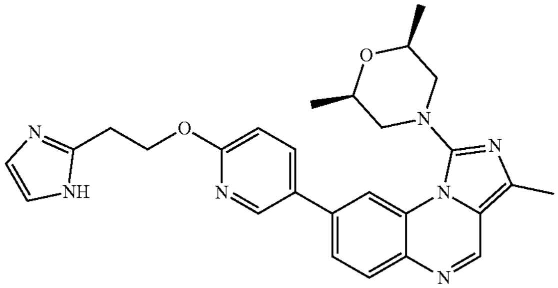 [SMILES: Cc1nc(N2C[C@@H](C)O[C@@H](C)C2)n2c1cnc1ccc(-c3ccc(OCCc4ncc[nH]4)nc3)cc12] | 483.58 | — | — |
| 35 | 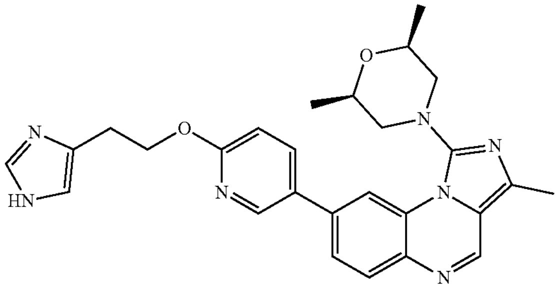 [SMILES: Cc1nc(N2C[C@@H](C)O[C@@H](C)C2)n2c1cnc1ccc(-c3ccc(OCCc4c[nH]cn4)nc3)cc12] | 483.58 | 484.2 | MeOD: δ 8.94 (d, J = 2.4 Hz, 1H), 8.77 (s, 1H), 8.47 (s, 1H), 8.12 (s, 1H), 8.03 (dd, J = 2.4 Hz, J = 8.4 Hz, 1H), 7.87-7.85 (m, 1H), 7.72 (d, J = 8.0 Hz, 1H), 7.15 (s, 1H), 6.98 (d, J = 8.4 Hz, 1H), 4.61 (t, J = 6.4 Hz, 2H), 4.01-3.94 (m, 2H), 3.35-3.31 (m, 2H), 3.18 (t, J = 6.6 Hz, 2H), 2.74 (t, J = 11.0 Hz, 2H), 2.57 (s, 3H), 1.22 (d, J = 6.0 Hz, 6H) |
| 36 | 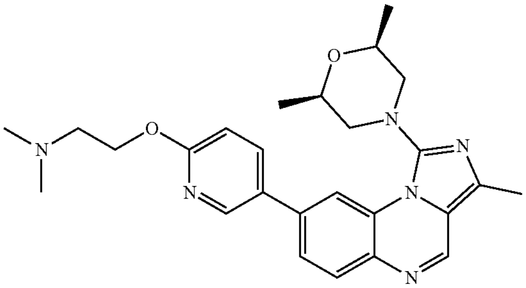 | 460.58 | 461.2 | $CDCl_3$: δ 8.84 (d, J = 2.0 Hz, 1H), 8.68 (s, 1H), 8.44 (d, J = 2.4 Hz, 1H), 7.91 (d, J = 8.0 Hz, 1H), 7.84 (dd, J = 8.8, 2.4 HZ, 1H), 7.60 (dd, J = 8.4, 1.6 HZ, 1H), 6.94 (d, J = 8.8 Hz, 1H), 4.54-4.51 (m, 2H), 4.00-3.96 (m, 2H), 3.32-3.29 (m, 2H), 2.88-2.79 (m, 4H), 2.58 (s, 3H), 2.40 (s, 6H), 1.27 (d, J = 6.4 HZ, 6H) |

-continued

| Example | Compound structure | MW | LC-MS (ESI) | $^1$H NMR, 400 MHz |
|---|---|---|---|---|
| 37 | 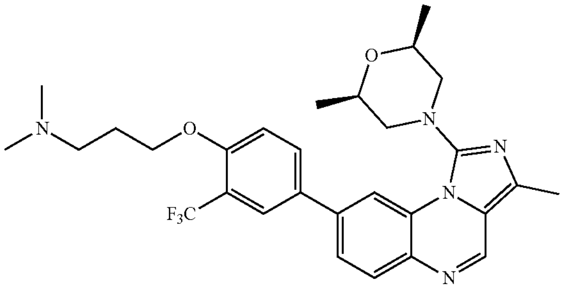 | 541.61 | 542.2 | $CDCl_3$: δ 8.86 (d, J = 1.6 Hz, 1H), 8.68 (s, 1H), 7.91 (d, J = 8.0 Hz, 1H), 7.87 (d, J = 2.0 Hz, 1H), 7.76 (dd, J = 8.4, 1.6 Hz, 1H), 7.63 (dd, J = 8.6, 1.8 Hz, 1H), 7.16 (d, J = 8.8 Hz, 1H), 4.21 (t, J = 6.0 Hz, 2H), 4.03-3.95 (m, 2H), 3.30 (d, J = 11.2 Hz, 2H), 2.86 (t, J = 11.2 Hz, 2H), 2.59 (s, 3H), 2.54 (t, J = 12 Hz, 2H), 2.29 (s, 6H), 2.08-2.02 (m, 2H), 1.28 (d, J = 6.4 Hz, 6H) |
| 38 | 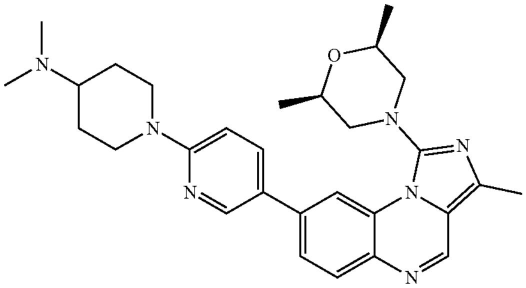 | 499.66 | 500.4 | $CDCl_3$: δ 8.83 (d, J = 1.6 Hz, 1H), 8.65 (s, 1H), 8.51 (d, J = 2.0 Hz, 1H), 7.88 (d, J = 8.4 Hz, 1H), 7.74 (dd, J = 8.6, 2.6 HZ, 1H), 7.60 (dd, J = 8.4, 2.0 HZ, 1H), 6.80 (d, J = 8.8 Hz, 1H), 4.48-4.44 (m, 2H), 4.06-3.98 (m, 2H), 3.31 (d, J = 7.6 HZ, 2H), 2.98-2.92 (m, 2H), 2.85 (t, J = 11.6 HZ, 2H), 2.58 (s, 3H), 2.45-2.36 (m, 1H), 2.35 (s, 6H), 2.01-1.97 (m, 2H), 1.63-1.60 (m, 2H), 1.27 (d, J = 6.4 HZ, 6H) |
| 39 | 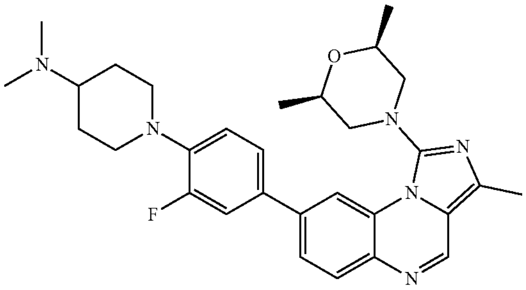 | 516.65 | 517.5 | $CDCl_3$: δ 8.82 (s, 1H), 8.67 (s, 1H), 7.89 (d, J = 8.0 Hz, 1H), 7.61 (dd, J = 8.6, 1.8 Hz, 1H), 7.37-7.31 (m, 2H), 7.07 (t, J = 8.8 Hz, 1H), 4.04-4.00 (m, 2H), 3.66 (d, J = 11.6 Hz, 2H), 3.32 (d, J = 11.6 Hz, 2H), 2.89-2.78 (m, 4H), 2.58 (s, 3H), 2.58-2.49 (m, 1H), 2.49 (s, 6H), 2.13-2.10 (m, 2H), 1.88-1.80 (m, 2H), 1.28 (d, J = 6.4 Hz, 6H) |
| 40 | 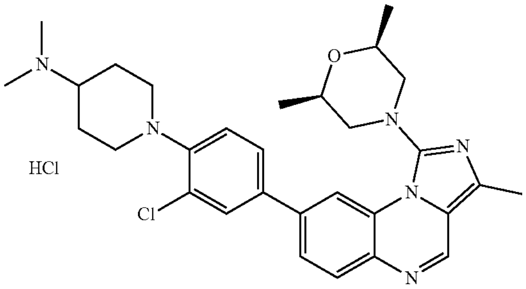 | 533.12 | 533.3 | $CDCl_3$: δ 8.83-8.81 (m, 1H), 8.58-8.51 (m, 1H), 8.43-8.39 (m, 1H), 7.71 (d, J = 5.6 Hz, 1H), 7.63 (s, 1H), 7.51-7.48 (m, 1H), 7.32-7.30 (m, 1H), 4.03-3.98 (m, 2H), 3.72-3.68 (m, 2H), 3.51-3.46 (m, 2H), 3.37-3.28 (m, 1H), 3.03-2.93 (m, 4H), 2.85 (s, 6H), 2.70 (s, 3H), 2.44-2.39 (m, 2H), 2.20-2.12 (m, 2H), 1.34-1.26 (m, 6H) |
| 41 | 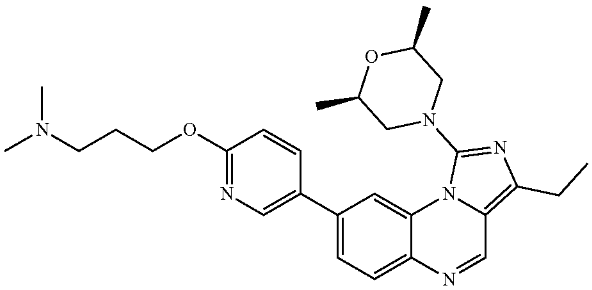 [SMILES: CCc1nc(N2C[C@@H](C)O[C@@H](C)C2)n2c1cnc1ccc(-c3ccc(OCCCN(C)C)nc3)cc12] | 488.64 | 489.5 | DMSO-$d_6$: δ 8.90 (s, 1H), 8.82 (s, 1H), 8.52 (d, J = 1.6 Hz, 1H), 8.04 (dd, J = 2.0 Hz, 8.8 Hz, 1H), 7.86 (d, J = 8.0 Hz, 1H), 7.77 (d, J = 6.8 Hz, 1H), 6.99 (d, J = 8.4 Hz, 1H), 4.35 (t, J = 6.6 Hz, 2H), 3.89-3.85 (m, 2H), 2.93-2.87 (m, 2H), 2.63-2.60 (m, 2H), 2.59-2.52 (m, 2H), 2.38-2.34 (m, 2H), 2.15 (s, 6H), 1.90-1.85 (m, 2H), 1.28 (t, J = 7.4 Hz, 3H), 1.15 (d, J = 6.4 Hz, 6H) |

-continued

| Example | Compound structure | MW | LC-MS (ESI) | $^1$H NMR, 400 MHz |
|---|---|---|---|---|
| 42 | 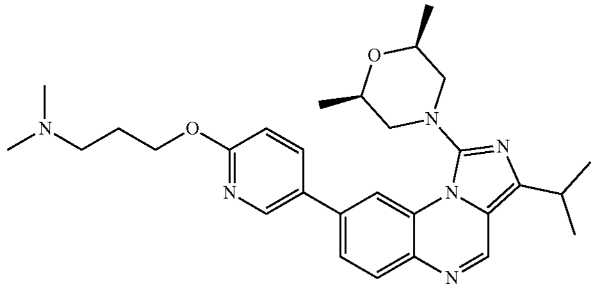 [SMILES: CC(C)c1nc(N2C[C@@H](C)O[C@@H](C)C2)n2c1cnc1ccc(-c3ccc(OCCCN(C)C)nc3)cc12] | 502.66 | 503.6 | MeOD: δ 9.02 (d, J = 2.0 Hz, 1H), 8.84 (s, 1H), 8.51 (s, 1H), 8.07 (dd, J = 2.4 Hz, 8.4 Hz, 1H), 7.87 (d, J = 8.4 Hz, 1H), 7.75-7.73 (m, 1H), 7.00 (d, J = 8.4, 1H), 4.49 (t, J = 6.0 Hz, 2H), 4.00-3.97 (m, 2H), 3.47-3.75 (m, 2H), 3.35-3.33 (m, 1H), 3.21-3.17 (m, 2H), 2.83-2.81 (m, 8H), 2.26-2.20 (m, 2H), 1.42 (d, J = 6.8 Hz, 6H), 1.23 (d, J = 6.0 Hz, 6H) |
| 43 | 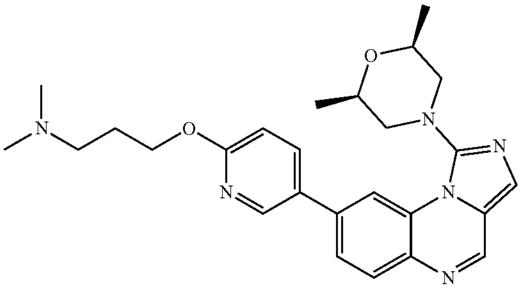 [SMILES: C[C@@H]1CN(c2ncc3cnc4ccc(-c5ccc(OCCCN(C)C)nc5)cc4n23)C[C@H](C)O1] | 460.58 | 461.2 | DMSO-d$_6$: 8.91 (s, 1H), 8.89 (s, 1H), 8.54 (d, J = 2.4 Hz, 1H), 8.07 (dd, J = 2.2 Hz, J = 8.6 Hz, 1H), 7.93 (d, J = 8.4 Hz, 1H), 7.83 (dd, J = 1.6 Hz, J = 8.4 Hz, 1H), 7.73 (s, 1H), 7.01 (d, J = 8.8 Hz, 1H), 4.37 (t, J = 6.6 Hz, 2H), 3.93-3.87 (m, 2H), 3.37-3.34 (m, 2H), 3.69-3.62 (m, 2H), 2.52-2.50 (m, 2H), 2.25 (s, 6H), 1.96-1.89 (m, 2H), 1.16 (d, J = 6.4 Hz, 6H) |
| 44 | 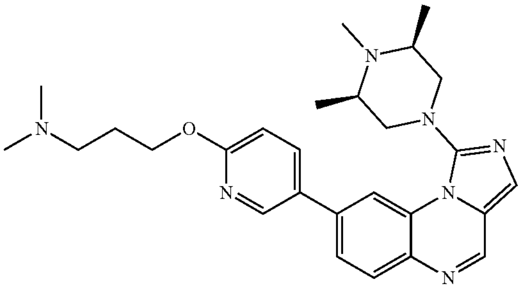 [SMILES: C[C@@H]1CN(c2ncc3cnc4ccc(-c5ccc(OCCCN(C)C)nc5)cc4n23)C[C@H](C)N1C] | 473.63 | — | — |
| 45 | 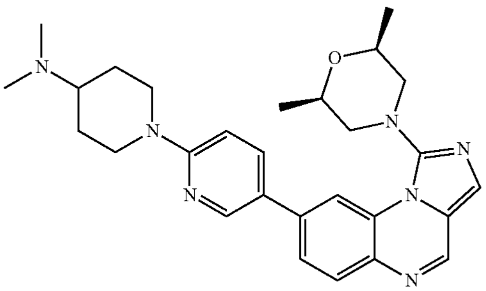 [SMILES: C[C@@H]1CN(c2ncc3cnc4ccc(-c5ccc(N6CCC(N(C)C)CC6)nc5)cc4n23)C[C@H](C)O1] | 485.64 | 486.3 | CDCl$_3$: δ 8.92 (d, J = 2.0 Hz, 1H), 8.74 (s, 1H), 8.52 (d, J = 2.4 Hz, 1H), 7.96 (d, J = 8.4 Hz, 1H), 7.83-7.81 (m, 1H), 7.64 (dd, J = 2.0 Hz, 8.4 Hz, 1H), 7.62 (s, 1H), 6.83 (d, J = 8.4 Hz, 1H), 4.65 (d, J = 13.2 Hz, 2H), 4.06-4.00 (m, 2H), 3.38-3.32 (m, 3H), 2.98-2.95 (m, 2H), 2.90-2.84 (m, 2H), 2.78 (s, 6H), 2.34 (d, J = 13.6 Hz, 2H), 1.88-1.80 (m, 2H), 1.29-1.25 (m, 6H). |

Example 46

N$^1$-(5-(1-((2S,6R)-2,6-dimethylmorpholino)-3-methylimidazo[1,5-a]quinoxalin-8-yl)pyridin-2-yl)-N$^3$,N$^3$-dimethylpropane-1,3-diamine a) Preparation of 1-(5-bromo-2-nitrophenyl)-4-methylimidazole: To a solution of 4-bromo-2-fluoro-1-nitrobenzene (350 g, 1.59 mol) and 4-methyl-1H-imidazole (137.15 g, 1.67 mol) in DMF (2800 mL) was added $K_2CO_3$ (439.75 g, 3.18 mol). The mixture was stirred at 25° C. for 12 hrs, and then the reaction mixture was filtered and the filter cake was washed with DMF (800 mL). The filtrate was poured into $H_2O$ (8 L) and stirred for 10 min, then the mixture was filtered and the filter cake was washed with $H_2O$ (1 L). The solid was slurry with MTBE (1 L) and filtered, the filter cake was washed with MTBE (400 mL). The solid was dried under reduced pressure to give the target product (332 g, 1.18 mol, 73.98% yield) as a yellow solid.

b) Preparation of 4-bromo-2-(4-methylimidazol-1-yl)aniline: To a solution of 1-(5-bromo-2-nitrophenyl)-4-methylimidazole (120 g, 425.39 mmol) in EtOH (1200 mL) was added $NH_4Cl$ (227.55 g, 4.25 mol) in $H_2O$ (600 mL). To the mixture was added Fe (47.51 g, 850.78 mmol) and stirred at 25° C. for 0.5 hr. Then to the mixture was added Fe (71.27 g, 1.28 mol) during 1.5 hrs and stirred at 35° C. for 1 hr. The reaction mixture was filtered and the filter cake was washed with EtOH (800 mL), the pH of the mixture was adjusted to 8 with saturated $NaHCO_3$ solution, and the mixture was concentrated under reduced pressure to give a residue. The residue was slurried with $H_2O$ (1.5 L) and filtered, the filtered cake was dried under reduced pressure to give a residue. The residue was washed with MTBE (300 mL) to give the target product (93 g, 368.89 mmol, 86.72% yield) as a yellow solid.

c) Preparation of 8-bromo-3-methylimidazo[1,5-a]quinoxaline: To a solution of 4-bromo-2-(4-methylimidazol-1-yl)aniline (5 g, 19.83 mmol) in DMSO (50 mL) was added AcOH (2.38 g, 39.67 mmol, 2.27 mL). The mixture was stirred at 130° C. for 36 h. To the mixture was added AcOH (2.38 g, 39.67 mmol, 2.27 mL) and stirred at 130° C. for 24 h. The reaction mixture was diluted with EA (80 mL) and washed with brine (50 mL×3), dried over $Na_2SO_4$, filtered and concentrated under reduced pressure to give a residue. The residue was washed with MTBE (15 mL) to give the target product (2.19 g, 8.16 mmol, 41.08% yield, 97.54% purity) as a yellow solid. LC-MS (ESI): m/z $(M+H)^+$ 262.0.

d) Preparation of 8-bromo-1-chloro-3-methylimidazo[1,5-a]quinoxaline: To a solution of 8-bromo-3-methylimidazo[1,5-a]quinoxaline (2.19 g, 8.15 mmol; 3.65 g, 13.93 mmol) in DCM (120 mL) was added NCS (4.42 g, 33.12 mmol). The mixture was stirred at 25° C. for 12 hrs. The mixture was diluted with saturated $NaHCO_3$ solution (200 mL) and extracted with DCM (100 mL×3). The combined organic layers were washed with brine (100 mL×3), dried over $Na_2SO_4$, filtered and concentrated under reduced pressure to give a residue. The residue was washed with MTBE (30 mL) to give the target product (5.3 g, 17.87 mmol, 80.92% yield) as a yellow solid.

e) Preparation of (2S,6R)-4-(8-bromo-3-methylimidazo[1,5-a]quinoxalin-1-yl)-2,6-dimethylmorpholine: To a solution of 8-bromo-1-chloro-3-methylimidazo[1,5-a]quinoxaline (5.3 g, 17.87 mmol) in DMSO (33 mL) was added DIPEA (6.93 g, 53.61 mmol, 9.34 mL) and (2S,6R)-2,6-dimethylmorpholine (6.18 g, 53.61 mmol). The mixture was stirred at 90° C. for 12 hrs. Then to the mixture was added (2S,6R)-2,6-dimethylmorpholine (2.06 g, 17.87 mmol, 2.20 mL) and stirred at 90° C. for 12 hrs. The reaction mixture was diluted with $H_2O$ (100 mL) and extracted with DCM (100 mL×3). The combined organic layers were washed with brine (100 mL×3), dried over $Na_2SO_4$, filtered and concentrated under reduced pressure to give a residue. The residue was washed with MTBE (35 mL) to give the target product (5.45 g, 14.52 mmol, 81.22% yield) as a yellow solid. $^1H$ NMR (400 MHz, $CDCl_3$): δ 8.80 (d, J=2.0 Hz, 1H), 8.66 (s, 1H), 7.71 (d, J=8.4 Hz, 1H), 7.53 (dd, J=2.0, 8.8 Hz, 1H), 4.07-4.00 (m, 2H), 3.25 (d, J=2.0 Hz, 1H), 2.86-2.78 (m, 2H), 2.56 (s, 3H), 1.29 (d, J=6.4 Hz, 6H).

f) Preparation of $N^1$-(5-(1-((2S,6R)-2,6-dimethylmorpholino)-3-methylimidazo[1,5-a]quinoxalin-8-yl)pyridin-2-yl)-$N^3$,$N^3$-dimethylpropane-1,3-diamine: To a mixture of (2R,6S)-4-(8-bromo-3-methyl-imidazo[1,5-a]quinoxalin-1-yl)-2,6-dimethyl-morpholine (100 mg, 266.48 μmol), $N^1$,$N^1$-dimethyl-$N^3$-(5-(4,4,5,5-tetramethyl-1,3,2-dioxaborolan-2-yl)pyridin-2-yl)propane-1,3-diamine (113.87 mg, 373.07 μmol), $Cs_2CO_3$ (173.65 mg, 532.96 μmol) in dioxane (15 mL) and $H_2O$ (0.7 mL) was added $Pd(dppf)Cl_2$ (9.75 mg, 13.32 μmol). The reactor was degassed and purged with $N_2$ for 3 times, and then the mixture was stirred at 90° C. for 2 hrs under $N_2$ atmosphere. The reaction mixture was dried over $Na_2SO_4$, filtered and concentrated under reduced pressure to give a residue, which was purified by prep-TLC ($SiO_2$, DCM:MeOH=9:1). The crude product was triturated with MeCN at 25° C. for 30 min to give the title compound (24.87 mg, 18.96% yield) as a yellow solid.

The following compounds of Examples 47-64 were prepared using methods similar to that described in Example 2, 14 or 46.

| Example | Compound structure | MW | LC-MS (ESI) | $^1H$ NMR, 400 MHz |
|---|---|---|---|---|
| 46 | 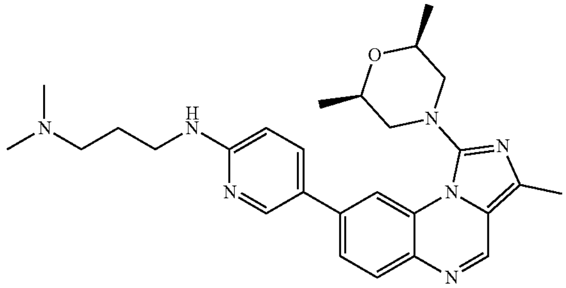 | 473.61 | 474.4 | $CDCl_3$: δ 8.82 (d, J = 2.0 Hz, 1H), 8.65 (s, 1H), 8.42 (d, J = 2.0 Hz, 1H), 7.87 (d, J = 8.4H, 2H), 7.71 (dd, J = 2.4 Hz, 8.8 Hz, 1H), 7.58 (dd, J = 2.0 Hz, 8.4 Hz, 1H), 6.53 (d, J = 8.8 Hz, 1H), 5.57 (s, 1H), 4.02-3.97 (m, 2H), 3.46 (s, 2H), 3.30 (d, J = 11.2 Hz, 2H), 2.84 (t, J = 11.2 Hz, 2H), 2.58 (s, 3H), 2.49 (t, J = 6.8 Hz, 2H), 2.31 (s, 6H), 1.90-1.83 (m, 2H), 1.26 (d, J = 6.4 Hz, 6H) |
| 47 | 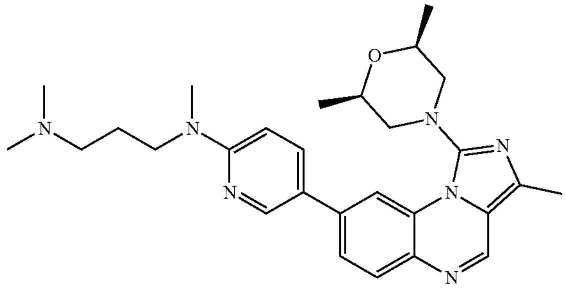 | 487.65 | 488.4 | $CDCl_3$: δ 8.82 (d, J = 1.6 Hz, 1H), 8.64 (s, 1H), 8.50 (d, J = 2.8 Hz, 1H), 7.87 (d, J = 8.4 Hz, 1H), 7.73 (dd, J = 2.4, 8.8 Hz, 1H), 7.59 (dd, J = 1.6, 8.4 Hz, 1H), 6.66 (d, J = 8.8 Hz, 1H), 4.06-3.99 (m, 2H), 3.66 (t, J = 7.6 Hz, 2H), 3.32 (d, J = 11.2 Hz, 2H), 3.15 (s, 3H), 2.85 (t, J = 7.6 Hz, 2H), 2.56 (s, 3H), 2.37 (t, J = 7.6 Hz, 2H), 2.28 (s, 6H), 1.87-1.81 (m, 2H), 1.27 (d, J = 6.4 Hz, 6H). |

-continued

| Example | Compound structure | MW | LC-MS (ESI) | $^1$H NMR, 400 MHz |
|---|---|---|---|---|
| 48 | 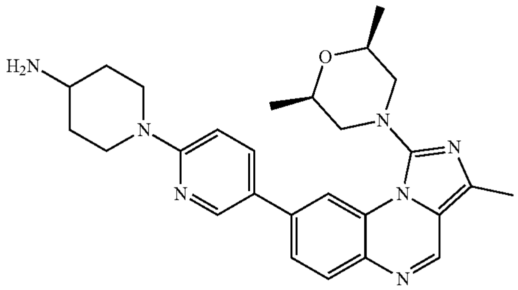 [SMILES: Cc1nc(N2C[C@@H](C)O[C@@H](C)C2)n2c1cnc1ccc(-c3ccc(N4CCC(N)CC4)nc3)cc12] | 471.60 | 472.3 | $CDCl_3$: δ 8.81 (d, J = 2.0 Hz, 1H), 8.65 (s, 1H), 8.50 (d, J = 2.0 Hz, 1H), 7.87 (d, J = 8.4 Hz, 1H), 7.76 (dd, J = 2.4 Hz, 8.8 Hz, 1H), 7.57 (dd, J = 2.0 Hz, 10.0 Hz, 1H), 6.80 (d, J = 8.4 Hz, 1H), 4.47 (d, J = 13.6 Hz, 2H), 4.01-3.98 (m, 2H), 3.33-3.28 (m, 3H), 3.02 (t, J = 7.8 Hz, 2H), 2.83 (t, J = 10.8 Hz, 2H), 2.57 (s, 3H), 2.15 (d, J = 10.4 Hz, 2H), 1.77-1.69 (m, 2H), 1.26 (d, J = 6.4 Hz, 6H) |
| 49 | 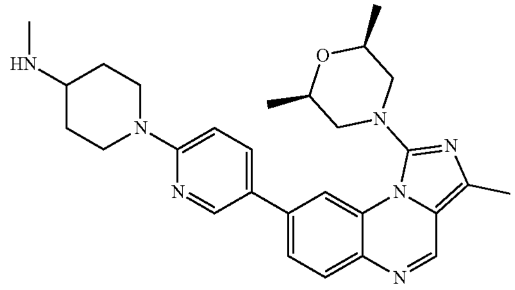 [SMILES: CNC1CCN(c2ccc(-c3ccc4ncc5c(C)nc(N6C[C@@H](C)O[C@@H](C)C6)n5c4c3)cn2)CC1] | 485.62 | 486.3 | $CDCl_3$: δ 8.83 (d, J = 1.6 Hz, 1H), 8.65 (s, 1H), 8.51 (d, J = 2.0 Hz, 1H), 7.88 (d, J = 8.4 Hz, 1H), 7.75 (dd, J = 9.0, 2.6 Hz, 1H), 7.59 (dd, J = 8.4, 1.6 Hz, 1H), 6.80 (d, J = 9.2 Hz, 1H), 4.38-4.38 (m, 2H), 4.05-3.98 (m, 2H), 3.31 (d, J = 11.6 Hz, 2H), 3.08-3.01 (m, 2H), 2.85 (t, J = 11.2 Hz, 2H), 2.75-2.64 (m, 1H), 2.58 (s, 3H), 2.51 (s, 3H), 2.06-2.03 (m, 2H), 1.51-1.40 (m, 2H), 1.28 (d, J = 6.0 Hz, 6H) |
| 50 | 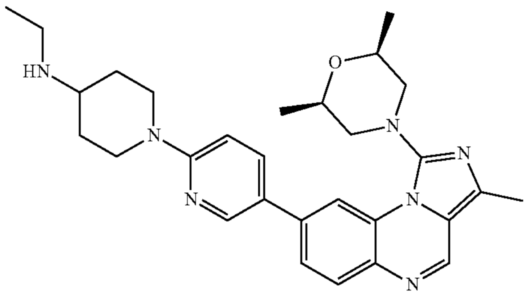 [SMILES: CCNC1CCN(c2ccc(-c3ccc4ncc5c(C)nc(N6C[C@@H](C)O[C@@H](C)C6)n5c4c3)cn2)CC1] | 499.65 | 500.3 | $CDCl_3$: δ 8.83 (d, J = 2.0 Hz, 1H), 8.65 (s, 1H), 8.51 (d, J = 2.4 Hz, 1H), 7.88 (d, J = 8.4 Hz, 1H), 7.75 (dd, J = 2.4, 8.8 Hz, 1H), 7.59 (dd, J = 1.6, 8.0 Hz, 1H), 6.80 (d, J = 9.2 Hz, 1H), 4.37 (d, J = 8.8 Hz, 2H), 4.04-3.98 (m, 2H), 3.1 (s, 1H), 3.31 (d, J = 11.2 Hz, 2H), 3.05-2.98 (m, 2H), 2.87-2.73 (m, 5H), 2.58 (s, 3H), 2.04-2.01 (m, 2H), 1.48-1.44 (m, 2H), 1.27 (d, J = 6.0 Hz, 6H), 1.16 (t, J = 7.0 Hz, 3H) |
| 51 | 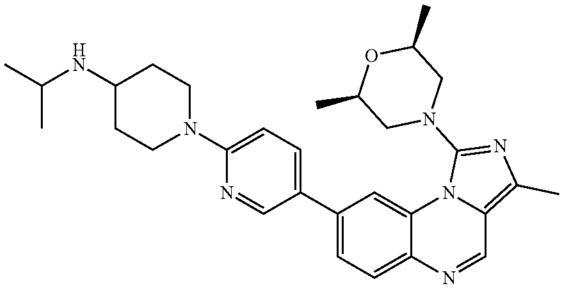 [SMILES: Cc1nc(N2C[C@@H](C)O[C@@H](C)C2)n2c1cnc1ccc(-c3ccc(N4CCC(NC(C)C)CC4)nc3)cc12] | 513.69 | 514.4 | $CDCl_3$: δ 8.81 (d, J = 1.6 Hz, 1H), 8.64 (s, 1H), 8.50 (d, J = 2.0 Hz, 1H), 7.86 (d, J = 8.4 Hz, 1H), 7.75 (dd, J = 2.0, 8.8 Hz, 1H), 7.58 (dd, J = 1.6, 8.4 Hz, 1H), 6.79 (d, J = 9.2 Hz, 1H), 4.48 (d, J = 13.2 Hz, 2H), 4.02-3.97 (m, 2H), 3.33-3.28 (m, 3H), 3.16-3.10 (m, 1H), 2.99-2.93 (m, 2H), 2.86-2.81 (m, 2H), 2.57 (s, 3H), 2.15 (m, 2H), 1.79-1.72 (m, 2H), 1.31 (d, J = 6.4 Hz, 6H), 1.26 (d, J = 6.0 Hz, 6H). |
| 52 | 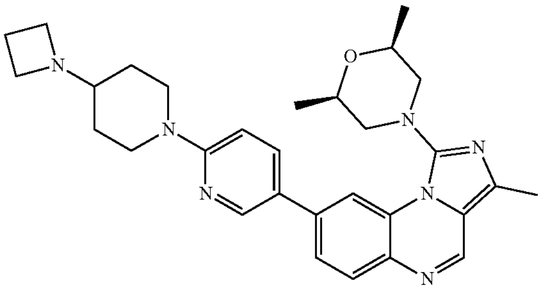 [SMILES: Cc1nc(N2C[C@@H](C)O[C@@H](C)C2)n2c1cnc1ccc(-c3ccc(N4CCC(N5CCC5)CC4)nc3)cc12] | 511.67 | 512.3 | $CDCl_3$: δ 8.83 (s, 1H), 8.82 (s, 1H), 8.49 (d, J = 2.0 Hz, 1H), 7.89 (d, J = 8.4 Hz, 1H), 7.76 (dd, J = 2.4 Hz, 8.8 Hz, 1H), 7.59 (d, J = 6.4 Hz, 1H), 6.78 (d, J = 8.8 Hz, 1H), 4.51 (d, J = 14.0 Hz, 2H), 4.02-4.00 (m, 2H), 3.88 (t, J = 7.4 Hz, 4H), 3.31 (d, J = 11.6 Hz, 2H), 2.98-2.82 (m, 5H), 2.58 (s, 3H), 2.44-2.42 (m, 2H), 2.01-1.98 (m, 2H), 1.75-1.73 (m, 2H), 1.27 (d, J = 6.4 Hz, 3H). |

-continued

| Example | Compound structure | MW | LC-MS (ESI) | $^1$H NMR, 400 MHz |
|---|---|---|---|---|
| 53 | 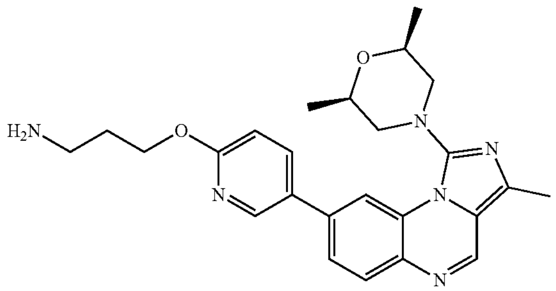 [SMILES: Cc1nc(N2C[C@@H](C)O[C@@H](C)C2)n2c1cnc1ccc(-c3ccc(OCCCN)nc3)cc12] | 446.54 | 447.3 | $CDCl_3$: δ 8.84 (d, J = 1.6 Hz, 1H), 8.68 (s, 1H), 8.45-8.44 (d, J = 2.0 Hz, 1H), 7.93-7.91 (d, J = 8.4 Hz, 1H), 7.86-7.83 (m, 1H), 7.61-7.58 (m, 1H), 6.89-6.87 (d, J = 8.8 Hz, 1H), 4.48 (t, J = 6.4 Hz, 2H), 4.00-3.96 (m, 2H), 3.31 (d, J = 11.2 Hz, 2H), 2.94 (t, J = 6.8 Hz, 2H), 2.88-2.82 (m, 2H), 2.58 (s, 3H), 2.02-1.96 (m, 2H), 1.27 (d, J = 6.0 Hz, 6H) |
| 54 | 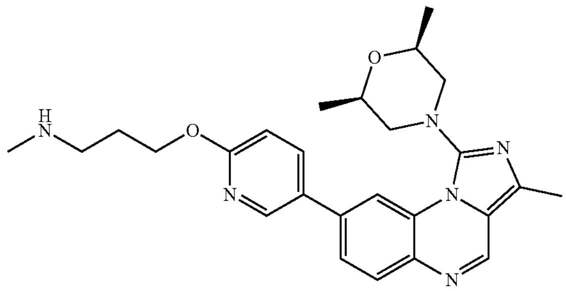 | 460.57 | 461.3 | MeOD: δ 9.28-9.13 (m, 1H), 8.77-8.76 (m, 1H) 8.52 (s, 1H) 8.41-8.37 (m, 1H) 7.91-7.84 (m, 2H) 7.48-7.34 (m, 2H) 4.51-4.48 (t, J = 6.4 Hz, 2H) 4.02-3.99 (m, 2H) 3.70-3.48 (m, 4H) 3.19 (s, 4H) 2.80-2.75 (m, 1H) 2.72 (s, 3H) 2.15-2.09 (m, 2H) 1.21 (d, J = 2.4 Hz, 6H) |
| 55 | 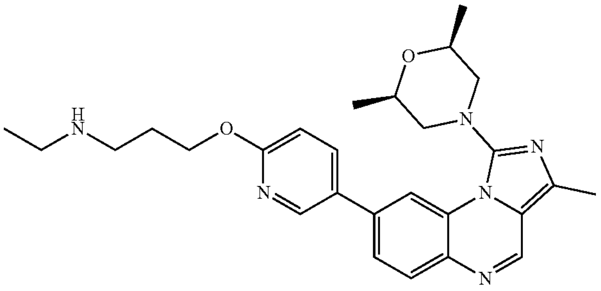 [SMILES: CCNCCCOc1ccc(-c2ccc3ncc4c(C)nc(N5C[C@@H](C)O[C@@H](C)C5)n4c3c2)cn1] | 474.6 | 475.3 | $CDCl_3$: δ 8.79 (d, J = 2.0 Hz, 1H), 8.73 (s, 1H), 8.71 (s, 1H), 7.95-7.90 (m, 2H), 7.81 (d, J = 2.4 Hz, 1H), 7.53-7.50 (m, 1H), 7.03-7.00 (m, 1H), 4.67-4.63 (m, 2H), 3.92-3.80 (m, 2H), 3.78-3.63 (m, 2H), 3.61-3.59 (m, 2H), 3.27 (d, J = 12.0 Hz, 2H), 2.90-2.84 (m, 2H), 2.59 (s, 3H), 2.22-2.19 (m, 2H), 1.43-1.40 (m, 3H), 1.29 (d, J = 6.0 Hz, 6H) |
| 56 | 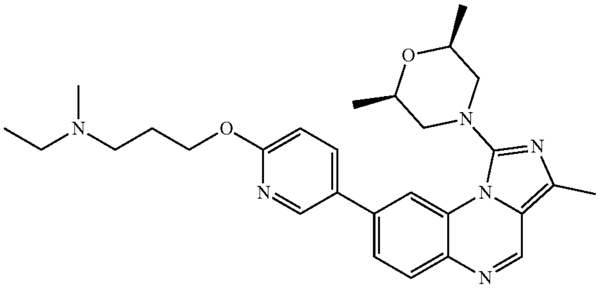 [SMILES: CCN(C)CCCOc1ccc(-c2ccc3ncc4c(C)nc(N5C[C@@H](C)O[C@@H](C)C5)n4c3c2)cn1] | 488.62 | 489.3 | $CDCl_3$: δ 8.72 (d, J = 1.6 Hz, 1H), 8.70 (s, 1H), 7.88 (d, J = 8.4 Hz, 1H), 7.72 (d, J = 2.8 Hz, 1H), 7.68-7.65 (m, 1H), 7.48 (dd, J = 2.0 Hz, 8.0 Hz, 1H), 6.73 (d, J = 9.6 Hz, 1H), 4.12-4.09 (m, 2H), 4.09-3.95 (m, 2H), 3.28 (d, J = 11.2 Hz, 2H), 2.88-2.83 (m, 2H), 2.58 (s, 3H), 2.43-2.39 (m, 4H), 2.21 (s, 3H), 2.03-2.00 (m, 2H), 1.29-1.27 (d, J = 6.4 Hz, 6H), 1.03-1.00 (t, J = 7.2 Hz, 3H) |
| 57 | 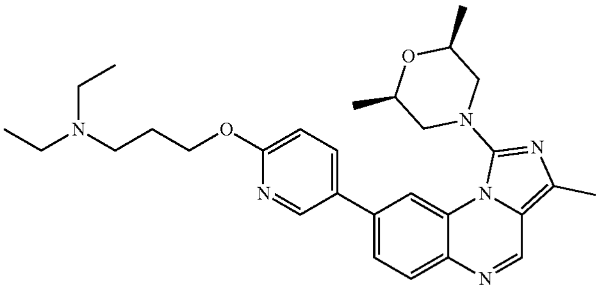 [SMILES: CCN(CC)CCCOc1ccc(-c2ccc3ncc4c(C)nc(N5C[C@@H](C)O[C@@H](C)C5)n4c3c2)cn1] | 502.65 | 503.4 | $CDCl_3$: δ 8.72 (d, J = 1.6 Hz, 1H), 8.67 (s, 1H), 7.88 (d, J = 8.4 Hz, 1H), 7.69 (d, J = 4.0 Hz, 1H), 7.67-7.64 (m, 1H), 7.48 (dd, J = 2.0 Hz, 8.4 Hz, 1H), 6.73 (d, J = 9.2 Hz, 1H), 4.10 (t, J = 6.8 Hz, 2H), 3.97-3.94 (m, 2H), 3.29 (d, J = 11.6 Hz, 2H), 2.88-2.83 (m, 2H), 2.58 (s, 3H), 2.54-2.50 (m, 6H), 2.03-1.98 (m, 2H), 1.28 (d, J = 6.4 Hz, 6H), 0.99 (t, J = 7.2 Hz, 6H) |

-continued

| Example | Compound structure | MW | LC-MS (ESI) | $^1$H NMR, 400 MHz |
|---|---|---|---|---|
| 58 | 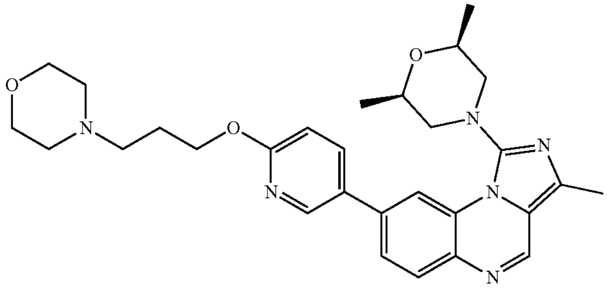 [SMILES: Cc1nc(N2C[C@@H](C)O[C@@H](C)C2)n2c1cnc1ccc(-c3ccc(OCCCN4CCOCC4)nc3)cc12] | 516.63 | 517.2 | $CDCl_3$: δ 8.84 (s, 1H), 8.68 (s, 1H), 8.44 (d, J = 2.0 Hz, 1H), 7.82-7.94 (m, 2H), 7.60 (d, J = 8.0 Hz, 1H), 6.88 (d, J = 8.4 Hz, 1H), 4.46 (t, J = 5.6 Hz, 2H), 3.93-4.03 (m, 2H), 3.85-3.67 (m, 4H), 3.32-2.89 (m, 2H), 2.85 (t, J = 7.0 Hz, 2H), 2.58 (s, 3H), 2.73-2.41 (m, 6H), 2.03-2.21 (m, 2H), 1.27 (d, J = 6.4 Hz, 6H) |
| 59 | 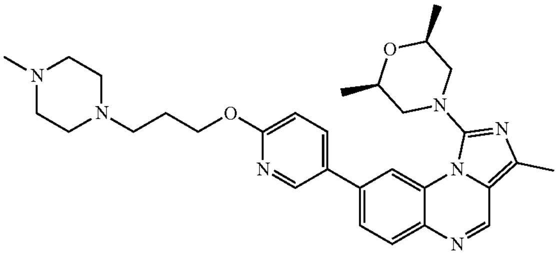 | 529.68 | 530.3 | $CDCl_3$: δ 8.84 (d, J = 2.0 Hz, 1H), 8.68 (s, 1H), 8.44 (d, J = 2.0 Hz, 1H), 7.91 (d, J = 8.4 Hz, 1H), 7.84 (dd, J = 2.4 Hz, 8.4 Hz, 1H), 7.59 (dd, J = 2.0 Hz, 8.8 Hz, 1H), 6.87 (d, J = 8.4 Hz, 1H), 4.43 (t, J = 6.4 Hz, 2H), 4.00-3.95 (m, 2H), 3.30 (d, J = 11.2 Hz, 2H), 2.85 (t, J = 7.2 Hz, 2H), 2.60-3.50 (m, 13H), 2.31 (s, 3H), 2.05-2.02 (m, 2H), 1.26 (d, J = 6.4 Hz, 6H) |
| 60 | 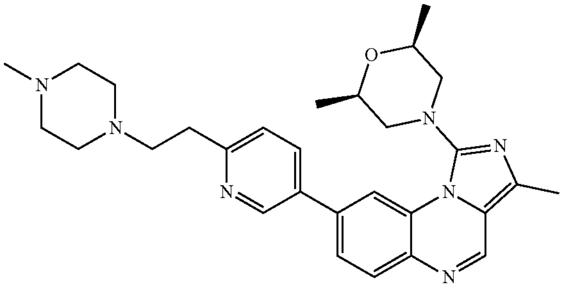 | 499.65 | 500.3 | $CDCl_3$: δ 8.90 (d, J = 1.6 Hz, 1H), 8.83 (d, J = 2.0 Hz, 1H), 8.69 (s, 1H), 7.94 (d, J = 8.4 Hz, 1H), 7.88-7.85 (m, 1H), 7.65-7.63 (m, 1H), 7.35 (d, J = 2.0 Hz, 8.0 Hz, 1H), 4.01-3.94 (m, 2H), 3.29 (d, J = 11.2 Hz, 2H), 3.11-3.09 (m, 2H), 2.97-2.94 (m, 2H), 2.87-2.77 (m, 10H), 2.58 (s, 3H), 2.44 (s, 3H), 1.26 (d, J = 6.4 Hz, 6H). |
| 61 | 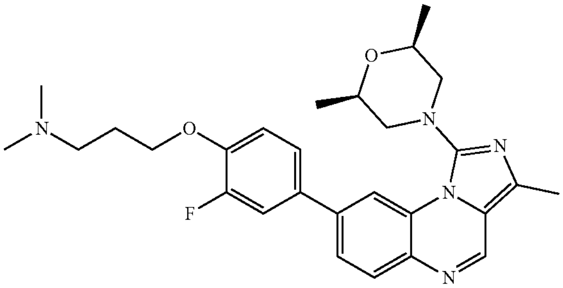 | 491.6 | 492.3 | $CDCl_3$: δ 8.80 (d, J = 1 .6 Hz, 1H), 8.67 (s, 1H), 7.89 (d, J = 8.4 Hz, 1H), 7.59 (dd, J = 1 .6 Hz, 8.0 Hz, 1H), 7.38-7.33 (m, 2H), 7.14-7.09 (m, 1H), 4.21-4.18 (m, 2H), 4.03-3.97 (m, 2H), 3.31 (d, J = 11.2 Hz, 2H), 2.88-2.82 (m, 2H), 2.61-2.60 (m, 2H), 2.58 (s, 3H), 2.35 (s, 6H), 2.13-2.06 (m, 2H), 1.28 (d, J = 6.0 Hz, 6H) |
| 62 | 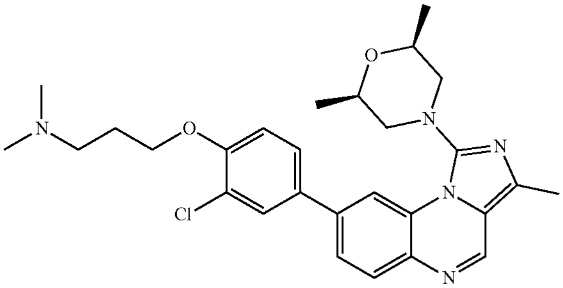 | 508.04 | 508.2 | $CDCl_3$: δ 8.78 (d, J = 2.0 Hz, 1H), 8.67 (s, 1H), 7.89 (d, J = 8.4 Hz, 1H), 7.65 (d, J = 2.4 Hz, 1H), 7.60 (dd, J = 2.0 Hz, 8.4 Hz, 1H), 7.49 (dd, J = 2.0 Hz, 8.4 Hz, 1H), 7.08 (d, J = 8.4 Hz, 1H), 4.22-4.19 (m, 2H), 4.05-3.98 (m, 2H), 3.32 (d, J = 11.2 Hz, 2H), 2.89-2.83 (m, 2H), 2.75-2.71 (m, 2H), 2.58 (s, 3H), 2.42 (s, 6H), 2.20-2.13 (m, 2H), 1.30 (d, J = 6.4 Hz, 6H) |

-continued

| Example | Compound structure | MW | LC-MS (ESI) | $^1$H NMR, 400 MHz |
|---|---|---|---|---|
| 63 | 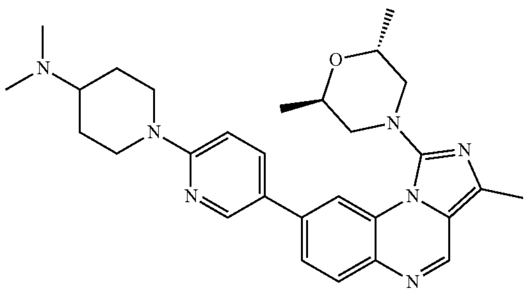 and 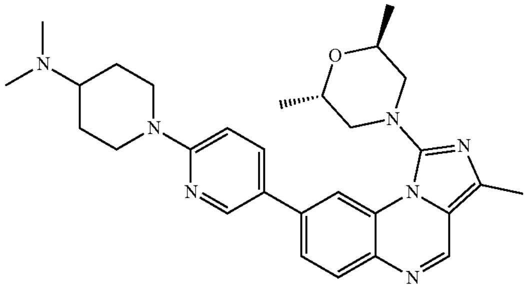 | 499.65 | 500.3 | 63-A: $CDCl_3$: δ 8.82 (d, J = 2.0 Hz, 1H), 8.65 (s, 1H), 8.51 (d, J = 2.4 Hz, 1H), 7.89 (d, J = 8.4 Hz, 1H), 7.76 (dd, J = 2.8 Hz, 8.8 Hz, 1H), 7.59 (dd, J = 2.0 Hz, 8.0 Hz, 1H), 6.79 (d, J = 9.2 Hz, 1H), 4.46-4.43 (m, 2H), 4.32-4.28 (m, 2H), 3.52-3.49 (m, 1H), 3.32-3.29 (m, 1H), 3.18-3.15 (m, 1H), 2.98-2.97 (m, 2H), 2.67-2.66 (m, 1H), 2.58 (s, 6H), 2.41-2.39 (m, 1H), 2.35 (s, 3H), 1.96-1.93 (m, 2H), 1.62-1.61 (m, 2H), 1.54 (d, J = 6.0 Hz, 3H), 1.16 (d, J = 6.0 Hz, 3H). 63-B: $CDCl_3$: δ 8.83 (d, J = 2.0 Hz, 1H), 8.66 (s, 1H), 8.52 (d, J = 2.0 Hz, 1H), 7.89 (d, J = 8.4 Hz, 1H), 7.78 (dd, J = 2.8 Hz, 8.8 Hz, 1H), 7.59 (dd, J = 2.0 Hz, 8.4 Hz, 1H), 6.79 (d, J = 8.4 Hz, 1H), 4.55-4.52 (m, 2H), 4.32-4.27 (m, 2H), 3.54-3.52 (m, 1H), 3.31-3.29 (m, 1H), 3.18-3.15 (m, 1H), 2.98-2.95 (m, 2H), 2.71-2.68 (m, 1H), 2.67 (s, 3H), 2.58-2.55 (m, 1H), 2.55 (s, 6H), 2.15-2.12 (m, 2H), 1.74-1.71 (m, 2H), 1.53 (d, J = 6.8 Hz, 3H), 1.16 (d, J = 6.0 Hz, 3H) |
| 64 | 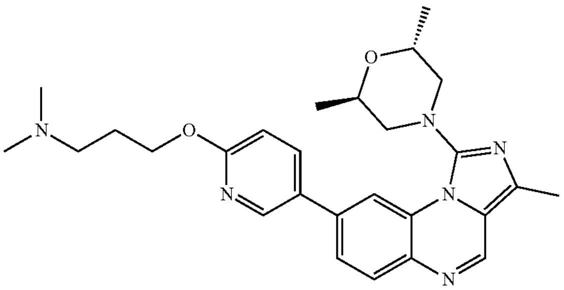 and 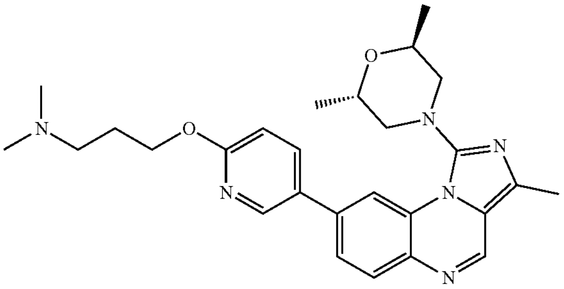 | 474.6 | 475.2 | 64-A: $CDCl_3$: δ 8.85 (d, J = 2.0 Hz, 1H), 8.68 (s, 1H), 8.44 (d, J = 2.4 Hz, 1H), 7.92 (d, J = 8.4 Hz, 1H), 7.86 (dd, J = 2.4, 8.4 Hz, 1H), 7.59 (dd, J = 1.6. 8.0 Hz, 1H), 6.87 (d, J = 8.4 Hz, 1H), 4.47 (t, J = 6.4 Hz, 2H), 4.29-4.25 (m, 2H), 3.50-3.49 (m, 1H), 3.29 (d, J = 10.8 Hz, 1H), 3.16 (d, J = 11.2 Hz, 1H), 2.88-2.85 (m, 2H), 2.69 (t, J = 10.8 Hz, 1H), 2.60-2.57 (m, 9H), 2.24-2.22 (m, 2H), 1.49 (d, J = 6.8 Hz, 3H), 1.15 (d, J = 6.4 Hz, 3H). 64-B: $CDCl_3$: δ 8.85 (d, J = 2.0 Hz, 1H), 8.69 (s, 1H), 8.44 (d, J = 2.4 Hz, 1H), 7.92 (d, J = 8.0 Hz, 1H), 7.87 (dd, J = 2.8, 8.8 Hz, 1H), 7.59 (dd, J = 2.0, 8.4 Hz, 1H), 6.87 (d, J = 8.8 Hz, 1H), 4.49 (t, J = 6.0 Hz, 2H), 4.31-4.25 (m, 2H), 3.53-3.50 (m, 1H), 3.28 (d, J = 11.2 Hz, 1H), 3.15 (d, J = 12.0 Hz, 1H), 3.10-2.85 (m, 2H), 2.82-2.62 (m, 7H), 2.58 (s, 3H), 2.34-2.31 (m, 2H), 1.50 (d, J = 6.4 Hz, 3H), 1.16 (d, J = 6.0 Hz, 3H). |

Example Compound structure MW LC-MS (ESI)$^1$H NMR, 400 MHz

Example 65

Determination of the Inhibitory Effect In Vitro of the Compound of Example 2 and its Analogues on ATM Using In Vitro ATM Kinase Assay ATM enzymatic activity was measured using Cisbio's HTRF reagent in a 384-well plate (Greiner, #784075). 2.5 μL of gradient concentration compound working solution diluted with buffer was added to the 384-well plate, then 2.5 μL of 120 nM p53 substrate (Eurofins, #14-952) and 2.5 μL of 2 ng/μL ATM enzyme (Eurofins, 14-933) were added successively, and finally 2.5 μL of a mixture solution containing 240 μM ATP, 20 mM $Mg(AcO)_2$ and 20 mM $MnCl_2$ was added. The mixtures were centrifuged at 1000 rpm for 1 minute, and reacted in dark for 30 minutes at room temperature. Then, 5 μL of EDTA termination solution (250 mm) was added to terminate the reaction. After 5 μL of detection mixture (Anti-phospho-p53 (ser15)-K (Cisbio, #61P08KAE, 0.084 ng/μL) and Anti-GST-d2 (Cisbio, #61GSTDLA, 5.00 ng/μL)) was finally added to each well, the mixtures were cultured at room temperature over night, and the fluorescence values at 665 nm and 615 nm were measured on Envision 2104. The final concentration of each reagent of the experiment was as follows: 12.5 mM HEPES (pH8.0), 0.5% glycerol, 0.005% Brij-35, 0.625 mM DTT, 0.0125% BSA, 15 nM p53, 0.25 ng/μL ATM, 30 μM ATP, 2.5 mM $Mg(AcO)_2$, 2.5 mM $MnCl_2$, 62.5 mM EDTA, 0.021 ng/μL Anti-phospho-p53, 1.25 ng/μL Anti-GST-d2.

Relative fluorescence ratio was calculated: $Ratio_{665\ nm/615\ nm} - Ratio_{background}$, and inhibition rate %=(1−(relative fluorescence ratio of test compound well−relative fluorescence ratio of positive control well)/(relative fluorescence ratio of negative control well−relative fluorescence ratio of positive control well))×100 was calculated. Data were analyzed using GraphPad Prism6.0 and fitted using the curve equation: Y=Bottom+(Top−Bottom)/(1+10^((Log $IC_{50}$−X)*HillSlope)), and $IC_{50}$ values were calculated. Table 1 summarizes the inhibitory effects of some compounds on ATM kinase activity (Inh %); Table 2 summarizes the $IC_{50}$ values of ATM kinase activity of some compounds.

TABLE 1

| Example | 1 | | | 2 | | | 3 | | | 4 | | |
|---|---|---|---|---|---|---|---|---|---|---|---|---|
| Conc. (nM) | 100 | 10 | 1 | 10 | 1 | 0.1 | | 10 | | | 10 | |
| Inh % | 96 | 71 | 25 | 96 | 59 | 45 | | 98 | | | 97 | |
| Example | 5 | | | 6 | | | 7 | | | 8 | | |
| Conc. (nM) | 10 | 1 | 0.1 | 10 | 1 | 0.1 | 10 | 1 | 0.1 | 10 | 1 | 0.1 |
| Inh % | 99 | 97 | 47 | 99 | 93 | 33 | 96 | 86 | 18 | 99 | 94 | 27 |
| Example | 9 | | | 10 | | | 11 | | | 12 | | |
| Conc. (nM) | 10 | 1 | 0.1 | 10 | 1 | 0.1 | 10 | 1 | 0.1 | 10 | 1 | 0.1 |
| Inh % | 99 | 96 | 28 | 99 | 74 | 13 | 97 | 78 | 11 | 98 | 91 | 40 |
| Example | 13 | | | 14 | | | 16 | | | 17 | | |
| Conc. (nM) | | 10 | | | 10 | | 10 | 1 | 0.1 | 10 | 1 | 0.1 |
| Inh % | | 15 | | | 93 | | 97 | 89 | 71 | 91 | 55 | 9 |
| Example | 18 | | | 19 | | | 20 | | | 21 | | |
| Conc. (nM) | 10 | 1 | 0.1 | | 1 | | | 1 | | | 1 | |
| Inh % | 98 | 87 | 30 | | 88 | | | 82 | | | 67 | |
| Example | 22 | | | 24 | | | 25 | | | 26 | | |
| Conc. (nM) | 10 | 1 | 0.1 | 10 | 1 | 0.1 | | 1 | | | 1 | |
| Inh % | 100 | 94 | 31 | 98 | 84 | 30 | | 69 | | | 54 | |
| Example | 33 | | | 36 | | | 37 | | | AZD0156 | | |
| Conc. (nM) | 10 | 1 | 0.1 | | 1 | | 10 | 1 | 0.1 | 100 | 10 | 1 |
| Inh % | 100 | 92 | 28 | | 40 | | 100 | 66 | 12 | 100 | 95 | 90 |

Note:
Example 1 herein is the compound of Example 37 of WO 2018/127195 A1.

TABLE 2

| Example | 15 | 31 | 32 | 33 | 38 | 39 | 40 |
|---|---|---|---|---|---|---|---|
| $IC_{50}$ (nM) | 0.31 | 0.62 | 0.10 | 0.20 | 0.20 | 0.20 | 0.20 |
| Example | 41 | 43 | 46 | 48 | 49 | 50 | 58 |
| $IC_{50}$ (nM) | 0.15 | 0.41 | 0.18 | 0.46 | 0.80 | 0.41 | 0.19 |
| Example | | 59 | | | AZD0156 | | |
| $IC_{50}$ (nM) | | 0.19 | | | 0.30 | | |

Therefore, as determined by the ATM kinase assay, the compound of Example 2 and its analogues have good inhibitory effect on ATM kinase.

Example 66

Determination of the Inhibitory Effect of the Compound of Example 2 and its Analogues in Combination with CPT-11 on the Proliferation of Human Colon Cancer Cell SW620 Using MTT Assay The human colon cancer cells SW620 were cultured in RPMI 1640 medium with 10% FBS and used at about 90% confluence for experiments. The SW620 cells were digested with trypsinase and centrifuged at 800 rpm for 5 minutes. The supernatant was discarded and the cell pellets were resuspended with fresh medium (RPMI 1640+10% FBS). The cells were seeded into 96-well cell culture plates with appropriate cell density and incubated at 37° C. overnight in a 5% $CO_2$ incubator. The stock solutions of the test compounds and the reference compound AZD0156 were serially diluted to 8 concentrations with DMSO at ratios of 1:3 and 1:10, respectively. The first concentration was 1 μM or 0.333 μM, the last concentration was DMSO negative control (0 μM). 5 μL of solutions of each concentration was added to 120 μL of medium (a 25 times dilution) and mixed by shaking. The cells were cultured overnight and the culture medium was replaced with 195 μL/well of fresh medium containing 205 nM CPT-11 and 5 μL/well of medium containing the test compound (the final concentration of DMSO was 1%). The culture plates were returned to incubator and cultured at 37° C., 5% $CO_2$ for 5 days. At the day of experiment, medium was discarded and replaced with 100 μL of fresh serum-free DMEM medium containing MTT (0.5 mg/mL), and the culture was continued. 4 hours later, the medium was discarded and replaced with 100 μL/well of DMSO, the plate was shaken for 10 minutes in dark and the absorbance was measured at the wavelengths of 552 and 690 nm using a multi-function plate reader. Data were analyzed by Graph Pad Prism 6.0. The inhibitory effects of compounds on cell proliferation were plotted based on cell viability vs. the logarithm of compound concentration. Cell viability $\%=(OD_{compound}-OD_{background})/(OD_{DMSO}-OD_{background})\times100$. The $IC_{50}$ values were fitted by a sigmoidal dose response curve equation $Y=100/(1+10\hat{}(\text{Log C}-\text{Log } IC_{50}))$, wherein C was the concentration of a compound.

Table 3 summarizes the inhibitory effect data ($IC_{50}$) of some compounds combined with CPT-11 on the proliferation of human colon cancer cell SW620.

TABLE 3

| Example | 1 | 2 | 3 | 4 | 5 | 6 | 7 | 8 |
|---|---|---|---|---|---|---|---|---|
| $IC_{50}$ (nM) | 123.1 | 19.2 | 40.2 | 41.1 | 19.5 | 12.6 | 25.9 | 24.1 |
| Example | 9 | 10 | 11 | 12 | 13 | 14 | 15 | 16 |
| $IC_{50}$ (nM) | 24.0 | 16.7 | 30.0 | 15.7 | >1000 | 39.7 | 9.3 | 8.2 |
| Example | 17 | 18 | 19 | 20 | 21 | 22 | 24 | 25 |
| $IC_{50}$ (nM) | 27.4 | 6.5 | 17.6 | 35.9 | 29.6 | 16.3 | 20.8 | 66.6 |
| Example | 26 | 31 | 32 | 33 | 35 | 36 | 37 | 38 |
| $IC_{50}$ (nM) | 51.0 | 10.1 | 9.2 | 18.3 | 564.3 | 72.6 | 17.6 | 8.7 |
| Example | 39 | 40 | 41 | 42 | 43 | 45 | 46 | 47 |
| $IC_{50}$ (nM) | 7.3 | 8.1 | 54.3 | 852.2 | 17.9 | 20.93 | 46.9 | 17.9 |
| Example | 48 | 49 | 50 | 52 | 58 | 59 | 60 | 61 |
| $IC_{50}$ (nM) | 12.1 | 7.1 | 6.3 | 5.5 | 23.3 | 12.0 | >1000 | 21.7 |
| Example | 62 | 63-A | 63-B | 64-A | 64-B | AZD0156 | a | b |
| $IC_{50}$ (nM) | 43.0 | 32.3 | 43.0 | 21.9 | 20.4 | 9.8 | 328.3 | 56.97 |
| Example | c | | | | d | | e | |
| $IC_{50}$ (nM) | 170.3 | | | | 127.7 | | 152.0 | |

Note:
Example 1 herein is the compound of Example 37 of WO 2018/127195 A1; Examples a, b, c, d and e are compounds of Examples 4, 26, 44, 45 and 47 of WO 2018/127195 A1, respectively.

Therefore, as determined by MTT assay, the compound of Example 2 and its analogues have good inhibitory effect on the proliferation of SW620 cell.

Example 67

Determination of the Inhibitory Effect of the Compound of Example 2 and its Analogues on the Proliferation of Human Breast Cancer Cell MDA-MB-468 Using MTT Assay The human breast cancer cells MDA-MB-468 were cultured in RPMI 1640 medium with 10% FBS and used at 90% confluence. The MDA-IVB-468 cells were digested with trypsinase and centrifuged at 800 rpm for 5 minutes. The supernatant was discarded and the cell pellets were resuspended with fresh medium and counted. Cells were seeded to 96-well cell culture plates with appropriate cell density and incubated overnight at 37° C., 5% $CO_2$. The stock solutions of test compounds or the reference compound AZD0156 were serially diluted to 8 concentrations with DMSO at ratios of 1:3 and 1:10, respectively: the first concentration was 1 μM or 0.333 μM and the last concentration was DMSO negative control (0 μM). 5 μL of solutions of each concentration was added to 120 μL of medium (diluted by 25 times) and mixed by shaking. The culture medium of cells cultured overnight was discarded and replaced with 195 μL/well of fresh medium (RPMI 1640+5% FBS) and 5 μL/well of diluted medium containing the test compound of corresponding concentrations (the final concentration of DMSO was 1%), and the culture plate was then returned to 5% $CO_2$ incubator at 37° C. for 7 days (on the fourth day, dressing was changed once and culture was continued). On the day of experiment, culture medium was discarded and replaced with 100 μL/well of fresh serum-free DMEM medium containing MTT (0.5 mg/mL), and the culture was continued. After 4 hours, medium was discarded and replaced with 100 μL/well of DMSO, the plates were shaken for 10 minutes in darkness and the absorbance was measured at the wavelengths of 552 and 693 nm using a multi-function plate reader. Graph Pad Prism 6.0 was used to analyze the data. The inhibitory effects of compounds on cell proliferation were plotted based on cell viability vs. the logarithm of compound concentration. Cell viability $\%=(OD_{compound}-OD_{background})/(OD_{DMSO}-OD_{background})\times100$. The $IC_{50}$ values were fitted by a sigmoidal dose response curve equation $Y=100/(1+10\hat{}(\text{Log C}-\text{Log } IC_{50}))$, wherein C was the concentration of a compound.

Table 4 summarizes the inhibitory effect data ($IC_{50}$) of some compounds on the proliferation of human breast cancer cell MDA-MB-468.

TABLE 4

| Example | 1 | 2 | 3 | 4 | 5 | 6 | 7 | 8 |
|---|---|---|---|---|---|---|---|---|
| $IC_{50}$ (nM) | 103.4 | 18.8 | 29.1 | 38.85 | 21.91 | 11.57 | 22.58 | 24.78 |
| Example | 9 | 10 | 11 | 12 | 13 | 14 | 15 | 16 |
| $IC_{50}$ (nM) | 23.1 | 16.44 | 31.1 | 14.37 | 781.6 | 25.99 | 7.98 | 10.62 |
| Example | 17 | 18 | 19 | 20 | 21 | 22 | 24 | 25 |
| $IC_{50}$ (nM) | 20.93 | 6.40 | 11.41 | 21.27 | 16.41 | 9.91 | 11.03 | 73.29 |
| Example | 26 | 31 | 32 | 33 | 35 | 36 | 37 | 38 |
| $IC_{50}$ (nM) | 48.58 | 9.2 | 7.6 | 18.54 | 419.0 | 58.8 | 24.86 | 6.9 |
| Example | 39 | 40 | 41 | 42 | 43 | 45 | 46 | 47 |
| $IC_{50}$ (nM) | 7.4 | 6.5 | 42.6 | 532.9 | 16.7 | 18.8 | 40.2 | 126.3 |
| Example | 48 | 49 | 50 | 52 | 58 | 59 | 60 | 61 |
| $IC_{50}$ (nM) | 7.6 | 4.5 | 8.1 | 6.1 | 17.8 | 9.2 | 832.2 | 20.8 |
| Example | 62 | 63-A | 63-B | 64-A | 64-B | AZD0156 | a | c |
| $IC_{50}$ (nM) | 34.0 | 31.1 | 25.5 | 16.6 | 13.8 | 9.87 | 950.4 | 183.3 |
| Example | | d | | | | e | | |
| $IC_{50}$ (nM) | | 106.2 | | | | 145.2 | | |

Note:
Example 1 herein is the compound of Example 37 of WO 2018/127195 A1; Examples a, c and d are compounds of Examples 4, 44, 45 and 47 of WO 2018/127195 A1, respectively.

Therefore, as determined by MTT assay, the compound of Example 2 and its analogues have good inhibitory effect on the proliferation of MDA-MB-468 cells.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A compound of Formula I, or a stereoisomer, a tautomer, a N-oxide, a hydrate, an isotope-substituted derivative, a solvate thereof, or a pharmaceutically acceptable salt thereof, or a mixture thereof:

I

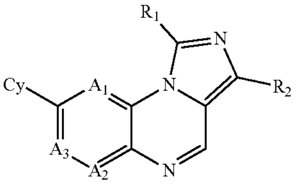

wherein $A_1$ is selected from the group consisting of N and $CR_4$; $A_2$ is selected from the group consisting of N and $CR_5$; $A_3$ is selected from the group consisting of N and $CR_6$;

Cy is selected from the group consisting of an optionally substituted aryl, an optionally substituted heteroaryl, an optionally substituted heterocyclic group, and an optionally substituted cycloalkyl;

$R_1$ is selected from the group consisting of an optionally substituted alkyl, an optionally substituted alkoxy, an optionally substituted amino, an optionally substituted carbocyclic group, an optionally substituted heterocyclic group, an optionally substituted aryl, and an optionally substituted heteroaryl;

$R_2$ is selected from the group consisting of an optionally substituted alkyl and an optionally substituted carbocyclic group; and $R_4$, $R_5$, and $R_6$ are independently selected from the group consisting of hydrogen, halogen, alkyl, alkoxy, alkenyl, alkynyl, amino, nitro, cyano, acylamino, acyloxy, hydroxy, sulfhydryl, alkylthio, azido, and carboxyl; wherein the alkyl, alkoxy, alkenyl, alkynyl, amino, acylamino, acyloxy, hydroxy, sulfhydryl, alkylthio, and carboxyl may be independently optionally substituted.

2. The compound of claim 1, or a stereoisomer, a tautomer, a N-oxide, a hydrate, an isotope-substituted derivative, a solvate thereof, or a pharmaceutically acceptable salt thereof, or a mixture thereof, wherein the compound of Formula I has the structure of Formula II:

II

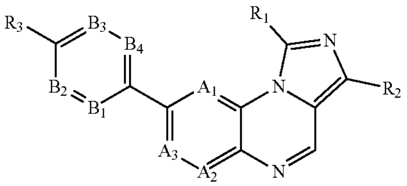

wherein $A_1$ is selected from the group consisting of N and $CR_4$; $A_2$ is selected from the group consisting of N and $CR_5$; $A_3$ is selected from the group consisting of N and $CR_6$;

$B_1$ is selected from the group consisting of N and $CR_7$; $B_2$ is selected from the group consisting of N and $CR_8$; $B_3$ is selected from the group consisting of N and $CR_9$; and $B_4$ is selected from the group consisting of N and $CR_{10}$;

$R_1$ is selected from the group consisting of an optionally substituted alkyl, an optionally substituted alkoxy, an optionally substituted amino, an optionally substituted carbocyclic group, an optionally substituted heterocyclic group, an optionally substituted aryl, and an optionally substituted heteroaryl;

$R_2$ is selected from the group consisting of an optionally substituted alkyl and an optionally substituted carbocyclic group;

$R_3$ is selected from the group consisting of hydrogen, alkoxy, amino, carbocyclic group, heterocyclic group, aryl, and heteroaryl; wherein the alkoxy, amino, carbocyclic group, heterocyclic group, aryl, or heteroaryl may be independently optionally substituted; and $R_4$, $R_5$, $R_6$, $R_7$, $R_8$, $R_9$, and $R_{10}$ are independently selected from the group consisting of hydrogen, halogen, alkyl, alkoxy, alkenyl, alkynyl, amino, nitro, cyano, acylamino, acyloxy, hydroxy, sulfhydryl, alkylthio, azido, and carboxyl; wherein the alkyl, alkoxy, alkenyl, alkynyl, amino, acylamino, acyloxy, hydroxy, sulfhydryl, alkylthio, and carboxyl may be independently optionally substituted.

3. The compound of claim 2, or a stereoisomer, a tautomer, a N-oxide, a hydrate, an isotope-substituted derivative, a solvate thereof, or a pharmaceutically acceptable salt thereof, or a mixture thereof, wherein, $A_1$, $A_2$, and $A_3$ are $CR_4$, $CR_5$, and $CR_6$, respectively, wherein $R_4$, $R_5$, and $R_6$ are independently selected from the group consisting of hydrogen, halogen, $C_{1-4}$ alkyl, $C_{1-4}$ alkoxy, and halogenated $C_{1-4}$ alkyl;

the ring containing $B_1$, $B_2$, $B_3$, and $B_4$ is selected from the group consisting of an optionally substituted pyridine ring and an optionally substituted phenyl ring;

$R_1$ is selected from the group consisting of an optionally substituted $C_{1-6}$ alkyl, heteroaryl group that is optionally substituted by 1-4 $C_{1-6}$ alkyls, and heterocyclic group that is optionally substituted by 1-4 $C_{1-6}$ alkyls;

$R_2$ is $C_{1-6}$ alkyl;

$R_3$ is selected from the group consisting of hydrogen, $C_{1-6}$ alkoxy that is optionally substituted by $—NR_{11}R_{12}$, $—NR_{11'}—C_{1-6}$ alkyl-$NR_{11'}R_{12'}$, and heterocyclic group that is optionally substituted by $—NR_{11}R_{12}$, wherein, $R_{11'}$ and $R_{12'}$ are independently selected from the group consisting of H and $C_{1-4}$ alkyl or they together with the N atom they link to form a 4 to 8-membered heterocyclic group optionally substituted by 1-3 substituents selected from the group consisting of halogen, alkyl, and alkoxy, and $R_{11}$ and $R_{12}$ are independently selected from the group consisting of hydrogen and $C_{1-6}$ alkyl, or $R_{11}$ and $R_{12}$ together with the N atom they link to form a 4 to 8-membered heterocyclic group, which is optionally substituted by 1-3 substituents selected from the group consisting of halogen, alkyl, and alkoxy; and $R_7$, $R_8$, $R_9$, and $R_{10}$ are independently selected from the group consisting of hydrogen, halo, $C_{1-4}$ alkyl, and halogenated $C_{1-4}$ alkyl.

4. The compound of claim 3, or a stereoisomer, a tautomer, a N-oxide, a hydrate, an isotope-substituted derivative, a solvate thereof, or a pharmaceutically acceptable salt thereof, or a mixture thereof, wherein, the ring containing $B_1B_2$, $B_3$, and $B_4$ is a pyridine ring in which $B_2$ is N;

$R_1$ is selected from the group consisting of $C_{1-4}$ alkyl, tetrahydropyranyl that is optionally substituted by 1-4 $C_{1-6}$ alkyls, piperidinyl that is optionally substituted by 1-4 $C_{1-6}$ alkyls, morpholinyl that is optionally substituted by 1-4 $C_{1-6}$ alkyls, and piperazinyl that is optionally substituted by 1-4 $C_{1-6}$ alkyls; and $R_2$ is methyl.

5. The compound of claim 2, wherein the compound is a compound of Formula IIIa or Formula IIIb, or a stereoisomer, a tautomer, a N-oxide, a hydrate, an isotope-substituted derivative, a solvate thereof, or a pharmaceutically acceptable salt thereof, or a mixture thereof:

IIIa

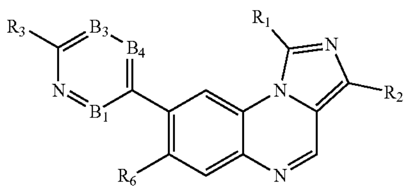

IIIb

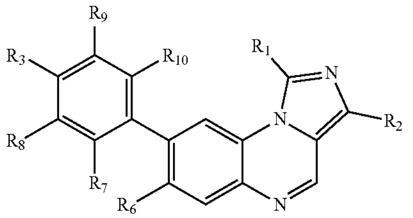

wherein $R_6$ is selected from the group consisting of hydrogen, halogen, alkyl, and alkoxy.

6. The compound of claim 5, or a stereoisomer, a tautomer, a N-oxide, a hydrate, an isotope-substituted derivative, a solvate thereof, or a pharmaceutically acceptable salt thereof, or a mixture thereof, wherein, the ring containing $B_1$, $B_3$, and $B_4$ is an optionally substituted pyridine ring;

$R_1$ is selected from the group consisting of an optionally substituted $C_{1-6}$ alkyl, heteroaryl that is optionally substituted by 1-4 $C_{1-6}$ alkyls, and heterocyclic group that is optionally substituted by 1-4 $C_{1-6}$ alkyls;

$R_2$ is $C_{1-3}$ alkyl;

$R_3$ is selected from the group consisting of hydrogen, $C_{1-6}$ alkoxy that is optionally substituted by $-NR_{11}R_{12}$, $-NR_{11'}-C_{1-6}$ alkyl-$NR_{11'}R_{12'}$, and heterocyclic group that is optionally substituted by $-NR_{11}R_{12}$, wherein $R_{11'}$ and $R_{12'}$ are independently selected from the group consisting of H and $C_{1-4}$ alkyl or they together with the N atom they link to form a 4 to 8-membered heterocyclic group optionally substituted by 1-3 substituents selected from the group consisting of halogen, alkyl, and alkoxy, and $R_{11}$ and $R_{12}$ are independently selected from hydrogen or $C_{1-6}$ alkyl, or $R_{11}$ and $R_{12}$ together with the N atom they link to form a 4 to 8-membered heterocyclic group, which is optionally substituted by 1-3 substituents selected from the group consisting of halogen, alkyl, and alkoxy;

$R_6$ is selected from the group consisting of hydrogen, halogen, $C_{1-4}$ alkyl, and $C_{1-4}$ alkoxy; and $R_7$, $R_8$, $R_9$, and $R_{10}$ are independently selected from the group consisting of hydrogen, $C_{1-4}$ alkoxy, halogen, $C_{1-4}$ alkyl, and halogenated $C_{1-4}$ alkyl.

7. The compound of claim 6, or a stereoisomer, a tautomer, a N-oxide, a hydrate, an isotope-substituted derivative, a solvate thereof, or a pharmaceutically acceptable salt thereof, or a mixture thereof, wherein, $R_1$ is selected from the group consisting of $C_{1-4}$ alkyl, tetrahydropyranyl that is optionally substituted by 1-4 $C_{1-6}$ alkyls, piperidinyl that is optionally substituted by 1-4 $C_{1-6}$ alkyls, morpholinyl that is optionally substituted by 1-4 $C_{1-6}$ alkyls, and piperazinyl that is optionally substituted by 1-4 $C_{1-6}$ alkyls;

$R_6$ is hydrogen;

$R_7$, $R_9$, and $R_{10}$ are hydrogen; and $R_8$ is selected from the group consisting of hydrogen, halogen, $C_{1-4}$ alkoxy, $C_{1-4}$ alkyl, and halogenated $C_{1-4}$ alkyl.

8. The compound of claim 5, or a stereoisomer, a tautomer, a N-oxide, a hydrate, an isotope-substituted derivative, a solvate thereof, or a pharmaceutically acceptable salt thereof, or a mixture thereof, wherein in Formulae IIIa and IIIb:

$R_1$ is a heterocyclic group optionally substituted by 1-2 substituents selected from the group consisting of $C_{1-6}$ alkyl;

$R_2$ is $C_{1-4}$ alkyl;

$R_3$ is a $C_{1-6}$ alkoxy optionally substituted by $-NR_{11}R_{12}$, or a heterocyclic group optionally substituted by $-NR_{11}R_{12}$, wherein $R_{11}$ and $R_{12}$ are independently selected from hydrogen or $C_{1-6}$ alkyl or $R_{11}$ and $R_{12}$ together with the N atom they link to form a 4 to 8-membered heterocyclic group optionally substituted by 1-2 alkyls;

$R_6$ is selected from the group consisting of hydrogen, halogen, and $C_{1-4}$ alkoxy; and in Formula IIIa, $B_1$, $B_3$, and $B_4$ are CH;

in Formula IIIb, $R_7$, $R_9$, and $R_{10}$ are H.

9. The compound of claim 8, or a stereoisomer, a tautomer, a N-oxide, a hydrate, an isotope-substituted derivative, a solvate thereof, or a pharmaceutically acceptable salt thereof, or a mixture thereof, wherein in Formulae IIIa and IIIb:

$R_1$ is morpholinyl optionally substituted by 1-2 $C_{1-6}$ alkyls;

$R_2$ is methyl;

the heterocyclic group optionally substituted by $-NR_{11}R_{12}$ in $R_3$ is a piperidinyl or a piperazinyl with their ring nitrogen atom linking to the rest of the compound, which is optionally substituted by the $-NR_{11}R_{12}$ group;

$R_6$ is hydrogen; and in Formula IIIa, $B_1$, $B_3$, and $B_4$ are CH;

in Formula IIIb, $R_7$, $R_9$, and $R_{10}$ are H.

10. The compound of claim 5, or a stereoisomer, a tautomer, a N-oxide, a hydrate, an isotope-substituted derivative, a solvate thereof, or a pharmaceutically acceptable salt thereof, or a mixture thereof, wherein in Formula IIIb:

$R_1$ is selected from the group consisting of a $C_{1-6}$ alkyl, a heteroaryl optionally substituted by 1-3 substituents selected from the group consisting of halogen, $C_{1-4}$ alkyl, and $C_{1-4}$ alkoxy, and a heterocyclic group optionally substituted by 1-2 substituents selected from the group consisting of $C_{1-6}$ alkyl;

$R_2$ is $C_{1-6}$ alkyl;

$R_3$ is $C_{1-6}$ alkoxy optionally substituted by $—NR_{11}R_{12}$, $—NR_{11'}—C_{1-6}$ alkyl-$NR_{11'}R_{12'}$, or heterocyclic group optionally substituted by $—NR_{11}R_{12}$, wherein $R_{11'}$ and $R_{12'}$ are independently selected from the group consisting of H and $C_{1-4}$ alkyl, $R_{11}$ and $R_{12}$ are independently selected from hydrogen or $C_{1-6}$ alkyl or $R_1$ and $R_{12}$ together with the N atom they link to form a 4 to 8-membered heterocyclic group optionally substituted by 1-2 alkyls;

$R_6$ is selected from the group consisting of hydrogen, halogen, and $C_{1-4}$ alkoxy;

$R_7$, $R_9$, and $R_{10}$ are H; and $R_8$ is selected from the group consisting of H, halogen, $C_{1-4}$ alkyl substituted by 1-4 halogen, and $C_{1-4}$ alkoxy.

11. The compound of claim 5, or a stereoisomer, a tautomer, a N-oxide, a hydrate, an isotope-substituted derivative, a solvate thereof, or a pharmaceutically acceptable salt thereof, or a mixture thereof, wherein:

$R_1$ is selected from the group consisting of:

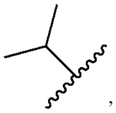 , 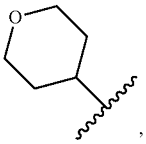 , 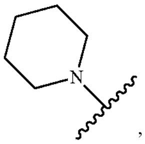 ,

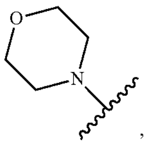 , 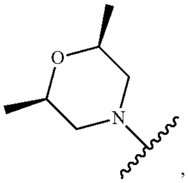 , 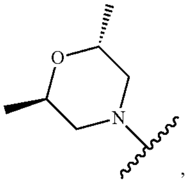 ,

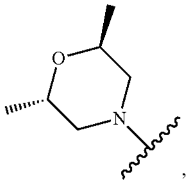 , 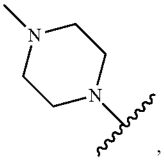 , 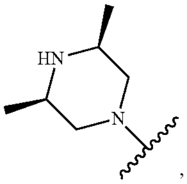 ,

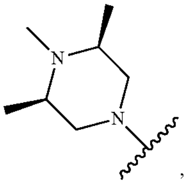 , and 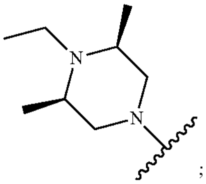 ;

$R_2$ is $C_{1-3}$ alkyl;

$R_3$ is selected from the group consisting of:

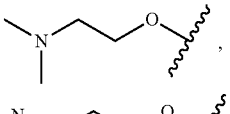 , 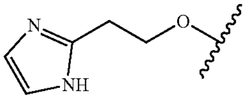 ,

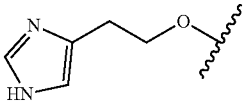 , 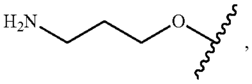 ,

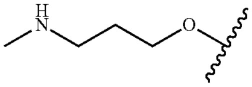 , 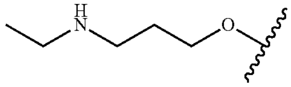 ,

-continued

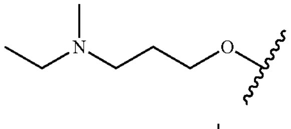 ,

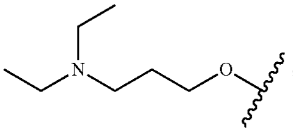 , 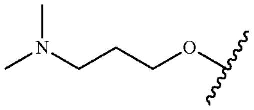 ,

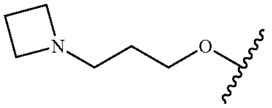 ,

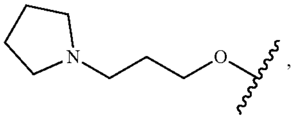 ,

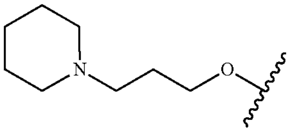 ,

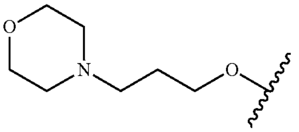 ,

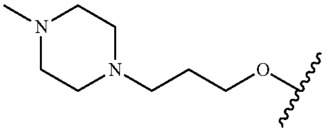 ,

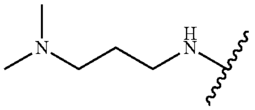 , 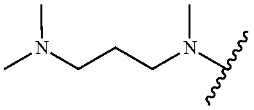 ,

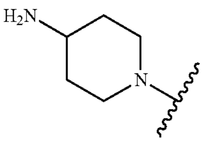 , 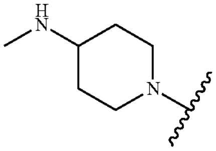 ,

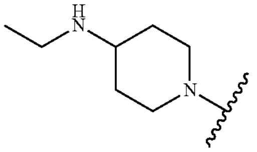 , 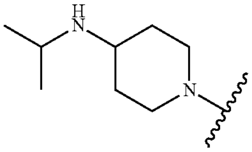 ,

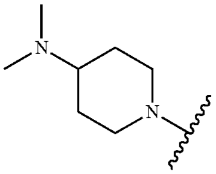 , and 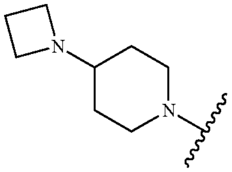 .

12. The compound of claim 5, or a stereoisomer, a tautomer, a N-oxide, a hydrate, an isotope-substituted derivative, a solvate thereof, or a pharmaceutically acceptable salt thereof, or a mixture thereof, wherein in Formula IIIb:

$R_1$ is selected from the group consisting of $C_{1-4}$ alkyl, tetrahydropyranyl optionally substituted by 1-2 $C_{1-6}$ alkyls, piperidinyl optionally substituted by 1-2 $C_{1-6}$ alkyls, morpholinyl optionally substituted by 1-2 $C_{1-6}$ alkyls, pyridyl optionally substituted by 1-2 substituents selected from the group consisting of halogen and $C_{1-4}$ alkoxy, and piperazinyl optionally substituted by 1-3 $C_{1-6}$ alkyls;

$R_2$ is $C_{1-4}$ alkyl;

$R_3$ is a piperidinyl or a piperazinyl with their ring nitrogen atom linking to the rest of the compound, and $R_3$ is optionally substituted by a —$NR_{11}R_{12}$ group, wherein $R_{11}$ and $R_{12}$ are independently selected from hydrogen or $C_{1-6}$ alkyl or $R_{11}$ and $R_{12}$ together with the N atom they link to form a 4 to 8-membered heterocyclic group optionally substituted by 1-2 alkyls.

13. A compound of claim 1, wherein the compound is selected from the group consisting of:

N,N-dimethyl-3-((5-(3-methyl-1-(tetrahydro-2H-pyran-4-yl)imidazo[1,5-a]quinoxalin-8-yl)pyridin-2-yl)oxy)propan-1-amine;

N,N-dimethyl-3-(4-(3-methyl-1-(tetrahydro-2H-pyran-4-yl)imidazo[1,5-a]quinoxalin-8-yl)phenoxy)propan-1-amine;

N,N-dimethyl-3-(2-fluoro-4-(3-methyl-1-(tetrahydro-2H-pyran-4-yl)imidazo[1,5-a]quinoxalin-8-yl)phenoxy)propan-1-amine;

N,N-dimethyl-3-(4-(3-methyl-1-(tetrahydro-2H-pyran-4-yl)imidazo[1,5-a]quinoxalin-8-yl)-2-(trifluoromethyl)phenoxy)propan-1-amine;

N,N-dimethyl-1-(2-fluoro-4-(3-methyl-1-(tetrahydro-2H-pyran-4-yl)imidazo[1,5-a]quinoxalin-8-yl)phenyl)piperidin-4-amine;

N,N-dimethyl-1-(2-chloro-4-(3-methyl-1-(tetrahydro-2H-pyran-4-yl)imidazo[1,5-a]quinoxalin-8-yl)phenyl)piperidin-4-amine;

N,N-dimethyl-1-(4-(3-methyl-1-(tetrahydro-2H-pyran-4-yl)imidazo[1,5-a]quinoxalin-8-yl)-2-(trifluoromethyl)phenyl)piperidin-1-amine;

1-(4-(3-methyl-1-(tetrahydro-2H-pyran-4-yl)imidazo[1,5-a]quinoxalin-8-yl)-2-(trifluoromethyl)phenyl)piperidin-4-amine;

N-methyl-1-(4-(3-methyl-1-(tetrahydro-2H-pyran-4-yl)imidazo[1,5-a]quinoxalin-8-yl)-2-(trifluoromethyl)phenyl)piperidin-4-amine;

N-ethyl-1-(4-(3-methyl-1-(tetrahydro-2H-pyran-4-yl)imidazo[1,5-a]quinoxalin-8-yl)-2-(trifluoromethyl)phenyl)piperidin-4-amine;

3-methyl-8-(6-(3-(piperidin-yl)propoxy)pyridin-3-yl)-1-(tetrahydro-2H-pyran-4-yl)imidazo[1,5-a]quinoxaline;

8-(1,3-dimethyl-1H-pyrazol-4-yl)-3-methyl-1-(tetrahydro-2H-pyran-4-yl)imidazo[1,5-a]quinoxaline;

N,N-dimethyl-3-((5-(3-methyl-1-morpholinylimidazo[1,5-a]quinoxalin-8-yl)pyridin-2-yl)oxy)propan-1-amine;

N,N-dimethyl-3-((5-(1-((2S,6R)-2,6-dimethylmorpholino)-3-methylimidazo[1,5-a]quinoxalin-8-yl)pyridin-2-yl)oxy)propan-1-amine;

N,N-dimethyl-3-((5-(3-methyl-1-(piperidin-1-yl)imidazo[1,5-a]quinoxalin-8-yl)pyridin-2-yl)oxy)propan-1-amine;

N,N-dimethyl-3-((5-(3-methyl-1-(4-methylpiperazin-1-yl)imidazo[1,5-a]quinoxalin-8-yl)pyridin-2-yl)oxy)propan-1-amine;

N,N-dimethyl-3-((5-(3-methyl-1-((3S,5R)-3,4,5-trimethylpiperazin-1-yl)imidazo[1,5-a]quinoxalin-8-yl)pyridin-2-yl)oxy)propan-1-amine;

N,N-dimethyl-3-((5-(1-isopropyl-3-methylimidazo[1,5-a]quinoxalin-8-yl)pyridin-2-yl)oxy)propan-1-amine;

N,N-dimethyl-3-(2-fluoro-4-(1-isopropyl-3-methylimidazo[1,5-a]quinoxalin-8-yl)phenoxy)propan-1-amine;

N,N-dimethyl-3-(4-(1-isopropyl-3-methylimidazo[1,5-a]quinoxalin-8-yl)-2-(trifluoromethyl)phenoxy)propan-1-amine;

1-isopropyl-3-methyl-8-(6-(3-(piperidin-1-yl)propoxy)pyridin-3-yl)imidazo[1,5-a]quinoxaline;

7-fluoro-1-isopropyl-3-methyl-8-(6-(3-(piperidin-1-yl)propoxy)pyridin-3yl)imidazo[1,5-a]quinoxaline;

N,N-dimethyl-1-(2-fluoro-4-(1-isopropyl-3-methylimidazo[1,5-a]quinoxalin-8-yl)phenyl)piperidin-4-amine;

N,N-dimethyl-1-(2-chloro-4-(1-isopropyl-3-methylimidazo[1,5-a]quinoxalin-8-yl)phenyl)piperidin-4-amine;

N,N-dimethyl-1-(4-(1-isopropyl-3-methylimidazo[1,5-a]quinoxalin-8-yl)-2-(trifluoromethyl)phenyl)piperidin-4-amine;

1-(4-(1-isopropyl-3-methylimidazo[1,5-a]quinoxalin-8-yl)-2-(trifluoromethyl)phenyl)piperidin-4-amine;

N-methyl-1-(4-(1-isopropyl-3-methylimidazo[1,5-a]quinoxalin-8-yl)-2-(trifluoromethyl)phenyl)piperidin-4-amine;

N-ethyl-1-(4-(1-isopropyl-3-methylimidazo[1,5-a]quinoxalin-8-yl)-2-(trifluoromethyl)phenyl)piperidin-4-amine;

8-(1,3-dimethyl-4H-1$\lambda^4$-pyrazol-4-yl)-1-(3-fluoro-5-methoxypyridin-4-yl)-7-methoxy-3-methylimidazo[1,5-a]quinoxaline;

(2S,6R)-4-(8-(6-(3-(azetidin-1-yl)propoxy)pyridin-3-yl)-3-methylimidazo[1,5-a]quinoxalin-1-yl)-2,6-dimethylmorpholine;

(2S,6R)-2,6-dimethyl-4-(3-methyl-8-(6-(3-(pyrrolidin-1-yl)propoxy)pyridin-3-yl)imidazo[1,5-a]quinoxalin-1-yl)morpholine;

(2S,6R)-2,6-dimethyl-4-(3-methyl-8-(6-(3-(piperidin-1-yl)propoxy)pyridin-3-yl)imidazo[1,5-a]quinoxalin-1-yl)morpholine;

(2S,6R)-4-(8-(6-(2-(1H-imidazol-2-yl)ethoxy)pyridin-3-yl)-3-methylimidazo[1,5-a]quinoxalin-1-yl)-2,6-dimethylmorpholine;

(2S,6R)-4-(8-(6-(2-(1H-imidazol-4-yl)ethoxy)pyridin-3-yl)-3-methylimidazo[1,5-a]quinoxalin-1-yl)-2,6-dimethylmorpholine;

2-((5-(1-((2S,6R)-2,6-dimethylmorpholino)-3-methylimidazo[1,5-a]quinoxalin-8-yl)pyridin-2-yl)oxy)-N,N-dimethylethan-1-amine;

3-((4-(1-((2S,6R)-2,6-dimethylmorpholino)-3-methylimidazo[1,5-a]quinoxalin-8-yl)-2-(trifluoromethyl)phenoxy)-N,N-dimethylpropan-1-amine;

1-(5-(1-((2S,6R)-2,6-dimethylmorpholino)-3-methylimidazo[1,5-a]quinoxalin-8-yl)pyridin-2-yl)-N,N-dimethylpiperidin-4-amine;

1-(4-(1-((2S,6R)-2,6-dimethylmorpholino)-3-methylimidazo[1,5-a]quinoxalin-8-yl)-2-fluorophenyl)-N,N-dimethylpiperidin-4-amine;

1-(2-chloro-4-(1-((2S,6R)-2,6-dimethylmorpholino)-3-methylimidazo[1,5-a]quinoxalin-8-yl)phenyl)-N,N-dimethylpiperidin-4-amine;

3-((5-(1-((2S,6R)-2,6-dimethylmorpholino)-3-ethylimidazo[1,5-a]quinoxalin-8-yl)pyridin-2-yl)oxy)-N,N-dimethylpropan-1-amine;

3-((5-(1-((2S,6R)-2,6-dimethylmorpholino)-3-isopropylimidazo[1,5-a]quinoxalin-8-yl)pyridin-2-yl)oxy)-N,N-dimethylpropan-1-amine;

3-((5-(1-((2S,6R)-2,6-dimethylmorpholino)imidazo[1,5-a]quinoxalin-8-yl)pyridin-2-yl)oxy)-N,N-dimethylpropan-1-amine;

N,N-dimethyl-3-((5-(1-((3S,5R)-3,4,5-trimethylpiperazin-1-yl)imidazo[1,5-a]quinoxalin-8-yl)pyridin-2-yl)oxy)propan-1-amine;

1-(5-(1-((2S,6R)-2,6-dimethylmorpholino)imidazo[1,5-a]quinoxalin-8-yl)pyridin-2-yl)-N,N-dimethylpiperidin-4-amine;

$N^1$-(5-(1-((2S,6R)-2,6-dimethylmorpholino)-3-methylimidazo[1,5-a]quinoxalin-8-yl)pyridin-2-yl)-$N^3$,$N^3$-dimethylpropane-1,3-diamine;

$N^1$-(5-(1-((2S,6R)-2,6-dimethylmorpholino)-3-methylimidazo[1,5-a]quinoxalin-8-yl)pyridin-2-yl)-$N^1$,$N^3$,$N^3$-trimethylpropane-1,3-diamine;

1-(5-(1-((2S,6R)-2,6-dimethylmorpholino)-3-methylimidazo[1,5-a]quinoxalin-8-yl)pyridin-2-yl)piperidin-4-amine;

1-(5-(1-((2S,6R)-2,6-dimethylmorpholino)-3-methylimidazo[1,5-a]quinoxalin-8-yl)pyridin-2-yl)-N-methylpiperidin-4-amine;

1-(5-(1-((2S,6R)-2,6-dimethylmorpholino)-3-methylimidazo[1,5-a]quinoxalin-8-yl)pyridin-2-yl)-N-ethylpiperidin-4-amine;

1-(5-(1-((2S,6R)-2,6-dimethylmorpholino)-3-methylimidazo[1,5-a]quinoxalin-8-yl)pyridin-2-yl)-N-isopropylpiperidin-4-amine;

(2S,6R)-4-(8-(6-(4-(azetidin-1-yl)piperidin-1-yl)pyridin-3-yl)-3-methylimidazo[1,5-a]quinoxalin-1-yl)-2,6-dimethylmorpholine;

3-((5-(1-((2S,6R)-2,6-dimethylmorpholino)-3-methylimidazo[1,5-a]quinoxalin-8-yl)pyridin-2-yl)oxy)propan-1-amine;

3-((5-(1-((2S,6R)-2,6-dimethylmorpholino)-3-methylimidazo[1,5-a]quinoxalin-8-yl)pyridin-2-yl)oxy)-N-methylpropan-1-amine;

3-((5-(1-((2S,6R)-2,6-dimethylmorpholino)-3-methylimidazo[1,5-a]quinoxalin-8-yl)pyridin-2-yl)oxy)-N-ethylpropan-1-amine;

3-((5-(1-((2S,6R)-2,6-dimethylmorpholino)-3-methylimidazo[1,5-a]quinoxalin-8-yl)pyridin-2-yl)oxy)-N-ethyl-N-methylpropan-1-amine;

3-((5-(1-((2S,6R)-2,6-dimethylmorpholino)-3-methylimidazo[1,5-a]quinoxalin-8-yl)pyridin-2-yl)oxy)-N,N-diethylpropan-1-amine;

(2S,6R)-2,6-dimethyl-4-(3-methyl-8-(6-(3-morpholinopropoxy)pyridin-3-yl)imidazo[1,5-a]quinoxalin-1-yl)morpholine;

(2S,6R)-2,6-dimethyl-4-(3-methyl-8-(6-(3-(4-methylpiperazin-1-yl)propoxy)pyridin-3-yl)imidazo[1,5-a]quinoxalin-1-yl)morpholine;

(2S,6R)-2,6-dimethyl-4-(3-methyl-8-(6-(2-(4-methylpiperazin-1-yl)ethyl)pyridin-3-yl)imidazo[1,5-a]quinoxalin-1-yl)morpholine;

3-(4-(1-((2S,6R)-2,6-dimethylmorpholino)-3-methylimidazo[1,5-a]quinoxalin-8-yl)-2-fluorophenoxy)-N,N-dimethylpropan-1-amine;

3-(2-chloro-4-(1-((2S,6R)-2,6-dimethylmorpholino)-3-methylimidazo[1,5-a]quinoxalin-8-yl)phenoxy)-N,N-dimethylpropan-1-amine;

1-(5-(1-((2R,6R)-2,6-dimethylmorpholino)-3-methylimidazo[1,5-a]quinoxalin-8-yl)pyridin-2-yl)-N,N-dimethylpiperidin-4-amine and 1-(5-(1-((2S,6S)-2,6-dimethylmorpholino)-3-methylimidazo[1,5-a]quinoxalin-8-yl)pyridin-2-yl)-N,N-dimethylpiperidin-4-amine;

3-((5-(1-((2R,6R)-2,6-dimethylmorpholino)-3-methylimidazo[1,5-a]quinoxalin-8-yl)pyridin-2-yl)oxy)-N,N-dimethylpropan-1-amine and 3-((5-(1-((2S,6S)-2,6-dimethylmorpholino)-3-methylimidazo[1,5-a]quinoxalin-8-yl)pyridin-2-yl)oxy)-N,N-dimethylpropan-1-amine;

or a stereoisomer, a tautomer, a N-oxide, a hydrate, an isotope-substituted derivative, a solvate thereof, or a pharmaceutically acceptable salt thereof, or a mixture thereof.

14. A pharmaceutical composition comprising the compound of claim 1 and a pharmaceutically acceptable carrier.

15. The pharmaceutical composition of claim 14, wherein the composition further comprises at least one known anticancer agent or a pharmaceutically acceptable salt of the anticancer agent.

16. The pharmaceutical composition of claim 15, wherein the composition further comprises at least one anticancer agent selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, Ofatumumab, avastin, herceptin, mabthera, imatinib, gefitinib, erlotinib, lapatinib, sorafenib, sunitinib, nilotinib, dasatinib, pazopanib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, Venetoclax, Aldesleukin, Sipueucel-T, Palbociclib, Olaparib, Niraparib, Rucaparib, Talazoparib, and Senaparib.

17. A method for treating or preventing a disease caused by a DDR function defect or a disease that benefits from inhibition of kinase activity in a subject in need thereof, comprising administering to the subject an effective amount of a compound or a stereoisomer, a tautomer, a N-oxide, a hydrate, an isotope-substituted derivative, a solvate or a pharmaceutically acceptable salt thereof, or a mixture thereof of claim 1, or a pharmaceutical composition comprising the compound or a stereoisomer, a tautomer, a N-oxide, a hydrate, an isotope-substituted derivative, a solvate, or a pharmaceutically acceptable salt thereof, or a mixture thereof, and a pharmaceutically acceptable carrier.

18. The method of claim 17, wherein the disease is a cancer.

19. The method of claim 18, wherein the cancer is selected from the group consisting of liver cancer, melanoma, Hodgkin's disease, non-Hodgkin's lymphoma, acute lymphocytic leukemia, chronic lymphocytic leukemia, multiple myeloma, neuroblastoma, breast cancer, ovarian cancer, lung cancer, Wilms tumor, cervical cancer, testicular cancer, soft tissue sarcoma, chronic lymphocytic leukemia, primary macroglobulinemia, bladder cancer, chronic myeloid leukemia, primary brain cancer, malignant melanoma, small cell lung cancer, gastric cancer, colon cancer, malignant pancreatic islet tumor, malignant carcinoid cancer, malignant melanoma, choriocarcinoma, mycosis fungoides, head and neck cancer, osteogenic sarcoma, pancreatic cancer, acute myeloid leukemia, hairy cell leukemia, rhabdomyosarcoma, Kaposi's sarcoma, urogenital tumors, thyroid cancer, esophageal cancer, malignant hypercalcemia, cervical hyperplasia, renal cell carcinoma, endometrial cancer, polycythemia vera, idiopathic thrombocythemia, adrenocortical carcinoma, skin cancer, prostate cancer, and Huntington's disease.

20. The method of claim 19, further comprising administering to the subject at least one known anticancer agent or a pharmaceutically acceptable salt of the anticancer agent; or wherein the subjected is treated in combination with radiotherapy.

21. The method of claim 20, wherein the at least one anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, Ofatumumab, avastin, herceptin, mabthera, imatinib, gefitinib, erlotinib, lapatinib, sorafenib, sunitinib, nilotinib, dasatinib, pazopanib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, Venetoclax, Aldesleukin, Sipueucel-T, Palbociclib, Olaparib, Niraparib, Rucaparib, Talazoparib, and Senaparib.

* * * * *